United States Patent
Rosenthal et al.

(10) Patent No.: US 8,042,264 B2
(45) Date of Patent: Oct. 25, 2011

(54) METHOD OF FABRICATING AN ELECTROACTIVE POLYMER TRANSDUCER

(75) Inventors: Marcus A. Rosenthal, Pacifica, CA (US); Qibing Pei, Temecula, CA (US); Neville A. Bonwit, Sunnyvale, CA (US)

(73) Assignee: SRI International, Monlo Park, CA (US)

( * ) Notice: Subject to any disclaimer, the term of this patent is extended or adjusted under 35 U.S.C. 154(b) by 0 days.

(21) Appl. No.: 12/827,898

(22) Filed: Jun. 30, 2010

(65) Prior Publication Data

US 2010/0263181 A1    Oct. 21, 2010

Related U.S. Application Data

(60) Division of application No. 12/412,032, filed on Mar. 26, 2009, now abandoned, which is a continuation of application No. 11/695,976, filed on Apr. 3, 2007, now Pat. No. 7,761,981, which is a continuation of application No. 10/793,401, filed on Mar. 3, 2004, now Pat. No. 7,233,097, and a continuation-in-part of application No. 10/154,449, filed on May 21, 2002, now Pat. No. 6,891,317.

(60) Provisional application No. 60/451,742, filed on Mar. 3, 2003, provisional application No. 60/293,003, filed on May 22, 2001.

(51) Int. Cl.
*H01R 43/00* (2006.01)

(52) U.S. Cl. .......... 29/825; 29/25.03; 29/25.41; 29/837; 29/846

(58) Field of Classification Search ................. 29/25.03, 29/25.41, 825, 837, 846
See application file for complete search history.

(56) References Cited

U.S. PATENT DOCUMENTS

| | | | |
|---|---|---|---|
| 3,050,034 A | 8/1962 | Benton |
| 3,783,480 A | 1/1974 | Booe |
| 3,832,580 A | 8/1974 | Yamamuro et al. |
| 3,851,363 A | 12/1974 | Booe |

(Continued)

FOREIGN PATENT DOCUMENTS

JP    2000-83389    3/2000

(Continued)

OTHER PUBLICATIONS

Conducting Polymer Electromechanical actuators a paper by R. H. Baughman et al in Conjugated Polymeric Materials, Opportunities in in Electronics Optoelectronics and Molecular Electronics eds. T. L. Bredas and R. R. Chance, Kluwer Academic Publishers, the Netherlands, 1990.*

(Continued)

*Primary Examiner* — Carl Arbes
(74) *Attorney, Agent, or Firm* — John E. Mrozinski, Jr.; Noland J. Cheung

(57) ABSTRACT

The invention describes rolled electroactive polymer devices. The invention also describes employment of these devices in a wide array of applications and methods for their fabrication. A rolled electroactive polymer device converts between electrical and mechanical energy; and includes a rolled electroactive polymer and at least two electrodes to provide the mechanical/electrical energy conversion. Prestrain is typically applied to the polymer. In one embodiment, a rolled electroactive polymer device employs a mechanism, such as a spring, that provides a force to prestrain the polymer. Since prestrain improves mechanical/electrical energy conversion for many electroactive polymers, the mechanism thus improves performance of the rolled electroactive polymer device.

14 Claims, 24 Drawing Sheets

U.S. PATENT DOCUMENTS

| | | | |
|---|---|---|---|
| 4,266,339 A * | 5/1981 | Kalt | 29/829 |
| 4,284,921 A | 8/1981 | Lemonon et al. | |
| 4,342,936 A | 8/1982 | Marcus et al. | |
| 4,400,634 A | 8/1983 | Micheron | |
| 4,413,202 A | 11/1983 | Krempl et al. | |
| 4,435,667 A | 3/1984 | Kolm et al. | |
| 4,469,978 A | 9/1984 | Hamada et al. | |
| 4,843,275 A | 6/1989 | Radice | |
| 4,885,783 A | 12/1989 | Whitehead et al. | |
| 4,911,995 A | 3/1990 | Belanger et al. | |
| 5,153,820 A | 10/1992 | MacFarlane et al. | |
| 5,361,240 A | 11/1994 | Pearce | |
| 5,410,210 A | 4/1995 | Sato et al. | |
| 5,438,553 A | 8/1995 | Wilson et al. | |
| 5,440,194 A | 8/1995 | Beurrier | |
| 5,452,878 A | 9/1995 | Gravesen et al. | |
| 5,481,152 A | 1/1996 | Buschulte | |
| 5,509,888 A | 4/1996 | Miller | |
| 5,559,387 A | 9/1996 | Beurrier | |
| 5,593,462 A | 1/1997 | Gueguen et al. | |
| 5,632,841 A * | 5/1997 | Hellbaum et al. | 156/245 |
| 5,642,015 A * | 6/1997 | Whitehead et al. | 310/309 |
| 5,933,170 A | 8/1999 | Takeuchi et al. | |
| 5,977,685 A | 11/1999 | Kurita et al. | |
| 6,048,622 A | 4/2000 | Hagood, IV et al. | |
| 6,060,811 A | 5/2000 | Fox et al. | |
| 6,093,995 A | 7/2000 | Lazarus et al. | |
| 6,190,805 B1 | 2/2001 | Takeuchi et al. | |
| 6,210,827 B1 | 4/2001 | Dopp et al. | |
| 6,343,129 B1 | 1/2002 | Pelrine et al. | |
| 6,376,971 B1 * | 4/2002 | Pelrine et al. | 310/363 |
| 6,379,393 B1 | 4/2002 | Mavroidis et al. | |
| 6,400,065 B1 | 6/2002 | Toda et al. | |
| 6,435,840 B1 | 8/2002 | Sharma et al. | |
| 6,437,489 B1 | 8/2002 | Shinke et al. | |
| 6,514,237 B1 | 2/2003 | Maseda | |
| 6,545,384 B1 | 4/2003 | Pelrine et al. | |
| 6,562,513 B1 | 5/2003 | Takeuchi et al. | |
| 6,583,533 B2 | 6/2003 | Pelrine et al. | |
| 6,664,718 B2 | 12/2003 | Pelrine et al. | |
| 6,768,246 B2 | 7/2004 | Pelrine et al. | |
| 6,781,284 B1 | 8/2004 | Pelrine et al. | |
| 6,809,462 B2 | 10/2004 | Pelrine et al. | |
| 6,812,624 B1 | 11/2004 | Pei et al. | |
| 6,867,533 B1 | 3/2005 | Su et al. | |
| 6,882,086 B2 | 4/2005 | Kornbluh et al. | |
| 6,891,317 B2 | 5/2005 | Pei et al. | |
| 6,911,764 B2 | 6/2005 | Pelrine et al. | |
| 7,034,432 B1 | 4/2006 | Pelrine et al. | |
| 7,038,357 B2 | 5/2006 | Goldenberg et al. | |
| 7,368,862 B2 | 5/2008 | Pelrine et al. | |
| 7,442,421 B2 | 10/2008 | Li et al. | |
| 7,442,760 B2 | 10/2008 | Roberts et al. | |
| 7,761,981 B2 * | 7/2010 | Rosenthal et al. | 29/825 |
| 2002/0013545 A1 | 1/2002 | Soltanpour et al. | |
| 2002/0130673 A1 | 9/2002 | Pelrine et al. | |
| 2003/0006669 A1 | 1/2003 | Pei et al. | |
| 2008/0191585 A1 | 8/2008 | Pelrine et al. | |

FOREIGN PATENT DOCUMENTS

| | | |
|---|---|---|
| JP | 2001-286162 A2 | 10/2001 |
| WO | WO 99/37921 | 7/1999 |
| WO | WO 01/06575 | 1/2001 |
| WO | WO 01/06579 | 1/2001 |
| WO | WO 01/59852 | 8/2001 |
| WO | WO 01/09110 | 11/2001 |
| WO | WO 02/37660 | 5/2002 |
| WO | WO 02/37892 | 5/2002 |
| WO | WO 03/056274 | 7/2003 |
| WO | WO 03/056287 | 7/2003 |
| WO | WO 2004/009363 | 1/2004 |
| WO | WO 2004/027970 | 4/2004 |
| WO | WO 2004/053782 | 6/2004 |
| WO | WO 2004/074797 | 9/2004 |
| WO | WO 2004/093763 | 11/2004 |

OTHER PUBLICATIONS

Electrostriction of Polymer Films, by R. Pelrine et al a paper in Micro-Electro-Mechanical Systems, 1997, MEMS '97, Proceeding IEEE 10th Annual International Workshop.*

Electrostriction of polymer Dielectrics with compliant electrodes as a means of actuation, a paper by R. Pelrine et al, in Sensors and Actuators A, Physical vol. 64, 1998, pp. 77-85.*

Electro Polymer Actuators and Devices (EAPAD) by Y. Bar-Cohen, in Proceedings of SPIE—International Society of Optical Engineering, vol. 3987, presented at a conferewnce during Mar. 6-8, 2000.*

Ajiuni, Cheryl, "Pressure Sensors Strive to Stay on Top, New Silicon Micromachining Techniques and Designs Promise Higher Performance", Electronic Design—advanced Technology Series, Oct. 3, 1994, pp. 67-74.

Ashley, S., "Smart Skis and Other Adaptive Structures", Mechanical Engineering, Nov. 1995, pp. 77-81.

Bar-Cohen, Yoseph, JPL. WorldWide ElectroActive Polymers, EAP (Artificial Muscles) Newsletter, vol. 1, No. 1, Jun. 1999.

Cheng, Z.-Y., T.-B. Xu, V. Bharti, S. Wang, and Q. M. Zhang, "Transverse Strain Responses in the Electrostrictive Poly(Vinylidene Fluoride-Trifluorethylene) Copolymer." Appl. Phys. Lett. vol. 74, No. 13, pp. 1901-1903, Mar. 29, 1999.

European Patent Application No. 04716955.2 filed Mar. 3, 2004 in the name of Bonwit et al., Office Action mailed Nov. 26, 2008.

Japanese Application No. 2006-509052 filed Mar. 3, 2004 in the name of Rosenthal, Office Action mailed Nov. 17, 2009.

Kornbluh, R., Pelrine, R., Eckerie, J. Joseph, J., "Electrostrictive Polymer Artificial Muscle Actuators", IEEE International Conference on Robotics and Automation, Leuven, Belgium, May 16-20, 1998, p. 2147-2154 XP-002115803.

Ktech's PVDF Sensors, http://www.ktech.com/pvdf.htm. Jun. 6, 2001, pp. 1-5.

Madden et al., "Conducting polymer actuators as engineering materials." SPIE: Smart Materials and Structures, ed. Yoseph Bar-Cohen. Bellingham, WA, pp. 176-190, Pub 2002.

PCT Patent Application No. PCT/US2004/006518 filed Mar. 3, 2004 in the name of Rosenthal et al., International Preliminary Report on Patentability mailed Sep. 9, 2005.

PCT Patent Application No. PCT/US2004/006518 filed Mar. 3, 2004 in the name of Rosenthal et al., International Search Report and Written Opinion mailed Aug. 25, 2004.

Pei et al., "Electrochemical Applications of the Bending Beam Method. 1, Mass Trasport and Volume Changes in Polypyrrole during Redox," J. Phys. Chem., 1992, 96, pp. 10507-10514.

Pei et al., "Multifunctional Electroelastomer Rolls," Mat. Res. Soc. Symp. Proc. vol. 698, Nov. 26-30, 2001, Boston, MA, pp. 165-170.

Pei, Q. et al., "Multifunctional Electroelastomer Roll Actuators and Their Application for Biomimetic Walking Robots", Smart Structures and Materials 2003, Electroactive Polymer Actuators and Devices, San Diego, CA, USA, Mar. 3-6, 2003, vol. 5051, 2003.

Pei, Q. et al., "Multifunctional Electroelastomer Rolls and Their Application for Biomimetic Walking Robots", Smart Structures and Materials 2002: Industrial and Commercial Applications of Smart Structures Technologies, San Diego, CA USA, Mar. 18-21, 200.

Pei, Q., O. Inganas, and I. Lundstrom, "Bending Bilayer Strips Built From Polyaniline for Artificial Electrochemical Muscles," Smart Materials and Structures, vol. 2, pp. 1-6, Jan. 22, 1993.

Pei, Qibing "Description of Conference Demonstration", Mar. 2001.

Pelrine, R., R. Kornbluh, and G. Kofod, "High Strain Actuator Materials Based on Dielectric Elastomers"; submitted to Advanced Materials (May 2000).

Pelrine, R., R. Kornbluh, and J. Joseph, FY 1996 Final Report on Artificial Muscle for Small Robots, ITAD-7228-FR-97-058, SRI International, Menlo Park, California, 1997.

Pelrine, R., R. Kornbluh, and J. Joseph, FY 1997 Final Report on Artificial Muscle for Small Robots, ITAD-1612-FR-98-041, SRI International, Menlo Park, California, 1998.

Pelrine, R., R, Kornbluh, and J. Joseph, FY 1998 Final Report on Artificial Muscle for Small Robots, ITAD-3482-FR-99-36, SRI International, Menlo Park, California, 1999.

Pelrine, R., R. Kornbluh, and J. Joseph, FY 1999 Final Report on Artificial Muscle for Small Robots, ITAD-10162-FR-00-27, SRI International Menlo Park, California, 2000.

Pelrine, R., R. Kornbluh, Q. Pei, and J. Joseph, "High Speed Electrically Actuated Elastomers with Over 100% Strain," Science, vol. 287, No. 5454, pp. 1-21, 2000.

Pelrine, R., Roy Kornbluh, Jose Joseph, Qibing Pei, Seiki Chiba "Recent Progress in Artificial Muscle Micro Actuators," SRI International, Tokyo, 1999 MITI/NEEDOIMNIC, 1999.

Puers et al. "A Capacitive Pressure Sensor with Low Impedance Output and Active Suppression of Parasitic Effects," Sensors and Actuators, A21-A23 (1990) 108-114.

Puers, Robert, "Capacitive sensors: when and how to use them," Sensors and Actuators A, 37-38 (1993) 93-105.

Treloar, L.R.G., "Mechanics of Rubber Elasticity," J Polymer Science, Polymer Symposium, No. 48, pp. 107-123, 1974.

U.S. Appl. No. 10/154,449, filed May 21, 2002 in the name of Pei et al., Non-final Office Action mailed Feb. 18, 2004.

U.S. Appl. No. 10/154,449, filed May 21, 2002 in the name of Pei et al., Notice of Allowance mailed Jul. 28, 2004.

U.S. Appl. No. 10/793,401, filed Mar. 3, 2004 in the name of Rosenthal et al., Non-final Office Action mailed Dec. 5, 2006.

U.S. Appl. No. 10/793,401, filed Mar. 3, 2004 in the name of Rosenthal et al., Non-final Office Action mailed Feb. 9, 2006.

U.S. Appl. No. 10/793,401, filed Mar. 3, 2004 in the name of Rosenthal et al., Notice of Allowance mailed Feb. 12, 2007.

U.S. Appl. No. 10/793,401, filed Mar. 3, 2004 in the name of Rosenthal et al., Supplemental Notice of Allowance mailed Apr. 11, 2007.

U.S. Appl. No. 10/793,401, filed Mar. 3, 2004 in the name of Rosenthal et al., Supplemental Notice of Allowance mailed Apr. 17, 2007.

U.S. Appl. No. 10/695,976, filed Apr. 3, 2007 in the name of Rosenthal et al., Non-final Office Action mailed Feb. 4, 2009.

U.S. Appl. No. 11/695,976, filed Apr. 3, 2007 in the name of Rosenthal et al., Non-final Office Action mailed May 28, 2009.

U.S. Appl. No. 11/695,976, filed Apr. 3, 2007 in the name of Rosenthal et al., Notice of Allowance mailed Feb. 12, 2010.

Uchino, K. 1986, "Electrostrictive Actuators: Materials and Applications," Ceramic Bulletin, 65(4), pp. 647-652, 1986.

Winters, J, "Muscle as an Actuator for Intelligent Robots," Robotics Research: Trans. Robotics International of SME, Scottsdale, AZ (Aug. 18-21, 1986).

Zhenyi, M., J.I. Scheinbeim, J.W. Lee, and B.A. Newman. 1994. "High Field Electrostrictive Response of Polymers," Journal of Polymer Sciences, Part B-Polymer Physics, vol. 32, pp. 2721-2731, 1994.

* cited by examiner

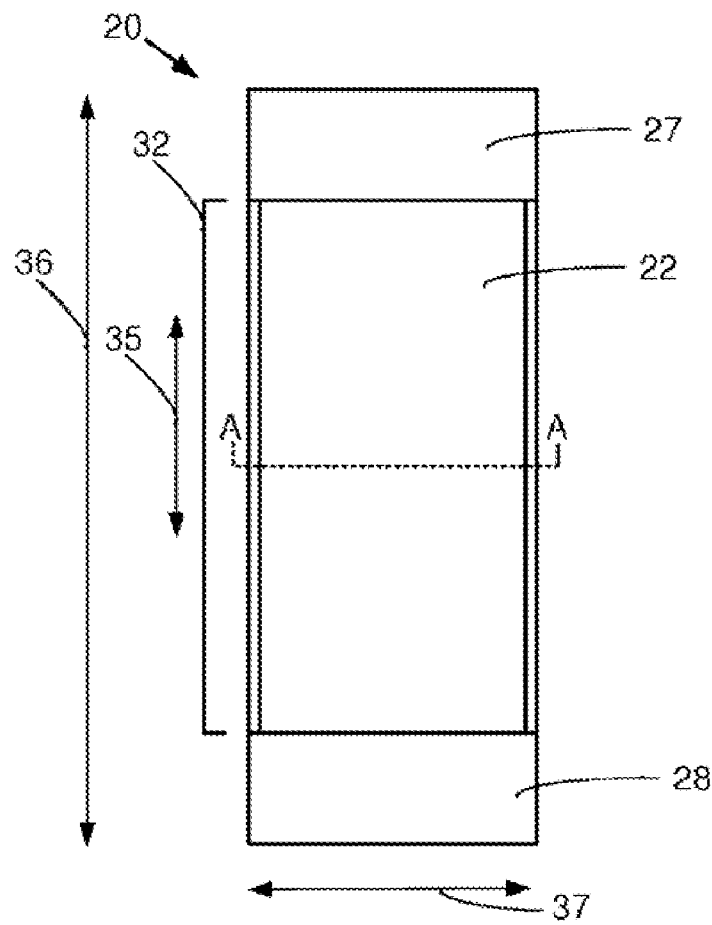
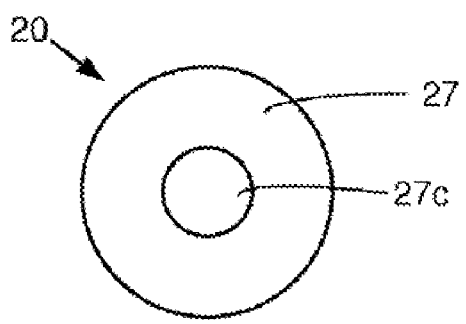
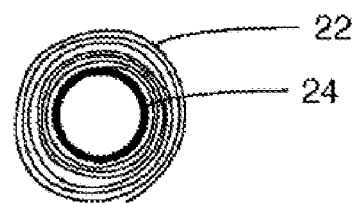
FIG. 2A
FIG. 2B
FIG. 2C

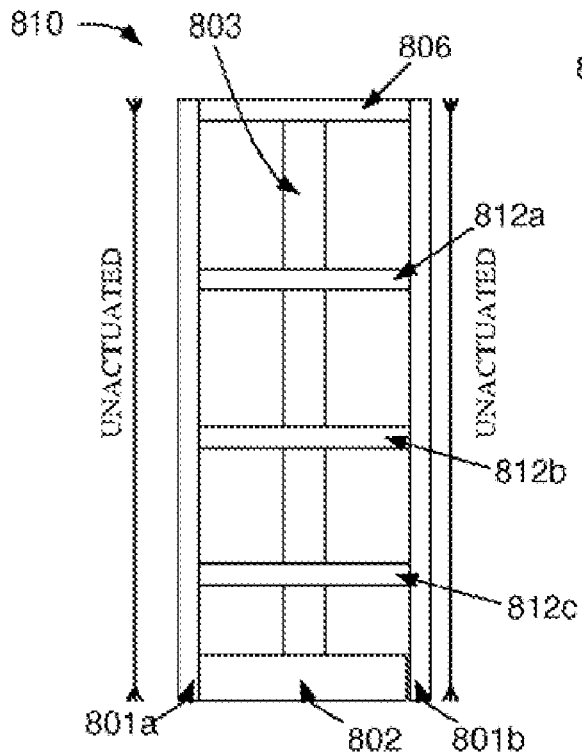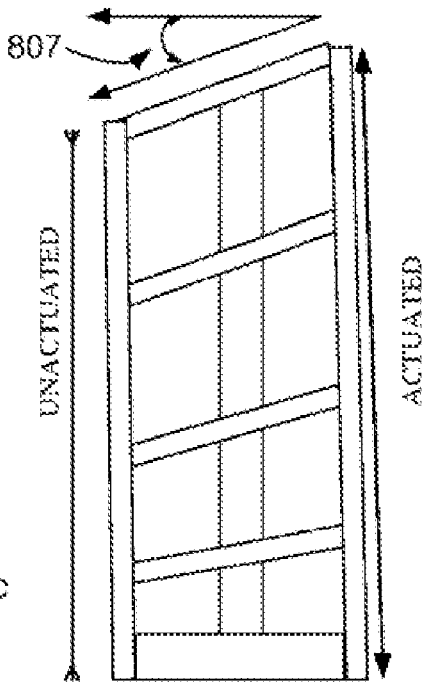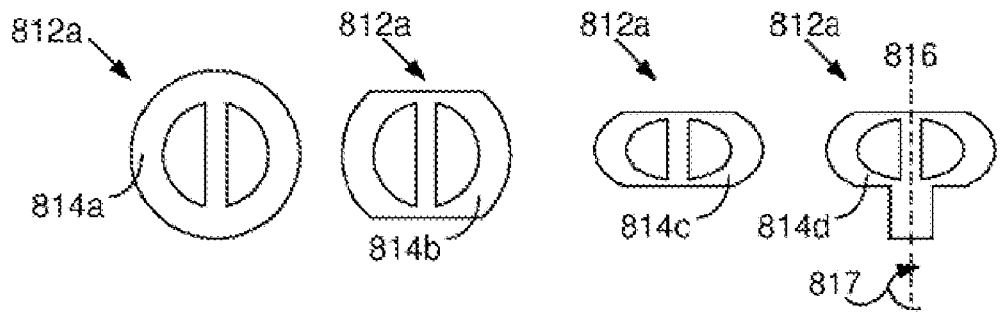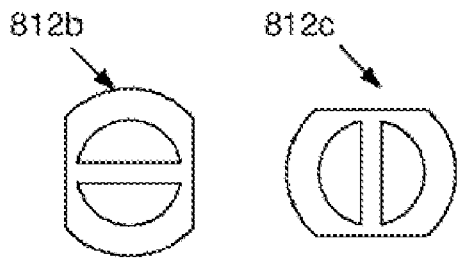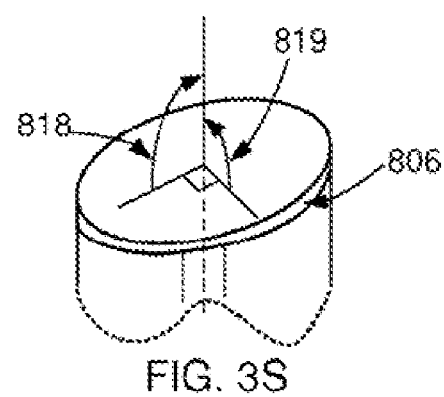
FIG. 3P
FIG. 3Q
FIG. 3Q'
FIG. 3R
FIG. 3S

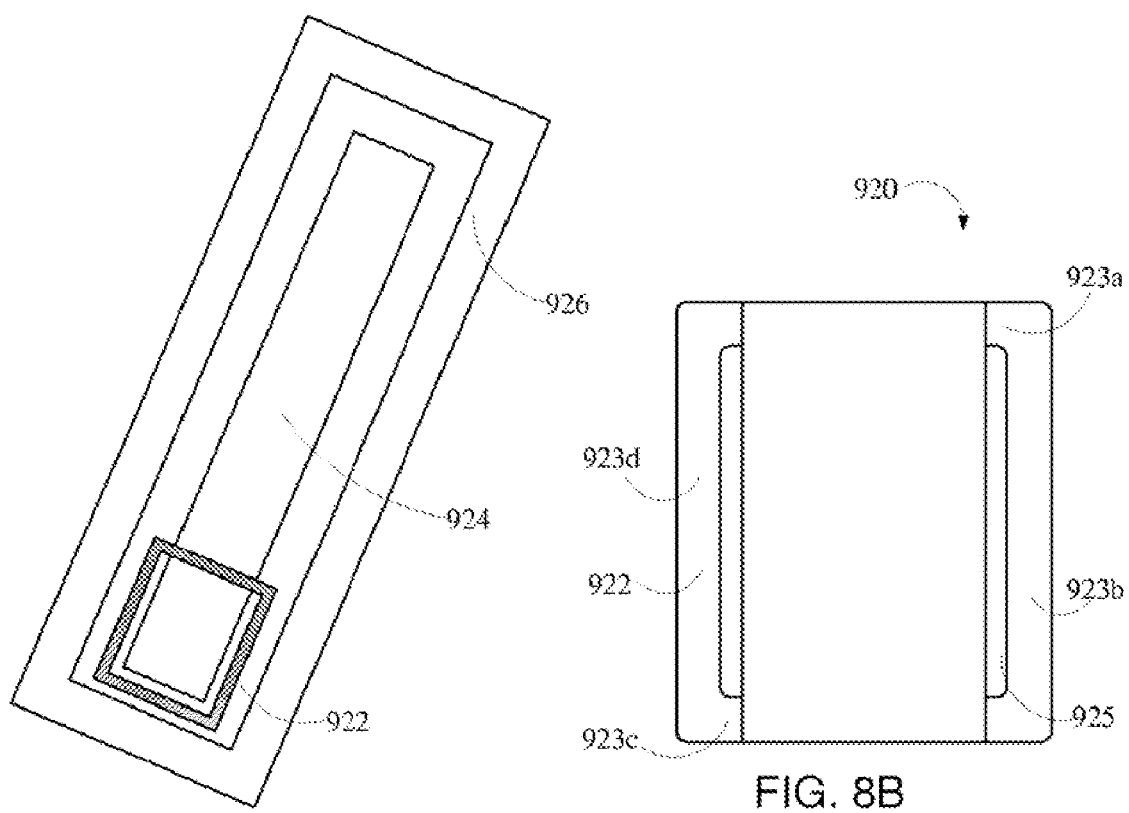
FIG. 8A
FIG. 8B
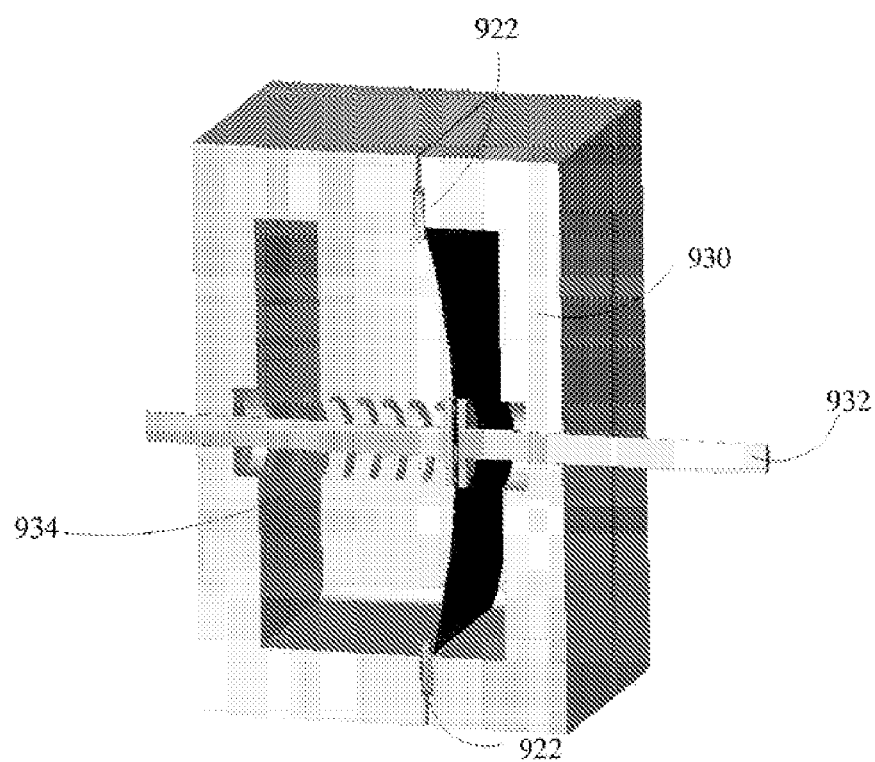
FIG. 8C

METHOD OF FABRICATING AN ELECTROACTIVE POLYMER TRANSDUCER

CROSS-REFERENCE TO RELATED APPLICATIONS

This application is a divisional of U.S. patent application Ser. No. 12/412,032 filed Mar. 26, 2009, which is a divisional of U.S. patent application Ser. No. 11/695,976 filed Apr. 3, 2007, which is a continuation of U.S. patent application Ser. No. 10/793,401 filed Mar. 3, 2004, now U.S. Pat. No. 7,233,097 issued Jun. 19, 2007; U.S. application Ser. No. 10/793,401 claims benefit of priority to U.S. Provisional Patent Application No. 60/451,742 filed Mar. 3, 2003 and is a continuation-in-part of U.S. patent application Ser. No. 10/154,449 filed May 21, 2002, now U.S. Pat. No. 6,891,317 issued May 10, 2005, which claims benefit of priority to U.S. Provisional Patent Application No. 60/293,003 filed on May 22, 2001; each of which is incorporated herein by reference in its entirety for all purposes.

STATEMENT REGARDING FEDERALLY SPONSORED RESEARCH OR DEVELOPMENT

This application was made in part with government support under contract number N00014-00-C-0252 awarded by the Office of Naval Research. The government has certain rights in the invention.

BACKGROUND OF THE INVENTION

The present invention relates generally to electroactive polymer devices that convert between electrical energy and mechanical energy. More particularly, the present invention relates to rolled electroactive polymer devices and methods of fabricating these devices.

In many applications, it is desirable to convert between electrical energy and mechanical energy. Exemplary applications requiring conversion from electrical to mechanical energy include robotics, pumps, speakers, sensors, microfluidics, shoes, general automation, disk drives, and prosthetic devices. These applications include one or more transducers that convert electrical energy into mechanical work—on a macroscopic or microscopic level. Exemplary applications requiring conversion from mechanical to electrical energy include sensors and generators.

New high-performance polymers capable of converting electrical energy to mechanical energy, and vice versa, are now available for a wide range of energy conversion applications. One class of these polymers, electroactive elastomers, is gaining wider attention. Electroactive elastomers may exhibit high energy density, stress, and electromechanical coupling efficiency. The performance of these polymers is notably increased when the polymers are prestrained in area. For example, a 10-fold to 25-fold increase in area significantly improves performance of many electroactive elastomers.

Conventionally, bulky and static frames are used to apply and maintain prestrain for a single layer of electroactive polymer. The frames also allow coupling between the polymer and the external environment. These frames occupy significantly more space and weigh much more than a single polymer layer, and may compromise the energy density and compact advantages that these new polymers provide.

Thus, improved techniques for implementing these high-performance polymers would be desirable.

SUMMARY OF THE INVENTION

The present invention overcomes limitations in the prior art and provides new rolled electroactive polymer devices. The present invention also includes employment of these devices in a wide array of applications and methods for their fabrication. A rolled electroactive polymer device converts between electrical and mechanical energy; and includes a rolled electroactive polymer and at least two electrodes to provide the mechanical/electrical energy conversion. Prestrain may be applied to the polymer. In one embodiment, a rolled electroactive polymer device employs a mechanism, such as a spring, that provides a force to strain the polymer. In one embodiment, the mechanism adds to any prestrain previously established in the polymer. In other cases, no prestrain is previously applied in the polymer and the mechanism establishes prestrain in the polymer. Since prestrain improves mechanical/electrical energy conversion for many electroactive polymers, the mechanism thus improves performance of the rolled electroactive polymer device. In addition, the mechanism may provide other benefits such as a varying force response with deflection, which may be tuned to the needs of an application.

The rolled electroactive polymer transducer may be employed for one or more functions. When a suitable voltage is applied to electrodes in electrical communication with a rolled electroactive polymer, the polymer deflects (actuation). This deflection may be used to do mechanical work. Whether or not the polymer deflects, electrical states imposed on the polymer may be used to vary the stiffness or damping provided by the polymer, which has various mechanical uses. When a previously charged electroactive polymer deflects, the electric field in the material is changed. The change in electric field may be used to produce electrical energy—for generation or sensing purposes. Thus, some functions of use for an electroactive polymer include actuation, variable stiffness or damping, generation or sensing.

Rolled electroactive polymer devices allow for compact electroactive polymer device designs. The rolled devices provide a potentially high electroactive polymer-to-structure weight ratio, and can be configured to actuate in many ways including linear axial extension/contraction, bending, and multi-degree of freedom actuators that combine both extension and bending. Rolled electroactive polymers of the present invention also provide a simple alternative for obtaining multilayer electroactive polymer devices.

In one aspect, the present invention relates to a device for converting between electrical and mechanical energy. The device comprises a transducer comprising at least two electrodes and a rolled electroactive polymer in electrical communication with the at least two electrodes. The device also comprises a mechanism having a first element operably coupled to a first portion of the polymer and a second element operably coupled to a second portion of the polymer. The mechanism provides a force that strains at least a portion of the polymer.

In another aspect, the present invention relates to a method for fabricating an electroactive polymer device. The method comprises disposing at least two electrodes on an electroactive polymer. The method also comprises rolling the electroactive polymer about a spring to produce a rolled electroactive polymer. The method further comprises securing the rolled electroactive polymer to maintain its rolled configuration.

In yet another aspect, the present invention relates to a device for converting between electrical and mechanical energy. The device comprises a transducer comprising at least two electrodes and a rolled electroactive polymer in electrical communication with the at least two electrodes. The device also comprises a spring having a first spring portion operably coupled to a first portion of the polymer and a second spring portion operably coupled to a second portion of the polymer.

Another aspect of the present invention provides a device for converting between electrical and mechanical energy. The device may be generally characterized as comprising: a polymer roll transducer comprising a) an electroactive polymer including at least one active area and b) at least two electrodes in electrical communication with the active area wherein at least a portion of the electroactive polymer is wrapped upon itself to form a roll; at least one support member coupled to the polymer roll transducer for providing at least one of i) a force that strains at least a portion of the polymer, ii) a force for controlling bending in the polymer roll transducer and iii) combinations thereof; and at least one mechanical linkage coupled to the polymer roll transducer for allowing a force or a moment generated in a first portion of the electroactive polymer to be communicated to a second portion of the electroactive polymer.

Yet another aspect of the present invention provides a method for fabricating an electroactive polymer device. The method may be generally characterized as comprising: a) disposing at least two electrodes on an electroactive polymer; b) rolling the electroactive polymer about at least one of a support member, a mechanical linkage, an end cap, a base or combinations thereof to produce an electroactive polymer roll; and c) securing the electroactive polymer roll to maintain its rolled configuration. In a particular embodiment, the electroactive polymer roll may be cut at one or more locations to limit a propagation of a force or a moment from a first portion of the electroactive polymer roll to a second portion of the electroactive polymer roll.

These and other features and advantages of the present invention will be described in the following description of the invention and associated figures.

BRIEF DESCRIPTION OF THE SEVERAL VIEWS OF THE DRAWINGS

FIGS. 2A-2D illustrate a rolled electroactive polymer device in accordance with one embodiment of the present invention.

FIGS. 8A-8C illustrate the fabrication and implementation of a multilayer electroactive polymer device using rolling techniques in accordance with one embodiment of the present invention.

DETAILED DESCRIPTION OF THE INVENTION

The present invention is described in detail with reference to a few preferred embodiments as illustrated in the accompanying drawings. In the following description, numerous specific details are set forth in order to provide a thorough understanding of the present invention. It will be apparent, however, to one skilled in the art, that the present invention may be practiced without some or all of these specific details. In other instances, well known process steps and/or structures have not been described in detail in order to not unnecessarily obscure the present invention.

Electroactive Polymers

Before describing structures, fabrication and applications of rolled electroactive polymers of the present invention, the basic principles of electroactive polymer construction and operation will first be illuminated. The transformation between electrical and mechanical energy in devices of the present invention is based on energy conversion of one or more active areas of an electroactive polymer. Electroactive polymers are capable of converting between mechanical energy and electrical energy. In some cases, an electroactive polymer may change electrical properties (for example, capacitance and resistance) with changing mechanical strain.

Figure 1A:
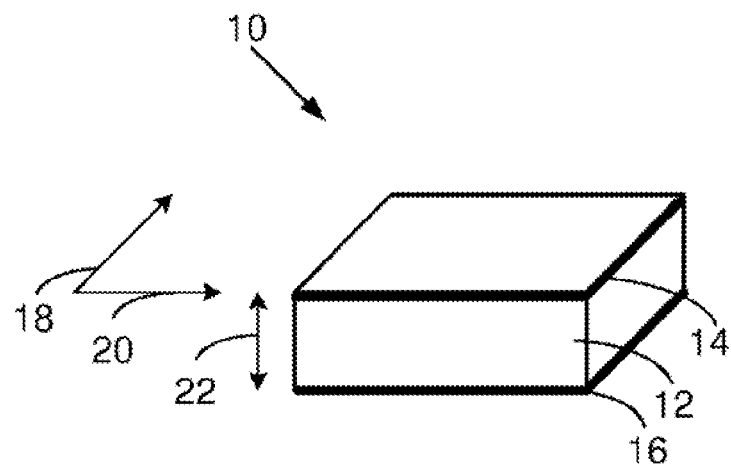
FIGS. 1A and 1B illustrate a top view of a transducer portion before and after application of a voltage, respectively, in accordance with one embodiment of the present invention.

To help illustrate the performance of an electroactive polymer in converting between electrical energy and mechanical energy, FIG. 1A illustrates a top perspective view of a transducer portion 10 in accordance with one embodiment of the present invention. The transducer portion 10 comprises a portion of an electroactive polymer 12 for converting between electrical energy and mechanical energy. In one embodiment, an electroactive polymer refers to a polymer that acts as an insulating dielectric between two electrodes and may deflect upon application of a voltage difference between the two electrodes (a 'dielectric elastomer'). Top and bottom electrodes 14 and 16 are attached to the electroactive polymer 12 on its top and bottom surfaces, respectively, to provide a voltage difference across polymer 12, or to receive electrical energy from the polymer 12. Polymer 12 may deflect with a change in electric field provided by the top and bottom electrodes 14 and 16. Deflection of the transducer portion 10 in response to a change in electric field provided by the electrodes 14 and 16 is referred to as 'actuation'. Actuation typically involves the conversion of electrical energy to mechanical energy. As polymer 12 changes in size, the deflection may be used to produce mechanical work.

Figure 1B:
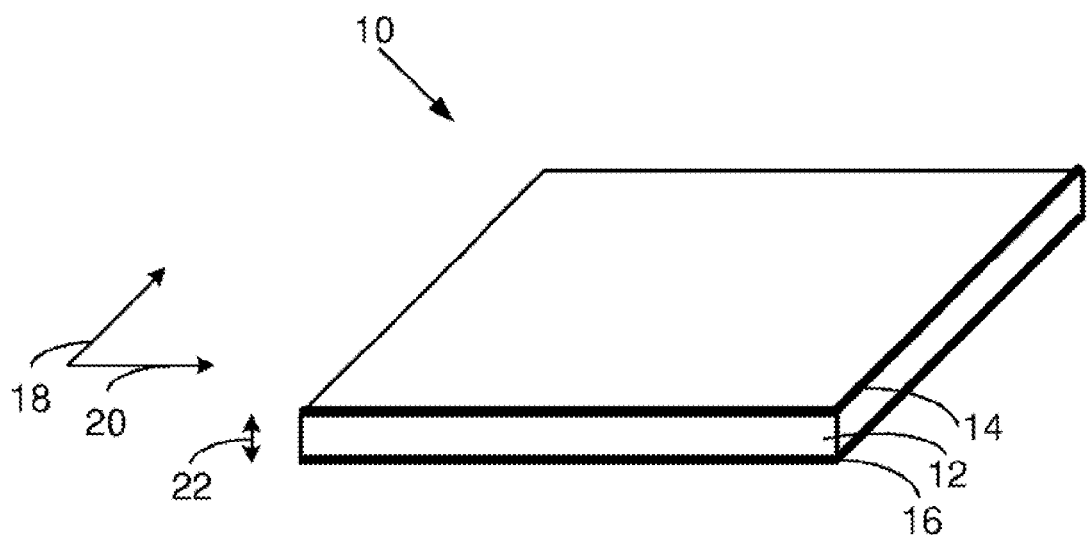

FIG. 1B illustrates a top perspective view of the transducer portion 10 including deflection. In general, deflection refers to any displacement, expansion, contraction, torsion, linear or area strain, or any other deformation of a portion of the polymer 12. For actuation, a change in electric field corresponding to the voltage difference applied to or by the electrodes 14 and 16 produces mechanical pressure within polymer 12. In this case, the unlike electrical charges produced by electrodes 14 and 16 attract each other and provide a compressive force between electrodes 14 and 16 and an expansion force on polymer 12 in planar directions 18 and 20, causing polymer 12 to compress between electrodes 14 and 16 and stretch in the planar directions 18 and 20.

Electrodes 14 and 16 are compliant and change shape with polymer 12. The configuration of polymer 12 and electrodes 14 and 16 provides for increasing polymer 12 response with deflection. More specifically, as the transducer portion 10 deflects, compression of polymer 12 brings the opposite charges of electrodes 14 and 16 closer and the stretching of polymer 12 separates similar charges in each electrode. In one embodiment, one of the electrodes 14 and 16 is ground. For actuation, the transducer portion 10 generally continues to deflect until mechanical forces balance the electrostatic forces driving the deflection. The mechanical forces include elastic restoring forces of the polymer 12 material, the compliance of electrodes 14 and 16, and any external resistance provided by a device and/or load coupled to the transducer portion 10, etc. The deflection of the transducer portion 10 as a result of an applied voltage may also depend on a number of other factors such as the polymer 12 dielectric constant and the size of polymer 12.

Electroactive polymers in accordance with the present invention are capable of deflection in any direction. After application of a voltage between the electrodes 14 and 16, the electroactive polymer 12 increases in size in both planar directions 18 and 20. In some cases, the electroactive polymer 12 is incompressible, e.g. has a substantially constant volume under stress. In this case, the polymer 12 decreases in thickness as a result of the expansion in the planar directions 18 and 20. It should be noted that the present invention is not limited to incompressible polymers and deflection of the polymer 12 may not conform to such a simple relationship.

Application of a relatively large voltage difference between electrodes 14 and 16 on the transducer portion 10 shown in FIG. 1A will cause transducer portion 10 to change to a thinner, larger area shape as shown in FIG. 1B. In this manner, the transducer portion 10 converts electrical energy to mechanical energy. The transducer portion 10 may also be used to convert mechanical energy to electrical energy.

For actuation, the transducer portion 10 generally continues to deflect until mechanical forces balance the electrostatic forces driving the deflection. The mechanical forces include elastic restoring forces of the polymer 12 material, the compliance of electrodes 14 and 16, and any external resistance provided by a device and/or load coupled to the transducer portion 10, etc. The deflection of the transducer portion 10 as a result of an applied voltage may also depend on a number of other factors such as the polymer 12 dielectric constant and the size of polymer 12.

In one embodiment, electroactive polymer 12 is pre-strained. Pre-strain of a polymer may be described, in one or more directions, as the change in dimension in a direction after pre-straining relative to the dimension in that direction before pre-straining. The pre-strain may comprise elastic deformation of polymer 12 and be formed, for example, by stretching the polymer in tension and fixing one or more of the edges while stretched. Alternatively, as will be described in greater detail below, a mechanism such as a spring may be coupled to different portions of an electroactive polymer and provide a force that strains a portion of the polymer. For many polymers, pre-strain improves conversion between electrical and mechanical energy. The improved mechanical response enables greater mechanical work for an electroactive polymer, e.g., larger deflections and actuation pressures. In one embodiment, prestrain improves the dielectric strength of the polymer. In another embodiment, the prestrain is elastic. After actuation, an elastically pre-strained polymer could, in principle, be unfixed and return to its original state.

In one embodiment, pre-strain is applied uniformly over a portion of polymer 12 to produce an isotropic pre-strained polymer. By way of example, an acrylic elastomeric polymer may be stretched by 200 to 400 percent in both planar directions. In another embodiment, pre-strain is applied unequally in different directions for a portion of polymer 12 to produce an anisotropic pre-strained polymer. In this case, polymer 12 may deflect greater in one direction than another when actuated. While not wishing to be bound by theory, it is believed that pre-straining a polymer in one direction may increase the stiffness of the polymer in the pre-strain direction. Correspondingly, the polymer is relatively stiffer in the high pre-strain direction and more compliant in the low pre-strain direction and, upon actuation, more deflection occurs in the low pre-strain direction. In one embodiment, the deflection in direction 18 of transducer portion 10 can be enhanced by exploiting large pre-strain in the perpendicular direction 20. For example, an acrylic elastomeric polymer used as the transducer portion 10 may be stretched by 10 percent in direction 18 and by 500 percent in the perpendicular direction 20. The quantity of pre-strain for a polymer may be based on the polymer material and the desired performance of the polymer in an application. Pre-strain suitable for use with the present invention is further described in commonly owned, copending U.S. patent application Ser. No. 09/619,848, now U.S. Pat. No. 7,034,432, which is incorporated by reference for all purposes.

Generally, after the polymer is pre-strained, it may be fixed to one or more objects or mechanisms. For a rigid object, the object is preferably suitably stiff to maintain the level of pre-strain desired in the polymer. A spring or other suitable mechanism that provides a force to strain the polymer may add to any prestrain previously established in the polymer before attachment to the spring or mechanisms, or may be responsible for all the prestrain in the polymer. The polymer may be fixed to the one or more objects or mechanisms according to any conventional method known in the art such as a chemical adhesive, an adhesive layer or material, mechanical attachment, etc.

Transducers and pre-strained polymers of the present invention are not limited to any particular rolled geometry or type of deflection. For example, the polymer and electrodes may be formed into any geometry or shape including tubes and multi-layer rolls, rolled polymers attached between multiple rigid structures, rolled polymers attached across a frame of any geometry—including curved or complex geometries, across a frame having one or more joints, etc. Deflection of a transducer according to the present invention includes linear expansion and compression in one or more directions, bending, axial deflection when the polymer is rolled, deflection out of a hole provided on an outer cylindrical around the polymer, etc. Deflection of a transducer may be affected by how the polymer is constrained by a frame or rigid structures attached to the polymer.

Materials suitable for use as an electroactive polymer with the present invention may include any substantially insulating polymer or rubber (or combination thereof) that deforms in response to an electrostatic force or whose deformation results in a change in electric field. One suitable material is NuSil CF 19-2186 as provided by NuSil Technology of Carpenteria, Calif. Other exemplary materials suitable for use as a pre-strained polymer include silicone elastomers, acrylic elastomers such as VHB 4910 acrylic elastomer as produced by 3M Corporation of St. Paul, Minn., polyurethanes, thermoplastic elastomers, copolymers comprising PVDF, pressure-sensitive adhesives, fluoroelastomers, polymers comprising silicone and acrylic moieties, and the like. Polymers comprising silicone and acrylic moieties may include copolymers comprising silicone and acrylic moieties, polymer blends comprising a silicone elastomer and an acrylic elastomer, for example. Combinations of some of these materials may also be used as the electroactive polymer in transducers of this invention.

Materials used as an electroactive polymer may be selected based on one or more material properties such as a high electrical breakdown strength, a low modulus of elasticity—(for large or small deformations), a high dielectric constant, etc. In one embodiment, the polymer is selected such that is has an elastic modulus at most about 100 MPa. In another embodiment, the polymer is selected such that is has a maximum actuation pressure between about 0.05 MPa and about 10 MPa, and preferably between about 0.3 MPa and about 3 MPa.

In another embodiment, the polymer is selected such that is has a dielectric constant between about 2 and about 20, and preferably between about 2.5 and about 12.

An electroactive polymer layer in transducers of the present invention may have a wide range of thicknesses. In one embodiment, polymer thickness may range between about 1 micrometer and 2 millimeters. Polymer thickness may be reduced by stretching the film in one or both planar directions. In many cases, electroactive polymers of the present invention may be fabricated and implemented as thin films. Thicknesses suitable for these thin films may be below 50 micrometers.

As electroactive polymers of the present invention may deflect at high strains, electrodes attached to the polymers should also deflect without compromising mechanical or electrical performance. Generally, electrodes suitable for use with the present invention may be of any shape and material provided that they are able to supply a suitable voltage to, or receive a suitable voltage from, an electroactive polymer. The voltage may be either constant or varying over time. In one embodiment, the electrodes adhere to a surface of the polymer. Electrodes adhering to the polymer are preferably compliant and conform to the changing shape of the polymer. Correspondingly, the present invention may include compliant electrodes that conform to the shape of an electroactive polymer to which they are attached. The electrodes may be only applied to a portion of an electroactive polymer and define an active area according to their geometry. Several examples of electrodes that only cover a portion of an electroactive polymer will be described in further detail below.

Various types of electrodes suitable for use with the present invention are described in commonly owned, copending U.S. patent application Ser. No. 09/619,848, now U.S. Pat. No. 7,034,432, which was previously incorporated by reference above. Electrodes described therein and suitable for use with the present invention include structured electrodes comprising metal traces and charge distribution layers, textured electrodes comprising varying out of plane dimensions, conductive greases such as carbon greases or silver greases, colloidal suspensions, high aspect ratio conductive materials such as carbon fibrils and carbon nanotubes, and mixtures of ionically conductive materials.

Materials used for electrodes of the present invention may vary. Suitable materials used in an electrode may include graphite, carbon black, colloidal suspensions, thin metals including silver and gold, silver filled and carbon filled gels and polymers, and ionically or electronically conductive polymers. In a specific embodiment, an electrode suitable for use with the present invention comprises 80 percent carbon grease and 20 percent carbon black in a silicone rubber binder such as Stockwell RTV60-CON as produced by Stockwell Rubber Co. Inc. of Philadelphia, Pa. The carbon grease is of the type such as NyoGel 756G as provided by Nye Lubricant Inc. of Fairhaven, Mass. The conductive grease may also be mixed with an elastomer, such as silicon elastomer RTV 118 as produced by General Electric of Waterford, N.Y., to provide a gel-like conductive grease.

It is understood that certain electrode materials may work well with particular polymers and may not work as well for others. By way of example, carbon fibrils work well with acrylic elastomer polymers while not as well with silicone polymers. For most transducers, desirable properties for the compliant electrode may include one or more of the following: low modulus of elasticity, low mechanical damping, low surface resistivity, uniform resistivity, chemical and environmental stability, chemical compatibility with the electroactive polymer, good adherence to the electroactive polymer, and the ability to form smooth surfaces. In some cases, a transducer of the present invention may implement two different types of electrodes, e.g. a different electrode type for each active area or different electrode types on opposing sides of a polymer.

Rolled Electroactive Polymer Devices

Figure 2D:
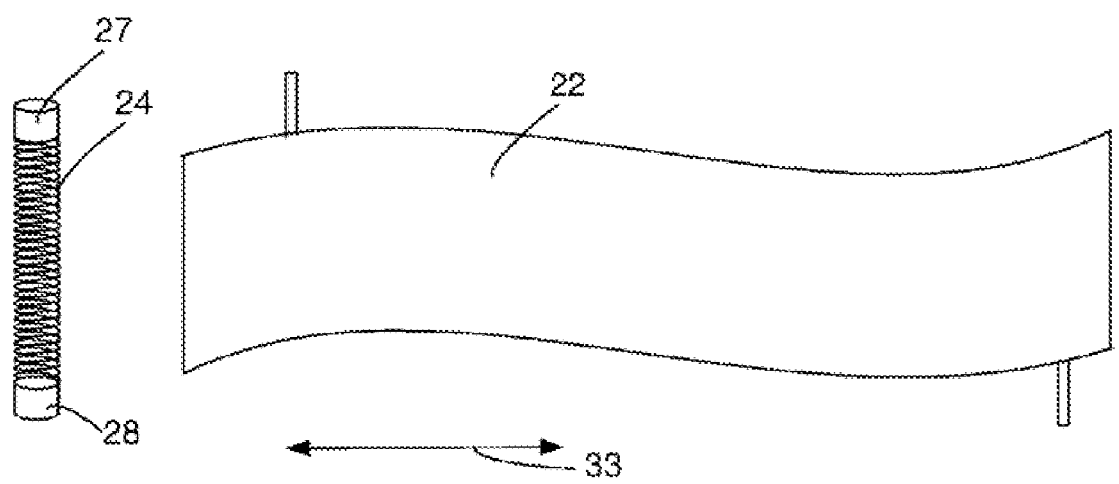

FIGS. 2A-2D show a rolled electroactive polymer device 20 in accordance with one embodiment of the present invention. FIG. 2A illustrates a side view of device 20. FIG. 2B illustrates an axial view of device 20 from the top end. FIG. 2C illustrates an axial view of device 20 taken through cross section A-A. FIG. 2D illustrates components of device 20 before rolling. Device 20 comprises a rolled electroactive polymer 22, spring 24, end pieces 27 and 28, and various fabrication components used to hold device 20 together.

As illustrated in FIG. 2C, electroactive polymer 22 is rolled. In one embodiment, a rolled electroactive polymer refers to an electroactive polymer with, or without electrodes, wrapped round and round onto itself (e.g., like a poster) or wrapped around another object (e.g., spring 24). The polymer may be wound repeatedly and at the very least comprises an outer layer portion of the polymer overlapping at least an inner layer portion of the polymer.

In one embodiment, a rolled electroactive polymer refers to a spirally wound electroactive polymer wrapped around an object or center. As the term is used herein, rolled is independent of how the polymer achieves its rolled configuration.

As illustrated by FIGS. 2C and 2D, electroactive polymer 22 is rolled around the outside of spring 24. Spring 24 provides a force that strains at least a portion of polymer 22. The top end 24a of spring 24 is attached to rigid endpiece 27. Likewise, the bottom end 24b of spring 24 is attached to rigid endpiece 28. The top edge 22a of polymer 22 (FIG. 2D) is wound about endpiece 27 and attached thereto using a suitable adhesive. The bottom edge 22b of polymer 22 is wound about endpiece 28 and attached thereto using an adhesive. Thus, the top end 24a of spring 24 is operably coupled to the top edge 22a of polymer 22 in that deflection of top end 24a corresponds to deflection of the top edge 22a of polymer 22. Likewise, the bottom end 24b of spring 24 is operably coupled to the bottom edge 22b of polymer 22 and deflection bottom end 24b corresponds to deflection of the bottom edge 22b of polymer 22. Polymer 22 and spring 24 are capable of deflection between their respective bottom top portions.

As mentioned above, many electroactive polymers perform better when prestrained. For example, some polymers exhibit a higher breakdown electric field strength, electrically actuated strain, and energy density when prestrained. Spring 24 of device 20 provides forces that result in both circumferential and axial prestrain onto polymer 22.

Spring 24 is a compression spring that provides an outward force in opposing axial directions (FIG. 2A) that axially stretches polymer 22 and strains polymer 22 in an axial direction. Thus, spring 24 holds polymer 22 in tension in axial direction 35. In one embodiment, polymer 22 has an axial prestrain in direction 35 from about 50 to about 300 percent. As will be described in further detail below for fabrication, device 20 may be fabricated by rolling a prestrained electroactive polymer film around spring 24 while it the spring is compressed. Once released, spring 24 holds the polymer 22 in tensile strain to achieve axial prestrain.

Spring 24 also maintains circumferential prestrain on polymer 22. The prestrain may be established in polymer 22 longitudinally in direction 33 (FIG. 2D) before the polymer is rolled about spring 24. Techniques to establish prestrain in this direction during fabrication will be described in greater detail below. Fixing or securing the polymer after rolling, along with the substantially constant outer dimensions for spring 24, maintains the circumferential prestrain about spring 24. In one embodiment, polymer 22 has a circumferential prestrain from about 100 to about 500 percent. In many cases, spring 24 provides forces that result in anisotropic prestrain on polymer 22.

Figure 2E:
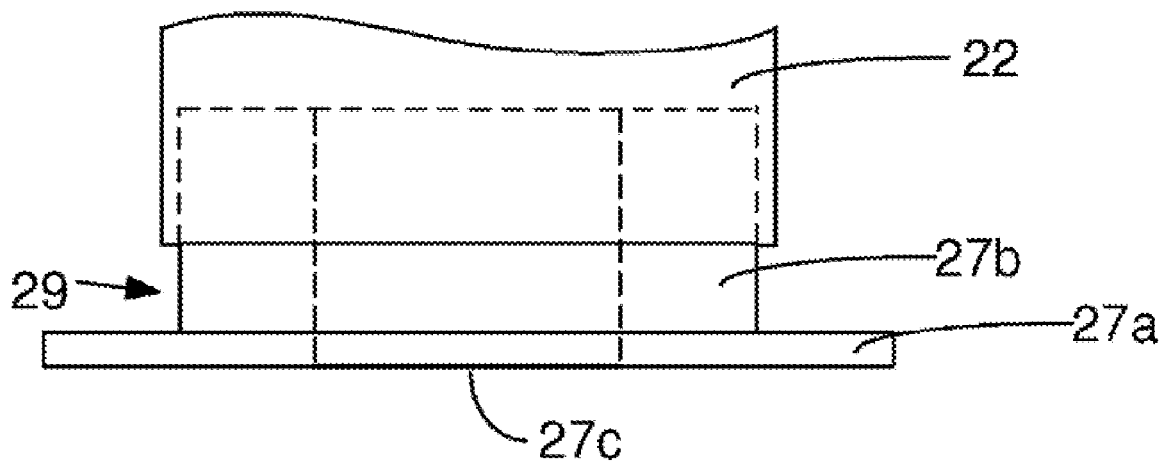
FIG. 2E illustrates an end piece for the rolled electroactive polymer device of FIG. 2A in accordance with one embodiment of the present invention.

End pieces 27 and 28 are attached to opposite ends of rolled electroactive polymer 22 and spring 24. FIG. 2E illustrates a side view of end piece 27 in accordance with one embodiment of the present invention. Endpiece 27 is a circular structure that comprises an outer flange 27a, an interface portion 27b, and an inner hole 27c. Interface portion 27b preferably has the same outer diameter as spring 24. The edges of interface portion 27b may also be rounded to prevent polymer damage. Inner hole 27c is circular and passes through the center of endpiece 27, from the top end to the bottom outer end that includes outer flange 27a. In a specific embodiment, endpiece 27 comprises aluminum, magnesium or another machine metal. Inner hole 27c is defined by a hole machined or similarly fabricated within endpiece 27. In a specific embodiment, endpiece 27 comprises ½ inch end caps with a ⅜ inch inner hole 27c.

In one embodiment, polymer 22 does not extend all the way to outer flange 27a and a gap 29 is left between the outer portion edge of polymer 22 and the inside surface of outer flange 27a. As will be described in further detail below, an adhesive or glue may be added to the rolled electroactive polymer device to maintain its rolled configuration. Gap 29 provides a dedicated space on endpiece 27 for an adhesive or glue than the buildup to the outer diameter of the rolled device and fix to all polymer layers in the roll to endpiece 27. In a specific embodiment, gap 29 is between about 0 mm and about 5 mm.

The portions of electroactive polymer 22 and spring 24 between end pieces 27 and 28 may be considered active to their functional purposes. Thus, end pieces 27 and 28 define an active region 32 of device 20 (FIG. 2A). End pieces 27 and 28 provide a common structure for attachment with spring 24 and with polymer 22. In addition, each end piece 27 and 28 permits external mechanical and detachable coupling to device 20. For example, device 20 may be employed in a robotic application where endpiece 27 is attached to an upstream link in a robot and endpiece 28 is attached to a downstream link in the robot. Actuation of electroactive polymer 22 then moves the downstream link relative to the upstream link as determined by the degree of freedom between the two links (e.g., rotation of link 2 about a pin joint on link 1).

In a specific embodiment, inner hole 27c comprises an internal thread capable of threaded interface with a threaded member, such as a screw or threaded bolt. The internal thread permits detachable mechanical attachment to one end of device 20. For example, a screw may be threaded into the internal thread within end piece 27 for external attachment to a robotic element. For detachable mechanical attachment internal to device 20, a nut or bolt to be threaded into each end piece 27 and 28 and pass through the axial core of spring 24, thereby fixing the two end pieces 27 and 28 to each other. This allows device 20 to be held in any state of deflection, such as a fully compressed state useful during rolling. This may also be useful during storage of device 20 so that polymer 22 is not strained in storage.

In one embodiment, a stiff member or linear guide 30 is disposed within the spring core of spring 24. Since the polymer 22 in spring 24 is substantially compliant between end pieces 27 and 28, device 20 allows for both axial deflection along direction 35 and bending of polymer 22 and spring 24 away from its linear axis (the axis passing through the center of spring 24). In some embodiments, only axial deflection is desired. Linear guide 30 prevents bending of device 20 between end pieces 27 and 28 about the linear axis. Preferably, linear guide 30 does not interfere with the axial deflection of device 20. For example, linear guide 30 preferably does not introduce frictional resistance between itself and any portion of spring 24. With linear guide 30, or any other suitable constraint that prevents motion outside of axial direction 35, device 20 may act as a linear actuator or generator with output strictly in direction 35. Linear guide 30 may be comprised of any suitably stiff material such as wood, plastic, metal, etc.

Polymer 22 is wound repeatedly about spring 22. For single electroactive polymer layer construction, a rolled electroactive polymer of the present invention may comprise between about 2 and about 200 layers. In this case, a layer refers to the number of polymer films or sheets encountered in a radial cross-section of a rolled polymer. In some cases, a rolled polymer comprises between about 5 and about 100 layers. In a specific embodiment, a rolled electroactive polymer comprises between about 15 and about 50 layers.

In another embodiment, a rolled electroactive polymer employs a multilayer structure. The multilayer structure comprises multiple polymer layers disposed on each other before rolling or winding. For example, a second electroactive polymer layer, without electrodes patterned thereon, may be disposed on an electroactive polymer having electrodes patterned on both sides. The electrode immediately between the two polymers services both polymer surfaces in immediate contact. After rolling, the electrode on the bottom side of the electroded polymer then contacts the top side of the non-electroded polymer. In this manner, the second electroactive polymer with no electrodes patterned thereon uses the two electrodes on the first electroded polymer.

Other multilayer constructions are possible. For example, a multilayer construction may comprise any even number of polymer layers in which the odd number polymer layers are electroded and the even number polymer layers are not. The upper surface of the top non-electroded polymer then relies on the electrode on the bottom of the stack after rolling. Multilayer constructions having 2, 4, 6, 8, etc., are possible this technique. In some cases, the number of layers used in a multilayer construction may be limited by the dimensions of the roll and thickness of polymer layers. As the roll radius decreases, the number of permissible layers typically decrease is well. Regardless of the number of layers used, the rolled transducer is configured such that a given polarity electrode does not touch an electrode of opposite polarity. In one embodiment, multiple layers are each individually electroded and every other polymer layer is flipped before rolling such that electrodes in contact each other after rolling are of a similar voltage or polarity.

The multilayer polymer stack may also comprise more than one type of polymer For example, one or more layers of a second polymer may be used to modify the elasticity or stiffness of the rolled electroactive polymer layers. This polymer may or may not be active in the charging/discharging during the actuation. When a non-active polymer layer is employed, the number of polymer layers may be odd. The second polymer may also be another type of electroactive polymer that varies the performance of the rolled product.

In one embodiment, the outermost layer of a rolled electroactive polymer does not comprise an electrode disposed thereon. This may be done to provide a layer of mechanical protection, or to electrically isolate electrodes on the next inner layer.

Device 20 provides a compact electroactive polymer device structure and improves overall electroactive polymer device performance over conventional electroactive polymer devices. For example, the multilayer structure of device 20 modulates the overall spring constant of the device relative to each of the individual polymer layers. In addition, the increased stiffness of the device achieved via spring 24 increases the stiffness of device 20 and allows for faster response in actuation, if desired.

In a specific embodiment, spring 24 is a compression spring such as catalog number 11422 as provided by Century Spring of Los Angeles, Calif. This spring is characterized by a spring force of 0.91 lb/inch and dimensions of 4.38 inch free length, 1.17 inch solid length, 0.360 inch outside diameter, 0.3 inch inside diameter. In this case, rolled electroactive polymer device 20 has a height 36 from about 5 to about 7 cm, a diameter 37 of about 0.8 to about 1.2 cm, and an active region between end pieces of about 4 to about 5 cm. The polymer is characterized by a circumferential prestrain from about 300 to about 500 percent and axial prestrain (including force contributions by spring 24) from about 150 to about 250 percent.

Device 20 has many functional uses. As will be described in further detail below, electroactive polymers of the present invention may be used for actuation, generation, sensing, variable stiffness and damping, or combinations thereof. Thus, device 20 may be used in robotic application for actuation and production of mechanical energy. Alternatively, rolled device 20 may contribute to stiffness and damping control of a robotic link. Thus, either end piece 27 or 28 may be coupled to a potentially moving mechanical link to receive mechanical energy from the link and damp the motion. In this case, polymer 22 converts this mechanical energy to electrical energy according to techniques described below.

Although device 20 is illustrated with a single spring 24 disposed internal to the rolled polymer, it is understood that additional structures such as another spring external to the polymer may also be used to provide strain and prestrain forces. These external structures may be attached to device 20 using end pieces 27 and 28 for example.

The present invention also encompasses mechanisms, other than a spring, used in a rolled electroactive polymer device to apply a force that strains a rolled polymer. As the term is used herein, a mechanism used to provide strain onto a rolled electroactive polymer generally refers to a system or an arrangement of elements that are capable of providing a force to different portions of a rolled electroactive polymer. In many cases, the mechanism is flexible (e.g., a spring) or has moving parts (e.g., a pneumatic cylinder). The mechanism may also comprises rigid parts (see the frame of FIG. 8B). Strain may also be achieved using mechanisms such as hydraulic actuators, pneumatic actuators, and magnetic systems (e.g., FIG. 3K), for example. Alternatively, compressible materials and foams may be disposed internal to the roll to provide the strain forces and allow for axial deflection.

Generally, the mechanism provides a force that onto the polymer. In one embodiment, the force changes the force vs. deflection characteristics of the device, such as to provide a negative force response, as described below. In another embodiment, the force strains the polymer. This latter case implies that the polymer deflects in response to the force, relative to its deflection state without the effects of the mechanism. This strain may include prestrain as described above. In one embodiment, the mechanism maintains or adds to any prestrain previously established in the polymer, such prestrain provided by a fixture during rolling as described below. In another embodiment, no prestrain is previously applied in the polymer and the mechanism establishes prestrain in the polymer.

In one embodiment, the mechanism is another elastomer that is similar or different from the electroactive polymer. For example, this second elastomer may be disposed as a nearly-solid rubber core that is axially compressed before rolling (to provide an axial tensile prestrain on the electroactive polymer). The elastomer core can have a thin hole for a rigid rod to facilitate the rolling process. If lubricated, the rigid rod may be slid out from the roll after fabrication. One may also make a solid elastomer roll tightly wound with electroactive polymer using a similar technique.

Figure 3A:
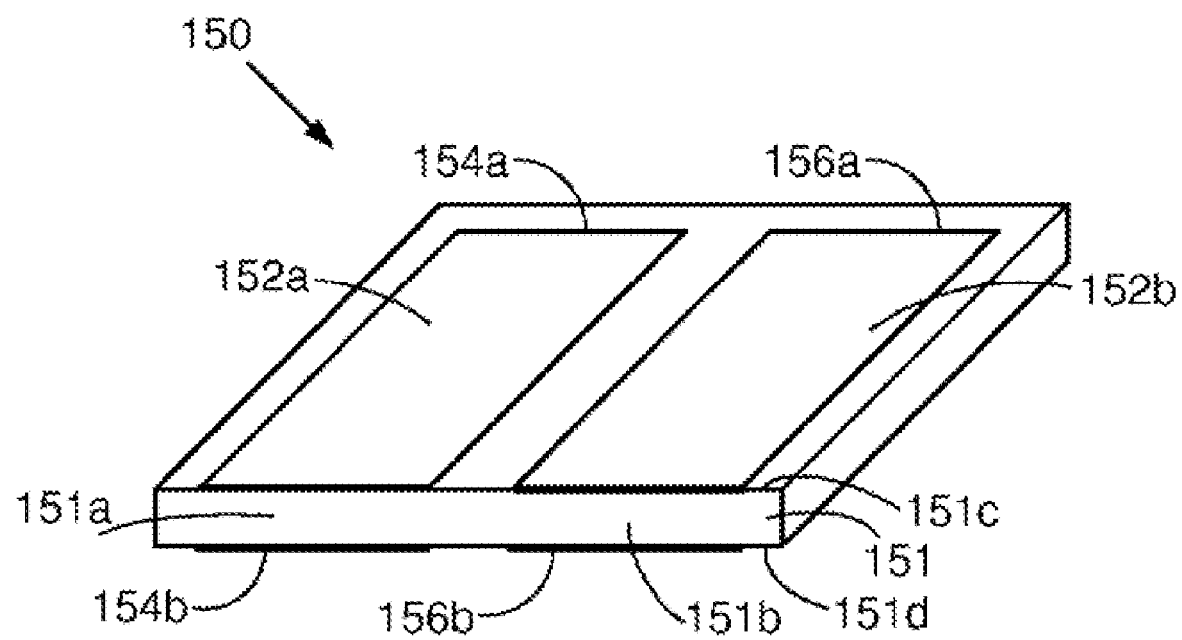
FIG. 3A illustrates a monolithic transducer comprising a plurality of active areas on a single polymer in accordance with one embodiment of the present invention.

The mechanism and its constituent elements are typically operably coupled to the polymer such that the strain is achieved. This may include fixed or detachable coupling, permanent attachment, etc. In the case of the spring above, operable coupling includes the use of an adhesive, such as glue, that attaches opposite ends of the spring to opposite ends of the polymer. An adhesive is also used to attach the rolled polymer to the frame in FIG. 8B. The coupling may be direct or indirect, e.g., the magnet 252 of FIG. 3K is attached to the end piece 242, which is attached to the rolled polymer. One of skill in the art is aware of numerous techniques to couple or attach two mechanical structures together, and these techniques are not expansively discussed herein for sake of brevity.

Rolled electroactive polymers of the present invention have numerous advantages. Firstly, these designs provide a multilayer device without having to individually frame each layer; and stack numerous frames (see FIG. 8B). In addition, the cylindrical package provided by these devices is advantageous to some applications where long and cylindrical packaging is advantageous over flat packaging associated with planar electroactive polymer devices. In addition, using a larger number of polymer layers in a roll improves reliability of the device and reduces sensitivity to imperfections and local cracks in any individual polymer layer.

Alternate Rolled Electroactive Polymer Device Designs
Multiple Active Areas

In some cases, electrodes cover a limited portion of an electroactive polymer relative to the total area of the polymer. This may be done to prevent electrical breakdown around the edge of a polymer, to allow for polymer portions to facilitate a rolled construction (e.g., an outside polymer barrier layer), to provide multifunctionality, or to achieve customized deflections for one or more portions of the polymer. As the term is used herein, an active area is defined as a portion of a transducer comprising a portion of an electroactive polymer and one or more electrodes that provide or receive electrical energy to or from the portion. The active area may be used for any of the functions described below. For actuation, the active area includes a portion of polymer having sufficient electrostatic force to enable deflection of the portion. For generation or sensing, the active area includes a portion of polymer having sufficient deflection to enable a change in electrostatic energy. A polymer of the present invention may have multiple active areas.

In accordance with the present invention, the term "monolithic" is used herein to refer to electroactive polymers and transducers comprising a plurality of active areas on a single polymer. FIG. 3A illustrates a monolithic transducer 150 comprising a plurality of active areas on a single polymer 151 in accordance with one embodiment of the present invention. The monolithic transducer 150 converts between electrical energy and mechanical energy. The monolithic transducer 150 comprises an electroactive polymer 151 having two active areas 152a and 152b. Polymer 151 may be held in place using, for example, a rigid frame (not shown) attached at the edges of the polymer. Coupled to active areas 152a and 152b are wires 153 that allow electrical communication between active areas 152a and 152b and allow electrical communication with communication electronics 155.

Active area 152a has top and bottom electrodes 154a and 154b that are attached to polymer 151 on its top and bottom surfaces 151c and 151d, respectively. Electrodes 154a and 154b provide or receive electrical energy across a portion 151a of the polymer 151. Portion 151a may deflect with a change in electric field provided by the electrodes 154a and 154b. For actuation, portion 151a comprises the polymer 151 between the electrodes 154a and 154b and any other portions of the polymer 151 having sufficient electrostatic force to enable deflection upon application of voltages using the electrodes 154a and 154b. When active area 152a is used as a generator to convert from electrical energy to mechanical energy, deflection of the portion 151a causes a change in electric field in the portion 151a that is received as a change in voltage difference by the electrodes 154a and 154b.

Active area 152b has top and bottom electrodes 156a and 156b that are attached to the polymer 151 on its top and bottom surfaces 151c and 151d, respectively. Electrodes 156a and 156b provide or receive electrical energy across a portion 151 b of the polymer 151. Portion 151b may deflect with a change in electric field provided by the electrodes 156a and 156b. For actuation, portion 151b comprises the polymer 151 between the electrodes 156a and 156b and any other portions of the polymer 151 having sufficient stress induced by the electrostatic force to enable deflection upon application of voltages using the electrodes 156a and 156b. When active area 152b is used as a generator to convert from electrical energy to mechanical energy, deflection of the portion 151b causes a change in electric field in the portion 151b that is received as a change in voltage difference by the electrodes 156a and 156b.

Active areas for an electroactive polymer may be easily patterned and configured using conventional electroactive polymer electrode fabrication techniques. Multiple active area polymers and transducers are further described in Ser. No. 09/779,203 now U.S. Pat. No. 6,664,718, each of which is incorporated herein by reference for all purposes. Given the ability to pattern and independently control multiple active areas allows rolled transducers of the present invention to be employed in many new applications; as well as employed in existing applications in new ways.

Figure 3B:
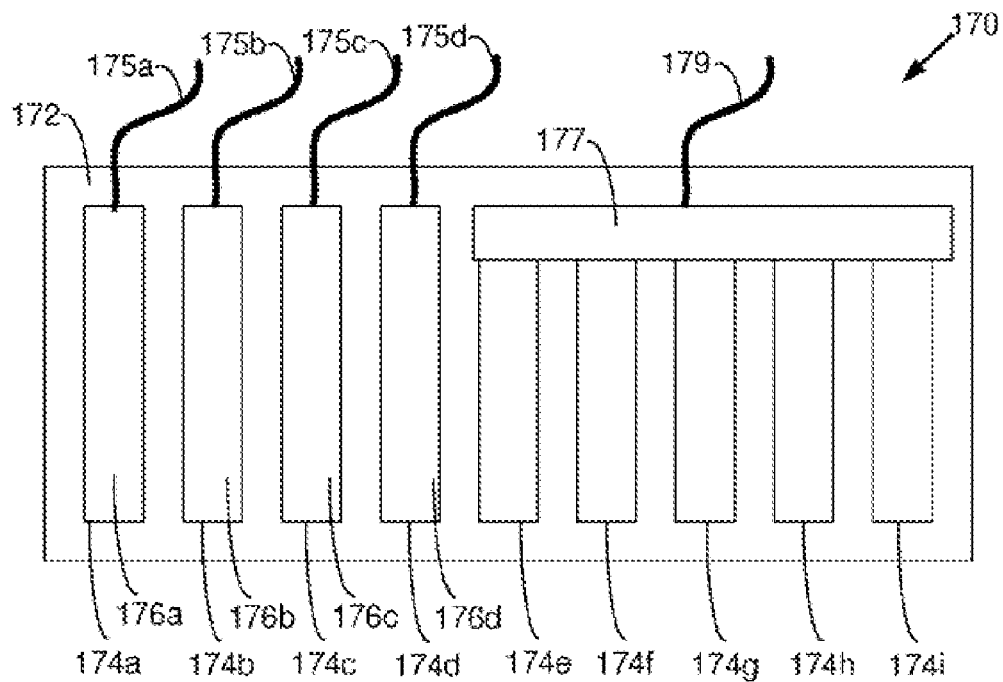
FIG. 3B illustrates a monolithic transducer comprising a plurality of active areas on a single polymer, before rolling, in accordance with one embodiment of the present invention.

FIG. 3B illustrates a monolithic transducer 170 comprising a plurality of active areas on a single polymer 172, before rolling, in accordance with one embodiment of the present invention. Transducer 170 comprises individual electrodes 174 on the facing polymer side 177. The opposite side of polymer 172 (not shown) may include individual electrodes that correspond in location to electrodes 174, or may include a common electrode that spans in area and services multiple or all electrodes 174 and simplifies electrical communication. Active areas 176 then comprise portions of polymer 172 between each individual electrode 174 and the electrode on the opposite side of polymer 172, as determined by the mode of operation of the active area. For actuation for example, active area 176a for electrode 174a includes a portion of polymer 172 having sufficient electrostatic force to enable deflection of the portion, as described above.

Active areas 176 on transducer 170 may be configured for one or more functions. In one embodiment, all active areas 176 are all configured for actuation. In another embodiment suitable for use with robotic applications, one or two active areas 176 are configured for sensing while the remaining active areas 176 are configured for actuation. In this manner, a rolled electroactive polymer device using transducer 170 is capable of both actuation and sensing. Any active areas designated for sensing may each include dedicated wiring to sensing electronics, as described below.

At shown, electrodes 174a-d each include a wire 175a-d attached thereto that provides dedicated external electrical communication and permits individual control for each active area 176a-d. Electrodes 174e-i are all electrical communication with common electrode 177 and wire 179 that provides common electrical communication with active areas 176e-i. Common electrode 177 simplifies electrical communication with multiple active areas of a rolled electroactive polymer that are employed to operate in a similar manner. In one embodiment, common electrode 177 comprises aluminum foil disposed on polymer 172 before rolling. In one embodiment, common electrode 177 is a patterned electrode of similar material to that used for electrodes 174a-i, e.g., carbon grease.

For example, a set of active areas may be employed for one or more of actuation, generation, sensing, changing the stiffness and/or damping, or a combination thereof. Suitable electrical control also allows a single active area to be used for more than one function. For example, active area 174a may be used for actuation and variable stiffness control of a robotic limb in a robotics application. The same active area may also be used for generation to produce electrical energy based on motion of the robotic limb. Suitable electronics for each of these functions are described in further detail below. Active area 174b may also be flexibly used for actuation, generation, sensing, changing stiffness, or a combination thereof. Energy generated by one active area may be provided to another active area, if desired by an application. Thus, rolled polymers and transducers of the present invention may include active areas used as an actuator to convert from electrical to mechanical energy, a generator to convert from mechanical to electrical energy, a sensor that detects a parameter, or a variable stiffness and/or damping device that is used to control stiffness and/or damping, or combinations thereof.

In one embodiment, multiple active areas employed for actuation are wired in groups to provide graduated electrical control of force and/or deflection output from a rolled electroactive polymer device. For example, a rolled electroactive polymer transducer many have 50 active areas in which 20 active areas are coupled to one common electrode, 10 active areas to a second common electrode, another 10 active areas to a third common electrode, 5 active areas to a fourth common electrode in the remaining five individually wired. Suitable computer management and on-off control for each common electrode then allows graduated force and deflection control for the rolled transducer using only binary on/off switching. The biological analogy of this system is motor units found in many mammalian muscular control systems. Obviously, any number of active areas and common electrodes may be implemented in this manner to provide a suitable mechanical output or graduated control system.

Multiple Degree of Freedom Rolled Devices

In another embodiment, multiple active areas on an electroactive polymer are disposed such subsets of the active areas radially align after rolling. For example, the multiple the active areas may be disposed such that, after rolling, active areas are disposed every 90 degrees in the roll. These radially aligned electrodes may then be actuated in unity to allow multiple degree of freedom motion for a rolled electroactive polymer device.

Figures 3C, 3D:
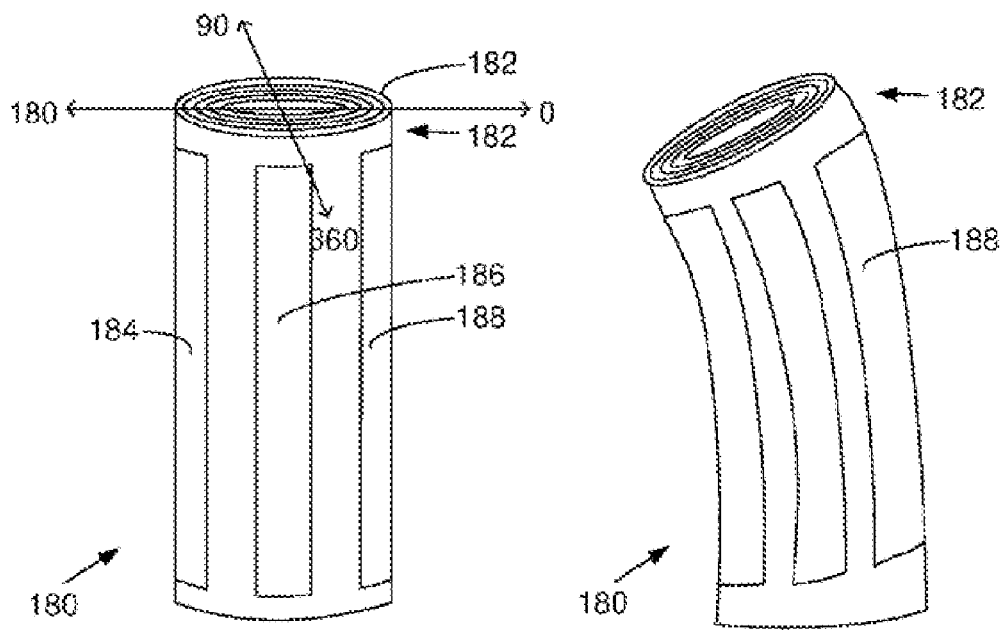
FIG. 3C illustrates a rolled transducer that produces two-dimensional output in accordance with one environment of the present invention.
FIG. 3D illustrates the rolled transducer of FIG. 3C with actuation for one set of radially aligned active areas.

FIG. 3C illustrates a rolled transducer 180 capable of two-dimensional output in accordance with one environment of the present invention. Transducer 180 comprises an electroactive polymer 182 rolled to provide ten layers. Each layer comprises four radially aligned active areas. The center of each active area is disposed at a 90 degree increment relative to its neighbor. FIG. 3C shows the outermost layer of polymer 182 and radially aligned active areas 184, 186, and 188, which are disposed such that their centers mark 90 degree increments relative to each other. A fourth radially aligned active area (not shown) on the backside of polymer 182 has a center approximately situated 180 degrees from radially aligned active area 186.

Radially aligned active area 184 may include common electrical communication with active areas on inner polymer layers having the same radial alignment. Likewise, the other three radially aligned outer active areas 182, 186, and the back active area not shown, may include common electrical communication with their inner layer counterparts. In one embodiment, transducer 180 comprises four leads that provide common actuation for each of the four radially aligned active area sets.

FIG. 3D illustrates transducer 180 with radially aligned active area 188, and its corresponding radially aligned inner layer active areas, actuated. Actuation of active area 188, and corresponding inner layer active areas, results in axial expansion of transducer 188 on the opposite side of polymer 182. The result is lateral bending of transducer 180, approximately 180 degrees from the center point of active area 188. The effect may also be measured by the deflection of a top portion 189 of transducer 180, which traces a radial arc from the resting position shown in FIG. 3C to his position at shown in FIG. 3D. Varying the amount of electrical energy provided to active area 188, and corresponding inner layer active areas, controls the deflection of the top portion 189 along this arc. Thus, top portion 189 of transducer 180 may have a deflection as shown in FIG. 3D, or greater, or a deflection minimally away from the position shown in FIG. 3C. Similar bending in an another direction may be achieved by actuating any one of the other radially aligned active area sets.

Combining actuation of the radially aligned active area sets produces a two-dimensional space for deflection of top portion 189. For example, radially aligned active area sets 186 and 184 may be actuated simultaneously to produce deflection for the top portion in a 45 degree angle corresponding to the coordinate system shown in FIG. 3C. Decreasing the amount of electrical energy provided to radially aligned active area set 186 and increasing the amount of electrical energy provided to radially aligned active area set 184 moves top portion 189 closer to the zero degree mark. Suitable electrical control then allows top portion 189 to trace a path for any angle from 0 to 360 degrees, or follow variable paths in this two dimensional space.

Transducer 180 is also capable of three-dimensional deflection. Simultaneous actuation of active areas on all four sides of transducer 180 will move top portion 189 upward. In other words, transducer 180 is also a linear actuator capable of axial deflection based on simultaneous actuation of active areas on all sides of transducer 180. Coupling this linear actuation with the differential actuation of radially aligned active areas and their resulting two-dimensional deflection as just described above, results in a three dimensional deflection space for the top portion of transducer 180. Thus, suitable electrical control allows top portion 189 to move both up and down as well as trace two-dimensional paths along this linear axis.

Although transducer 180 is shown for simplicity with four radially aligned active area sets disposed at 90 degree increments, it is understood that transducers of the present invention capable of two- and three-dimensional motion may comprise more complex or alternate designs. For example, eight radially aligned active area sets disposed at 45 degree increments. Alternatively, three radially aligned active area sets disposed at 120 degree increments may be suitable for 2D and 3-D motion.

In addition, although transducer 180 is shown with only one set of axial active areas, the structure of FIG. 3C is modular. In other words, the four radially aligned active area sets disposed at 90 degree increments may occur multiple times in an axial direction. For example, radially aligned active area sets that allow two- and three-dimensional motion may be repeated ten times to provide a snake like robotic manipulator with ten independently controllable links.

Nested Rolled Electroactive Polymer Devices

Some applications desire an increased stroke from a rolled electroactive polymer device. In one embodiment, a nested configuration is used to increase the stroke of an electroactive polymer device. In a nested configuration, one or more electroactive polymer rolls are placed in the hollow central part of another electroactive polymer roll.

Figures 3E, 3F, 3G:
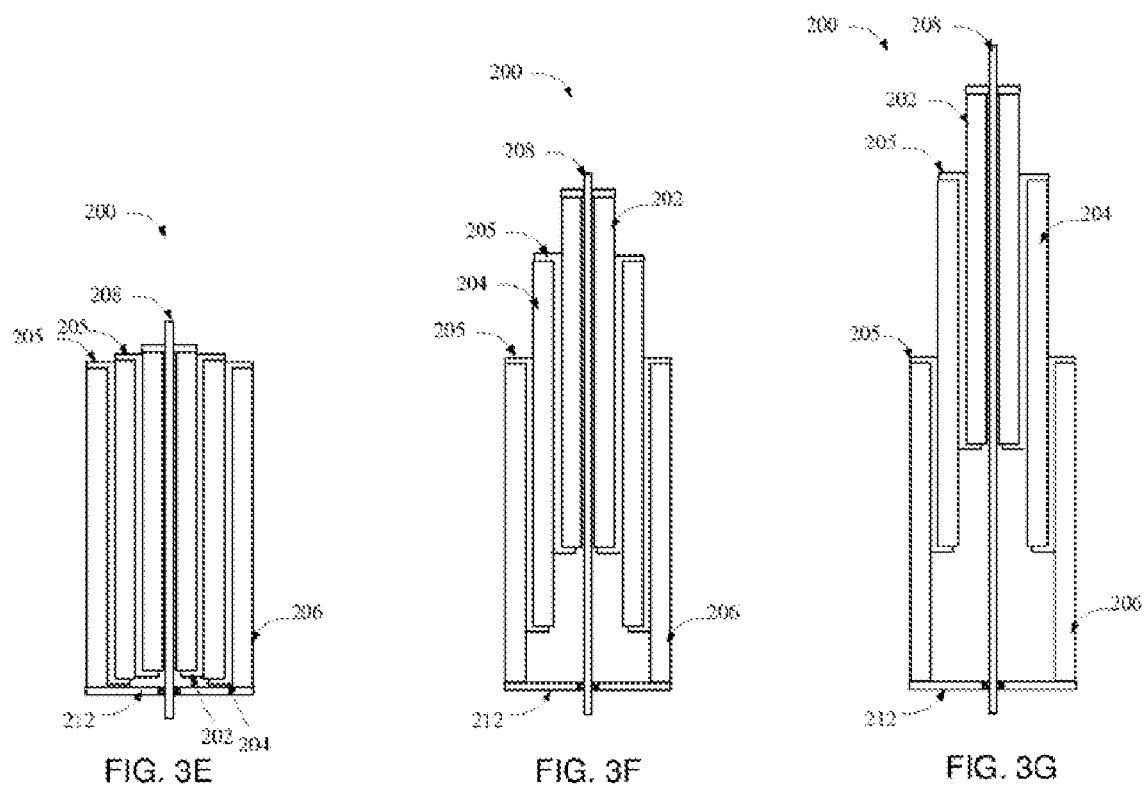
FIGS. 3E-G illustrate exemplary vertical cross-sectional views of a nested electroactive polymer device in accordance with one embodiment of the present invention.

FIGS. 3E-G illustrate exemplary cross-sectional views of a nested electroactive polymer device 200, taken through the vertical midpoint of the cylindrical roll, in accordance with one embodiment of the present invention. Nested device 200 comprises three electroactive polymer rolls 202, 204, and 206. Each polymer roll 202, 204, and 206 includes a single active area that provides uniform deflection for each roll. Electrodes for each polymer roll 202, 204, and 206 may be electrically coupled to actuate (or produce electrical energy) in unison, or may be separately wired for independent control and performance. The bottom of electroactive polymer roll 202 is connected to the top of the next outer electroactive polymer roll, namely roll 204, using a connector 205. Connector 205 transfers forces and deflection from one polymer roll to another. Connector 205 preferably does not restrict motion between the rolls and may comprise a low friction and insulating material, such as Teflon. Likewise, the bottom of electroactive polymer roll 204 is connected to the top of the outermost electroactive polymer roll 206. The top of polymer roll 202 is connected to an output shaft 208 that runs through the center of device 200. Although nested device 200 is shown with three concentric electroactive polymer rolls, it is understood that a nested device may comprise another number of electroactive polymer rolls.

Output shaft 208 may provide mechanical output for device 200 (or mechanical interface to external objects). Bearings may be disposed in a bottom housing 212 and allow substantially frictionless linear motion of shaft 208 axially through the center of device 200. Housing 212 is also attached to the bottom of roll 206 and includes bearings that allow travel of shaft 208 through housing 212.

The deflection of shaft 208 comprises a cumulative deflection of each electroactive polymer roll included in nested device 200. More specifically, individual deflections of polymer roll 202, 204 and 206 will sum to provide the total linear motion output of shaft 208. FIG. 3E illustrates nested electroactive polymer device 200 with zero deflection. In this case, each polymer roll 202, 204 and 206 is in an unactuated (rest) position and device 200 is completely contracted. FIG. 3F illustrates nested electroactive polymer device 200 with 20% strain for each polymer roll 202, 204 and 206. Thus, shaft 208 comprises a 60% overall strain relative to the individual length of each roll. Similarly, FIG. 3G illustrates nested electroactive polymer device 200 with 50% strain for each polymer roll 202, 204 and 206. In this case, shaft 208 comprises a 150% overall strain relative to the individual length of each roll. By nesting multiple electroactive polymer rolls inside each other, the strains of individual rolls add up and provide a larger net stroke than would be achieved using a single roll. Nested electroactive polymer rolled devices are then useful for applications requiring large strains and compact packages.

In another embodiment, shaft 208 may be a shaft inside a tube, which allows the roll to expand and contract axially without bending in another direction. While it would be advantageous in some situations to have 208 attached to the top of 202 and running through bearings, shaft 208 could also be two separate pieces: 1) a shaft connected to 212 and protruding axially about ⅘ of the way toward the top of 206, and 2) a tube connected to the top of 206 and protruding axially about ⅘ of the way toward 212, partially enveloping the shaft connected to 212.

Figure 3I:
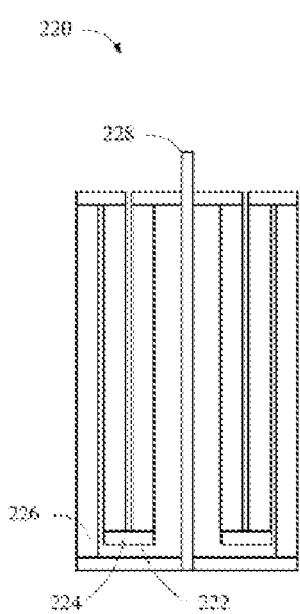
FIGS. 3H-J illustrate exemplary vertical cross-sectional views of a nested electroactive polymer device in accordance with another embodiment of the present invention.
Figure 3H:
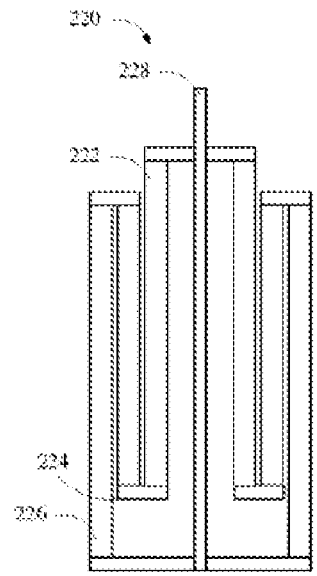
Figure 3J:
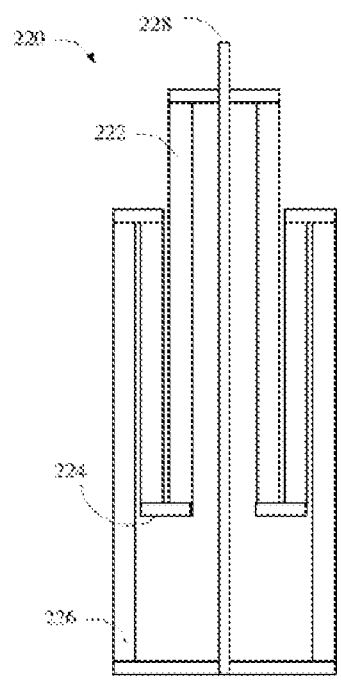
Figure 3K:
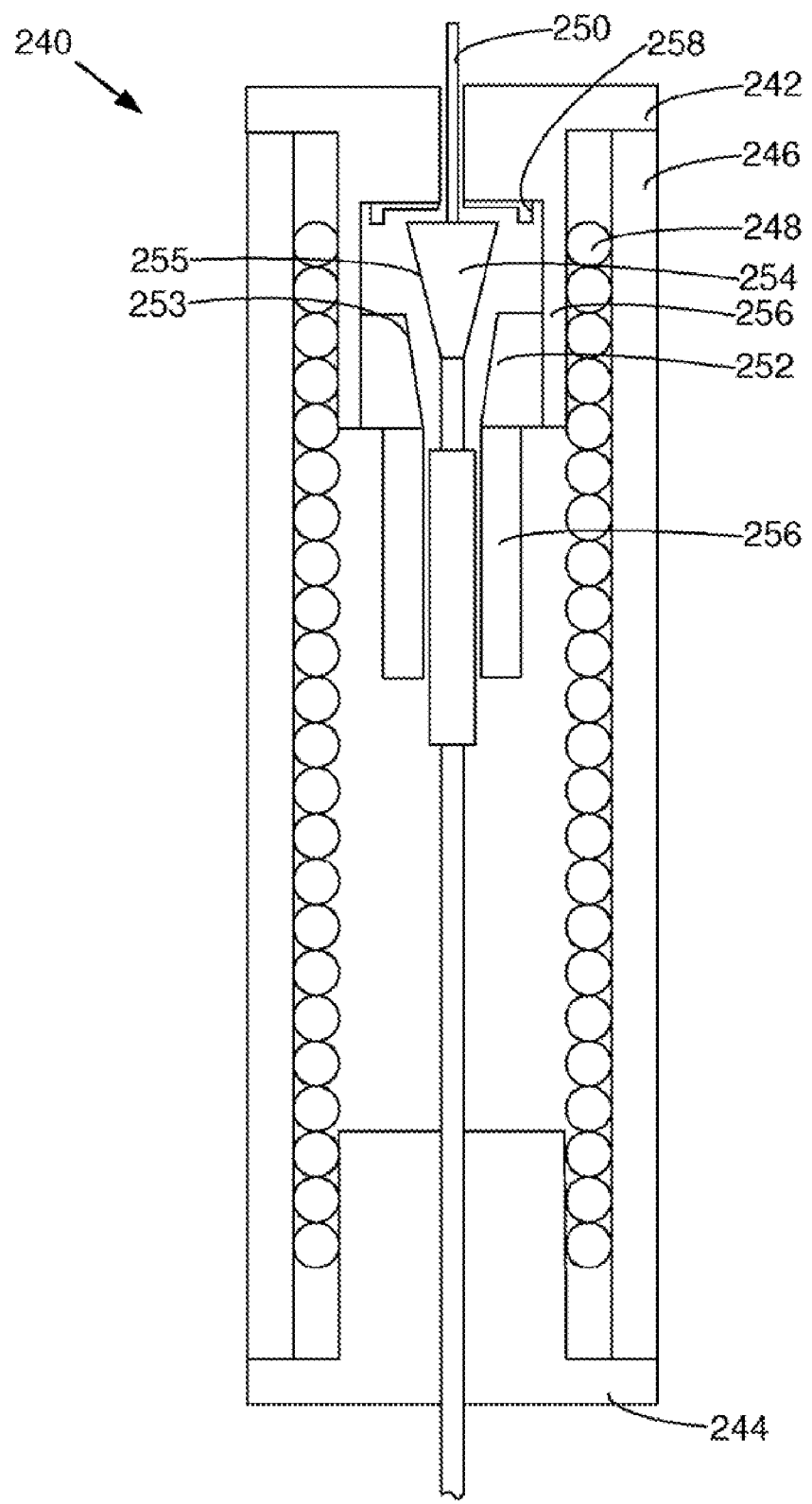
FIG. 3K illustrates a rolled electroactive polymer device that allows a designer to vary the deflection vs. force profile of the device.

FIGS. 3H-J illustrate exemplary vertical cross-sectional views of a nested electroactive polymer device 220 in accordance with another embodiment of the present invention. Nested device 220 comprises three electroactive polymer rolls 222, 224, and 226. Each polymer roll 222, 224, and 226 includes a single active area that provides uniform deflection for each roll.

In this configuration, adjacent electroactive polymer rolls are connected at their common unconnected end. More specifically, the bottom of electroactive polymer roll 222 is connected to the bottom of the next outer electroactive polymer roll, namely roll 224. Likewise, the top of electroactive polymer roll 224 is connected to the top of the outermost electroactive polymer roll 226. The top of polymer roll 222 is connected to an output shaft 228 that runs through the center of device 220. Similar to as that described with respect to shaft 208, shaft 222 may be a shaft inside a tube, which allows the roll to expand and contract axially without bending in another direction.

FIG. 3H shows the unactuated (rest) position of device 220. FIG. 3I shows a contracted position of device 220 via actuation of polymer roll 224. FIG. 3J shows an extended position of device 220 via actuation of polymer rolls 222 and 226. In the unactuated (rest) position of FIG. 3H, the shaft 208 position will be somewhere between the contracted position of FIG. 3I and the extended position of FIG. 3J, depending on the axial lengths of each individual roll.

This nested design may be repeated with an increasing number of layers to provide increased deflection. Actuating every other roll—starting from the first nested roll—causes shaft 228 to contract. Actuating every other roll—starting from the outermost roll—causes shaft 228 to extend. One benefit to the design of nested device 220 is that charge may be shunted from one polymer roll to another, thus conserving overall energy usage. It is worth noting that each device 200 or 220 may be operated as a high strain generator or sensor that receives mechanical energy via shaft 208 or 228, as will be described in further detail below.

Negative Spring Constant Designs

A mechanism of the present invention may vary the force it provides with deflection of the transducer or device. For rolled electroactive polymer devices that employ a spring, as the device axially extends, the output force of the device typically decreases as a result of the spring. In many applications, it is desirable to implement mechanical input, such as a linear actuator, whose output force is constant over the range of deflection—or increases with extension—according to the needs of the application. Such constant or negative spring constant mechanical input may be achieved using several mechanisms. Indeed, many such mechanisms could be attached to a rolled actuator externally or within the hollow interior. Additionally, it is also possible to make the spring structure itself operate as a constant or negative spring constant spring. For example, the spring could be made by stacking several Belleville washers on a rigid rod with a flange at one to restrain the most proximal Belleville washer. Belleville washers are circular disks with a central hole that are slightly conical. When compressed with sufficient force they can be made to pass through the point at which they are completely flat and become conical in the opposite direction from the original configuration. This flange is attached to one end of the roll. At the other end of the stack is a flat washer that is attached to the other end of the roll that restrains and allows the rolled polymer material to compress the Belleville washers past the point at which they become unstable and exert a force to invert the orientation of the cone. Many other negative spring constant mechanisms could be used that do not require Belleville washers. These mechanism need only be placed between each washer in a stack of flat washers so that the entire stack behaves as a negative constant spring. In all these examples, the edges of the washers provide support for the stretched polymer film. Other constant or negative spring constant mechanical input and there use to enhance the output of dielectric elastomer actuators are further described in patent Ser. No. 09/779,373, now U.S. Pat. No. 6,911,764, which is incorporated herein for all purposes.

FIG. 3K illustrates a rolled electroactive polymer device 240 that allows a designer to vary the deflection vs. force profile of the device. Device 240 comprises end pieces 242 and 244, rolled electroactive polymer 246, spring 248, rod 250, magnet 252, ferromagnetic core 254, and a magnet apparatus 256.

End pieces 242 and 244, rolled electroactive polymer 246, and spring 248 are similar in structure and function as that described above with respect to FIG. 2A. Rod 250 is coupled to end pieces 244 and slides within end piece 244. In one embodiment, the rod 250 is a solid rod that extends in length from bottom end piece 242 to top end piece 244, and screws into end piece 244 using mating threads in rod 250 and end piece 244. In one embodiment, the entire rod 250 is made of 2 pieces: 1) a rod with different diameters along the length of the rod (according to the embodiment shown in FIG. 3K, it would have four different diameters), and screwed into end piece 244 and 2) a tapered ferromagnetic core with a cylindrical hole of the same diameter as the top of rod 250. Thus, rod 250 is fixed to end piece 244, and slides relative to end piece 242 and magnet apparatus 256 as the polymer expands and contracts. Ferromagnetic core 254 is disposed on rod 250 somewhere between end pieces 242 and 244. Ferromagnetic core 254 is a metal (e.g., steel) or similar material that provides magnetic attraction and forces between itself and a magnetic field. Connected rigidly to top end piece 242 is magnetic apparatus 246, which supports and aligns a ring shaped magnet 252. Magnet 252 is thereby disposed concentrically with rod 250 and ferromagnetic core 254. Magnet 252 produces a magnetic field that attracts core 254.

Magnet 252 has a taper on its inner edge 253; and core 254 has a corresponding taper on its outer edge 255. With changing polymer 246 deflection and motion of rod 250, magnet 252 is drawn closer to core 254—thus exerting a force on slide 250 that increases as magnet 252 nears core 254. In one embodiment, magnet 252 is magnetized radially.

Thus, as rod 250 extends, the output force of slide 250 due to spring 248 gets weaker, but the output force of rod 250 due to the internal magnetic assembly gets stronger. Spring 248 and the internal magnetic assembly may be designed or configured to attain a desired force relationship with deflection. For example, spring 248 and internal magnetic assembly may be designed and configured such that the net force of rod 250 increases with polymer 246 deflection.

Since the force of magnetic attraction between magnet 252 and core 254 decreases with the square of rod 250 deflection, designing and implementing a 1:1 correspondence between linear slide deflection and magnetic attraction would result in a narrow operating range. However, with the tapered magnet design of device 240, as rod 250 encounters large deflections, the force of magnetic attraction changes only slightly, thereby resulting in a larger deflection operating range.

In another embodiment, magnet 252 has a vertical inner edge (a cylinder with a straight hole through it) and core 254 also has a matching cylindrical outer profile. In this case, there is a force from magnet 252 pulling core 254 completely inside magnet 252. As magnet 252 nears core 254, it similarly draws core 254 into the magnetic cylinder, thus resulting in a net force on rod 250. This second configuration allows simpler manufacture.

In one embodiment, device 240 also comprises a hard stop 258 attached to end piece 242. Hard stop 258 places a physical limit on how close magnet 252 can get to core 254, and prevents contact between magnet 252 and core 254. Alternatively, a barrier layer may be disposed between magnet 252 and core 254, such as a layer of plastic, cardboard, foam, etc., to prevent metal on magnet contact.

Actuator Designs for Precise Angular Control

Figure 3L:
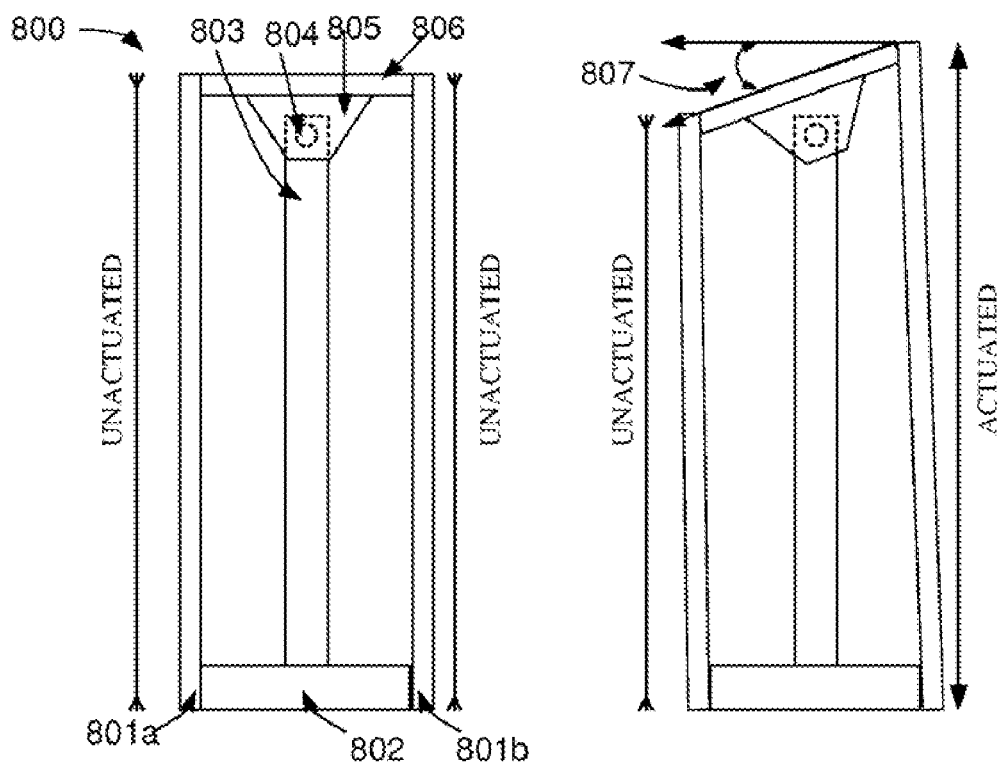
FIGS. 3L-3Z illustrate energy efficient rolled electroactive polymer devices designed to provide precisely controlled angular movements.
Figure 3M:
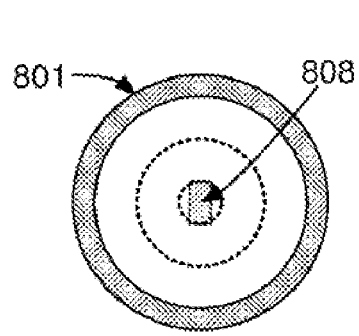

Previous examples of rolled actuators designs with the potential for both 1) bending and lengthening motions (e.g., FIG. 3D) or 2) lengthening motions with linear output (e.g., see FIGS. 3E-3K) have been described. FIGS. 3L-3Z illustrate energy efficient rolled electroactive polymer devices designed to provide precisely controlled angular movements, angular output, and angular stiffness control. These designs, provided for illustrated purposes only, may comprise one or more support members coupled to a rolled polymer actuator and mechanical linkages that allow for force transfers between different portions of the rolled polymer actuator. The apparatus and methods described with respect to FIGS. 3L-3Z are not necessarily limited to the rolled polymer actuator designs described in these figures and may be applicable to other rolled polymer actuator designs or non-rolled electroactive polymer actuator polymer designs. For example, FIG. 3V illustrates a number of methods for fastening a rolled polymer actuator to an end-cap, such as clamping. These fastening methods may be applied to other rolled and non-rolled electroactive polymer actuator designs.

FIG. 3L illustrates an embodiment of a rolled electroactive polymer actuator 800 with an angular output. FIG. 3L shows a cross-section of the device 800 and FIG. 3M shows a top view. On one end, a polymer roll 801, which may include a plurality of active areas, is fixed to a cylindrical base 802. Through the center of the polymer roll 801, a support member 803 with a circular cross section is coupled at the center of the base at a fixed 90 degree angle. In other embodiments, the support member 803 may be located off center of the base and may be fixed at angles different than 90 degrees. Further, the angle between the support member 803 and the base 802 does not necessarily have to be fixed. For instance, a linkage between the support member 803 and the base 802, such a linkage providing a pivot point, may allow the angle between them to vary.

The cross section of the support member 803 may be of any shape, such as round or square. The cross sectional shape of the support member may be constant along its length or may vary along its length (see FIG. 3U). The support member may be solid or hollow, such as a solid rod or a hollow tube.

In one embodiment, the support member 803 may comprise a plurality of extendable nested tubes, such as telescoping tubes. Thus, the support member may be lengthened or shortened by fixing the nested tubes at a particular length. For instance, the nested tubes may be pinned at a particular length. By changing the length of the nested tubes, an initial strain on the polymer roll may be increased or decreased.

In manufacture, the polymer may be rolled around and then secured to the telescoping tubes. Initially, the tubes may be at their minimum length. Then, the tubes may be stretched to the final length and fixed in position to provide a tensile force on the polymer roll.

The support member 803 is attached to an end cap 806 with flange 805 and a cylindrical bore 804. The support member 803 also includes a cylindrical bore 804. The support member 803 and the end cap 806 are shaped to allow a pin 808 to be inserted through the cylindrical bore 804 to provide a coupling between the support member 803 and the end cap 806 and to allow the end cap 806 to rotate about the pin 808.

The polymer roll 801 is secured to the end cap 806. In one embodiment, the polymer roll 801 is stretched so that it exerts a force that pulls the end cap 806 towards the base. The stretching is an initial strain (or pre-strain) on the polymer roll. The initial strain or pre-strain is in reference to the rolled actuator device 800 in an unactuated position. In this embodiment, in the unactuated position, the top of the end cap 806 is parallel to the base 802. In other embodiments, in the unactuated position, the top of the cap 806 and the base 802 may be non-parallel relative to one another. For instance, a force tunable spring may be used to set an initial angle between the end cap 806 and the base in the unactuated position. In another embodiment, the pivot point may be located off center from the axis through the center of the support member 803. Placing the pivot point off-center results in an initial non-horizontal angle to balance the moments about the pivot point generated by the polymer roll 801, which is in tension.

In FIG. 3L, the cross section of the polymer roll 801 shows two active areas 801a and 801b opposite one another that may be actuated. As previously described in FIGS. 3A-3D, the polymer roll 801 may be monolithic comprising a plurality of active areas. In operation, a voltage may be applied to the active area 801b. When the voltage is applied to area 801b, the polymer in this area lengthens and the end cap 806 rotates around the pin 808 through an angle 807. The ability of the polymer designs to produce large strains allows the end cap 806 to be rotated through a large range of angles. For instance, the top of the end cap may be rotated from a horizontal position relative to the base 802 to a nearly perpendicular position relative to the base in either direction.

A logic device and conditioning electronics (not shown) in communication with the polymer roll 801 and coupled to the device 800 may be used to position the end cap 806 at various angles 807 by controlling the voltages supplied to the active areas of the roll polymer 801. Further, when the end cap 806 is rotated from a first angle to a second angle, the logic device and the conditioning electronics may be used to control a rate of rotation of the end cap 806. The logic device may include a memory for storing a table that relates an angular position to operating parameters for the polymer roll 801, such as voltages and strains for the active areas. The logic device may use the table to position the end cap 806. The logic device may be operable to vary the position of the end cap 806 as a function of time.

The device 800 may include one or more sensors for measuring operating parameters of the device. A position of the end cap, an angular velocity of the end cap, an acceleration of the end cap, voltages on one portions of polymer roll 801 and strains on one or more portions of the polymer roll 801 are examples of operating parameters that may be directly measured or deduced from sensor measurements. In some embodiments, the measurements may be used in a feedback control loop for the device. In other embodiments, the device 800 may be designed as part of a sensor and the measurements may be used to generate a sensed output provided by the device. Further, details of logic devices, conditioning electronics, sensors and using rolled polymers for sensing purposes are described with respect to FIGS. 4, 5A, 5B and 7.

When the active area 801b is actuated and the end cap is rotated through angle 807, a portion of the polymer roll 801 is lengthened and a portion of the polymer roll 801 is shortened. Since the polymer roll 801 is in tension, the portion that is shortened provides a rotational moment about the pivot point that helps to rotate the end-cap through angle 807. The rotational moment generated by the unactuated portions of the polymer, such as 801a, decreases the energy needed to rotate the end cap 806. In one embodiment, during operation of the device 807, the angle 807 may be defined as a difference between an initial angular position and a second angular position.

Controlled angular output, such as, described in the paragraph above, may be used in many applications. For instance, the device 800 may be used as part of a servo-mechanism that controls the actuation of a side view mirror of an automobile. As another example, the device 800 may be used as part of a biomemetic robot.

The end cap 806 provides a mechanical linkage between portions of the polymer. In this case, the end cap 806 acts as a lever through the pivot point 804. In the present invention, many different types and combinations of mechanical linkages may be used to allow forces and moments to be communicated from a first portion of the polymer roll 801 to a second portion of the polymer roll 801. Some examples of mechanical linkages are described with respect to FIGS. 3P-3U.

The shape of the end cap 806 where the rolled polymer is attached may be varied from the round shape in FIG. 3M. For instance, the top of the end cap 806 and the base 802 where the polymer roll 801 is attached may be ovular. The ovular shape may be used to extend a length of a moment arm relative to the pivot point 804. In another example, the top of the end cap 806 and the base 802 may be different shapes, such as ovular and circular or circles of two different radii.

When a shape with a center, such as a circle or an oval, is used for the portion of the end cap 806 where the polymer roll is attached, the center of the shape does not necessarily have to be aligned with the center of the support member 803. When the center of shape of the end cap 806 is placed off center relative to the center axis of the support member 803, the moments about the pivot point can be varied. In addition, the present invention is not limited to ovular and circular shapes, which is provided for illustrative purposes only.

The material of the support member 803 may be selected to support the load exerted by the stretched polymer roll 801 as well as any loads experienced during operation of the device 800. Metals, plastics, ceramics and composites are examples of suitable materials. During operation of the device 800, the support member 803 may be designed to be rigid under some conditions and flexible under others. For instance, if the device is exposed to a sudden impulsive load, the support member 803 may be designed to bend to absorb the load rather than break in an analogous manner to a human bone. The material of the end cap 806 or any of the mechanical linkages of the present invention may be the same or different than the support members. Metals, plastics, ceramics and composites are examples of suitable materials.

Figure 3N:
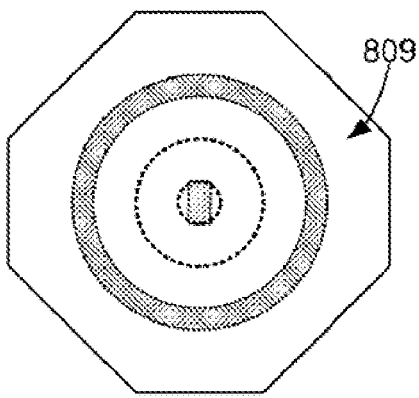
Figure 3O:
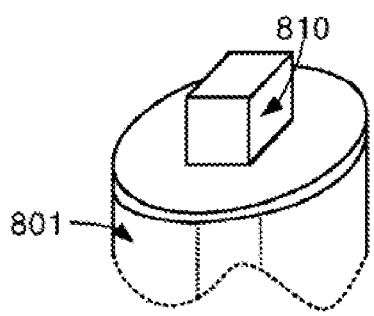

As shown in FIGS. 3N and 3O, the top of the end cap 806 may be shaped or include appendages. For instance, FIG. 3N shows a hexagonal cap mounted on top of the round end cap shown in FIG. 3M. As another example, FIG. 3O shows a square appendage on top of the end cap 806. In one embodiment, the shaped end cap or the appendage may be used for mating device 800 with another device 800 or other components. In another example, a passive element or appendage may be added on top of the end cap 806 to extend the range of motion of the device 800. Also, an additional linkage external could be attached to the end of the roll to increase the bending angle achieved using mechanical leverage.

Via the end cap 806 or another suitable component of the device 800, a force or a moment may be output. In addition, the device 800 may receive a force or a moment that is generated outside of the device via the end cap 806 or another suitable component. For instance, the device 800 could be a component in a joystick and could receive forces or moments from a person using the joystick.

When the device receives an outside force or an outside moment, the device 800 may generate a force or a moment in response. For example, in response to receiving an outside force one or more active areas of the polymer 801 may be actuated to "stiffen" the device to make it more difficult to move or to slow down a rate of movement of the device. In another example, the device 800 may vibrate or move in some other manner in response to the force. These types of responses may be used as part of a force feedback device, such as part of an input device used on a gaming console.

In another example, the device 800 could be used as a sensor that measures a change in a parameter due to an input of an outside force or moment to the device. For instance, in the joystick application, the device may be arranged to measure strains on different portions of the polymer 801 resulting from receiving an input force. The measured strains, which may be output by the device 800, may be used to determine a relative position of the device 800. In another example, the device 800*b* may be arranged to sense changes in its configuration to determine a magnitude of a force received as an input to the device. Other parameters that may be measured using the device 800 as part of a sensor include but are not limited to a linear position, an angular position, a linear velocity, an angular velocity, a linear acceleration, an angular acceleration and combinations thereof.

Returning to FIG. 3L, the end cap 806 is used as a single mechanical linkage to provide a communication of forces and moments between different portions of the polymer roll 801. The end cap 806 is connected to the support member using a pin mechanism, which allows rotation in one direction. The present invention is not limited to the single mechanical linkage, a pin connection mechanism or rotation in one direction. In FIGS. 3P-3U, embodiments of devices with a) multiple mechanical linkages of varying types, b) multiple rotational degrees of freedom, c) different types of mechanical linkage connection schemes are described.

In FIGS. 3P and 3Q, a cross section of a device 810 with a plurality of mechanical linkages, 806, 812*a*, 812*b* and 812*c*, for transferring forces and moments between different portions of the polymer roll 801 are described. The mechanical linkages, 806, 812*a*, 812*b* and 812*c* are each coupled to support member 803. The mechanical linkages are also coupled to the polymer roll 801. In one embodiment, a portion of each mechanical linkage may be attached to the polymer roll using an adhesive. The attachment scheme may vary from linkage to linkage. For example, the polymer roll 801 may be clamped to the end cap 806 and pinned to mechanical linkages 812*a*-*c*. A few examples of attachment schemes are later described with respect to FIG. 3V.

The device 810 may operate in a manner similar to the device 800 described with respect to FIG. 3L. When a voltage is applied to an active portion 801*b* of the polymer roll 801, the active portion 801*b* may lengthen and rotate the end cap 806 through the angle 807. The additional mechanical linkages, 812*a*-*c*, contribute rotational moments that may allow the device 810 to actuate more efficiently. Further, during operation of the device, the mechanical linkages, 812*a*-*c*, may provide shape stability to the polymer roll 801. For instance, the mechanical linkages may prevent the polymer roll 801 from necking between the end cap 806 and the base 802.

Many different shapes, connection schemes and arrangements of mechanical linkages may be used with the present invention. Different shapes of mechanical linkages are described with respect to FIG. 3Q', different arrangements are described with respect to FIGS. 3R and 3S and different connection schemes are described with respect to FIG. 3T.

For illustrative purposes, in FIG. 3Q', a few examples of mechanical linkage shapes are shown as a top view of mechanical linkage 812*a*.

Shape 814*a* is a circular disc with a bar for connecting to support member 803. Shape 814*b* is a circular disc with outer portions of the disc removed and a bar for connecting to support member 803. The removal of the outer portion of the disc eliminates contact and hence linkage with portions of the polymer 801 as compared to 814*a*. Shape 814*c* is more ovular and compact version of shape 814*b*.

Shape 814*d* is the shape 814*c* with a square appendage on one side. The movement of the mechanical linkage 812*a* generates a rotational moment 817 around axis 816. The square appendage on 814*d* may be used to transfer energy from the rotational moment 817 to another portion of device 810. For instance, in one embodiment, the square appendage may be coupled to a torsional spring that is wound or unwound when the polymer roll 801 is actuated. In one embodiment, the torsional spring may be used to generate a restoring force that helps to return an actuated portion of the polymer roll 801 to its unactuated position.

As described with respect to the end cap 806 in FIG. 3L, the shape of the mechanical linkages may be non-symmetric about axis 816. Further, the shapes of the mechanical linkages 812*a*-*c* may differ from one another, the shape of the end cap 806 and the shape of the base 802. Further, the shape of the mechanical linkage may not be planar. For instance, in FIG. 3P in the unactuated position of device 810, a first portion of the mechanical linkage 812*a* may be parallel to the end cap 806 and a second portion of the mechanical linkage 812*a* may be at angle to the end cap 806.

In embodiments of the present invention, an alignment of the couplings of the mechanical linkages to the support member 803 and a type of coupling may vary from linkage to linkage. For instance, in one embodiment, the end cap 806 may be coupled to the support member 803 using a ball and socket joint (not shown). Mechanical linkage 812*a* may use shape 814*b* (see FIG. 3Q') to connect to the support member 803, the mechanical linkage 812*b* may use shape 814*b* rotated 90 degrees (see FIG. 3R) to connect to support member 803 and mechanical linkage 812*c* may use the same shape and alignment as linkage 812*a* (See FIG. 3R) to connect to support member 803.

In this example, the device 810 may use two pairs of active regions on the polymer roll 801 aligned perpendicularly to one another. The four active regions on the polymer roll 801 may be actuated to position the end cap 806 with an orientation designated by two angles 818 and 819 as shown in FIG. 3S. The mechanical linkages, 812*a*/812*c* vs. 812*b*, generate rotational moments that act around axes that are perpendicular to one another. These rotational moments may be used to reduce the energy required to actuate the end cap 806 through angles 818 and 819 as shown in FIG. 3S.

Figure 3T:
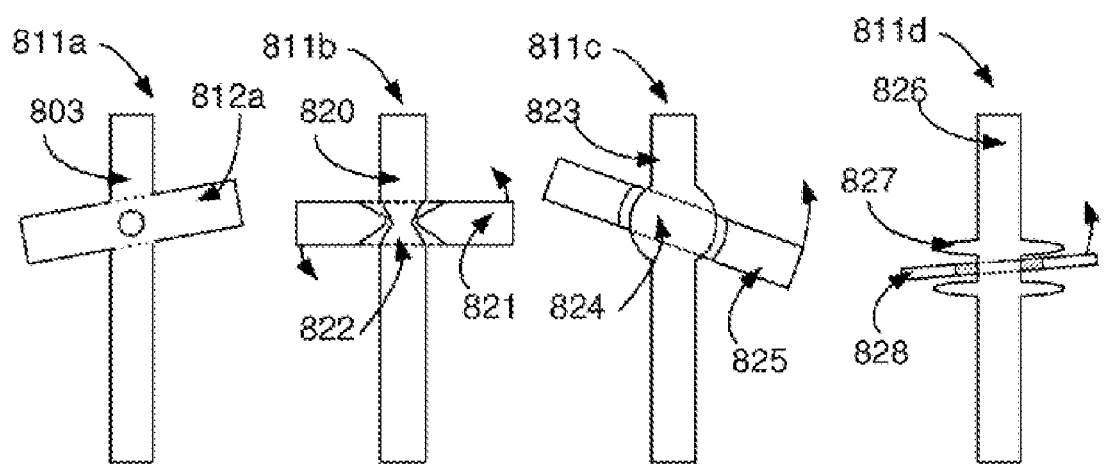
Figure 3U:
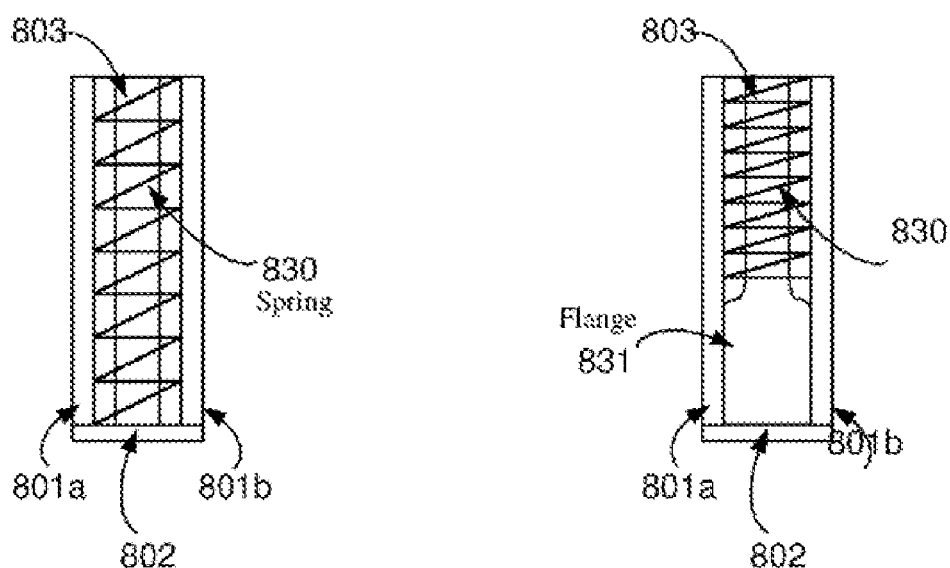
Figure 3V:
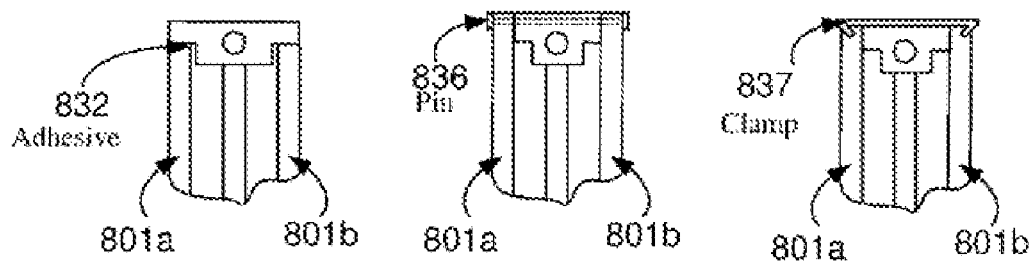

As described above with respect to FIGS. 3P-3S, the mechanical linkages of the present invention are not limited to pin systems. In FIG. 3T, a number of embodiments of mechanical linkage connection schemes are shown for illustrative purposes only as the present invention is not limited to these embodiments. A pin connection scheme 811*a* was previously described. A notched connection scheme 811*b* comprises a groove 822 in circular cross member 820. A mechanical linkage 821 with a circular inner diameter less than outer diameter of the support member allows for movement in multiple directions about the groove 822. The size and shape of the groove 822 may limit the range of motion of the mechanical linkage. For instance, the groove may not extend around the entire circumference of the support member 803.

A spherical connection scheme 811*c* comprises a spherical shaped portion 824 of support member 823. The mechanical linkage 825 may be rotated in multiple dimensions about the spherical portion 824. In one embodiment, the support member 823 may include a cylindrical rather than spherical shaped portion to limit the range of motion of mechanical linkage 825. A paired protuberance connection scheme 811*d* comprises two protuberances 827 around a circumference of support member 826. The two protuberances confine a mechanical linkage within the two protuberances to a particular range of motion.

The present invention is not limited to a plurality of separate mechanical linkages. In particular embodiments, the mechanical linkages may be linked to one another is some manner. For example, in one embodiment of the present invention, a spring 830 is a used as a mechanical linkage. Since the coils of the spring are all linked together, communication of forces between different portions of the mechanical linkage is possible. Further, the coils may be used to transfer forces and moments from different portions of the polymer roll along its length when the active areas 801*a* and 801*b* of the polymer roll are actuated. In addition, the spring also may provide shape stability to the roll along its length.

In another embodiment of the present invention, a solid material such as a foam sleeve may be placed around support member 803. The foam sleeve may be employed as a mechanical linkage to transfer forces and moments from a first portion of the polymer roll to a second portion of the polymer roll. Further, the foam leave may be used to provide shape stability for the polymer roll.

The mechanical linkages, such as spring 803, do not have to be located along the entire length of the support member 803. In one embodiment of the present invention in FIG. 3U, a spring 830, used as a mechanical linkage, spans only a portion of the length of support member 803. To provide additional shape stability for the polymer roll 801, the support member comprises a flange 831 flange of some kind of material (e.g., foam, plastic, metal) located below the spring 830.

In the present invention, the polymer roll 801 may be attached to the mechanical linkages using a variety of methods. A few of these examples are described with respect to FIG. 3V. In FIG. 3V, the polymer roll 801 is attached to an end cap using an adhesive, a pin, and a clamp. The end caps can be shaped to have ridges and/or lips for additional holding force. The clamp goes over the top of the end cap like a bottle cap. A combination of attachment schemes may be used to attach the polymer roll to the mechanical linkage. For example, the polymer roll may be clamped and glued to the mechanical linkage. Further, the attachment schemes may vary from mechanical linkage to mechanical linkage in the same device. For instance, the polymer roll 801 may be pinned and glued to a first mechanical linkage and only glued to a second mechanical linkage in the same device. In general, many types of fasteners may be used with the present invention and the invention is not limited to the examples provided above. Further, these attachment methods apply to all roll embodiments of the present invention and not only the examples described with respect to section 3.5.

In one embodiment, pins may be used to secure the polymer to a support member or mechanical linkage and in addition may be used as part of an electrical connection scheme. Thus, the pins may be manufactured from an electrically conductive material (In other embodiments of the present invention, the pins may be insulated.) When inserted through the electroactive polymer, the pins may electrically connect the active areas on multiple layers of the wrapped electroactive polymers. Further, the pins may connect two or more active areas on different portions of the polymer roll. For example, a pin may extend through one side of the roll, through the center of the roll and out the other side and electrically connect side active areas on the opposite side of the rolls.

In FIGS. 3L and 3P, an angular motion is provided at the end of device 800 and device 810 through the end cap 806. The present invention is not so limited. Devices of the present invention may comprise a support structure within the polymer roll with one or more joints where angular rotation is possible. The one or more joints where angular rotation is possible may be located at any position along the length of the polymer roll.

Figure 3W:
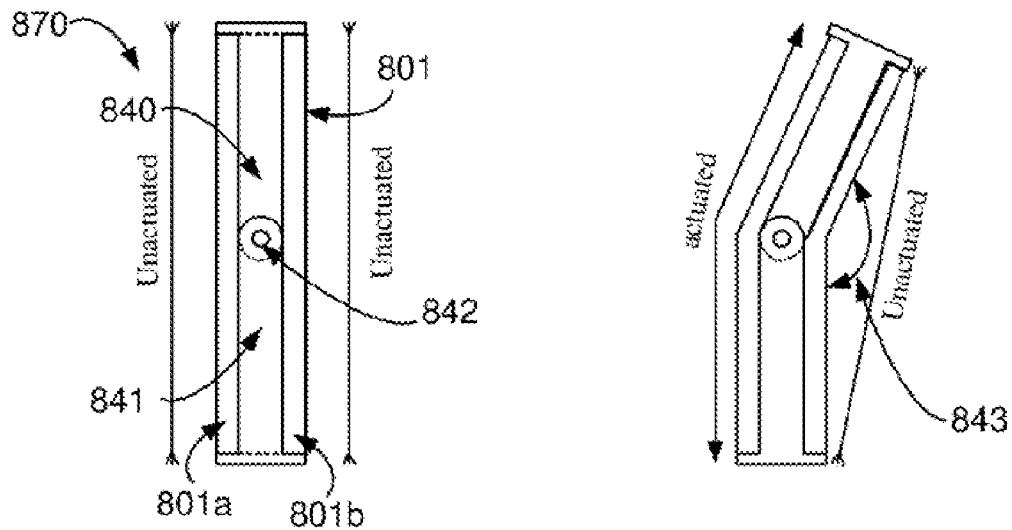

FIG. 3W shows a center cross-section of a device 870. The device 870 includes an electroactive polymer roll with at least two active areas 801*a* and 801*b*. Within the center of the polymer roll are two support members, 840 and 841. The support members are coupled via pinned joint 842. The pinned joint 842 is designed to allow the two support members, 840 and 841, to rotate relative to one another. In device 870, the polymer roll may be stretched and attached to the end caps of each of the support members 840 and 841. The stretching places an initial strain (pre-strain) on the polymer roll.

In one embodiment, the pinned joint 842 may be stopped to limit the amount of rotation. For example, the joint 842 may be stopped to allow the support members to align vertically and for support member 840 to rotate only to the right from the vertically aligned position. The joint 842 may be stopped to allow a variety of angular ranges and is not limited to being stopped with the support members in vertically aligned position.

When active area 801*b* is actuated, the polymer in the active area lengthens and support members 840 and 841 rotate toward one another such that the angle 843 between the support members is less than 180 degrees. Since the polymer roll is in tension, the unactuated portion of the polymer 801*b* may generate a rotational moment that helps to rotate the device 870 during actuation of the active area 801*a*. This design may help to minimize the energy needed to operate device 870. When the active area 801*a* is unactuated, the polymer in active area 801 a shortens and the device 870 is pulled back to an approximately vertically aligned position.

Many of the embodiments of the present invention have robotics related applications. When designing actuators for robotics, a designer often looks to nature for inspiration. For instance, humans and other animals use antagonistic muscle pairs. When one muscle of the antagonistic pair lengthens, the other muscle in the pair shortens. In FIGS. 3L, 3P, 3Q, when the devices, 800, 810 and 870, are operated, a first portion of the electroactive polymer roll lengthens and a second portion of the polymer roll, linked to the first portion via a mechanical linkage, shortens. Thus, the configuration and operation of these devices can be said to mimic an antagonistic muscle pair found in humans in other animals.

Figure 3X:
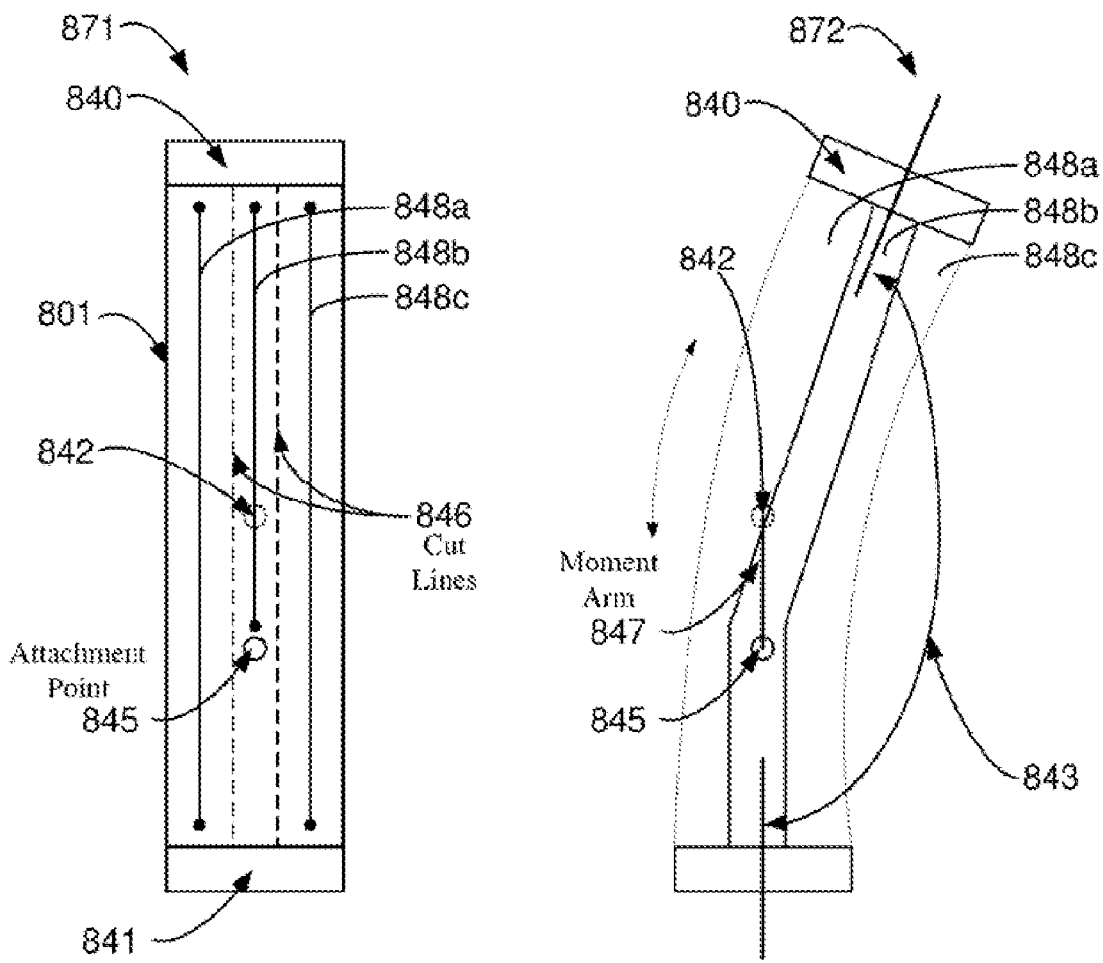
Figure 3Y:
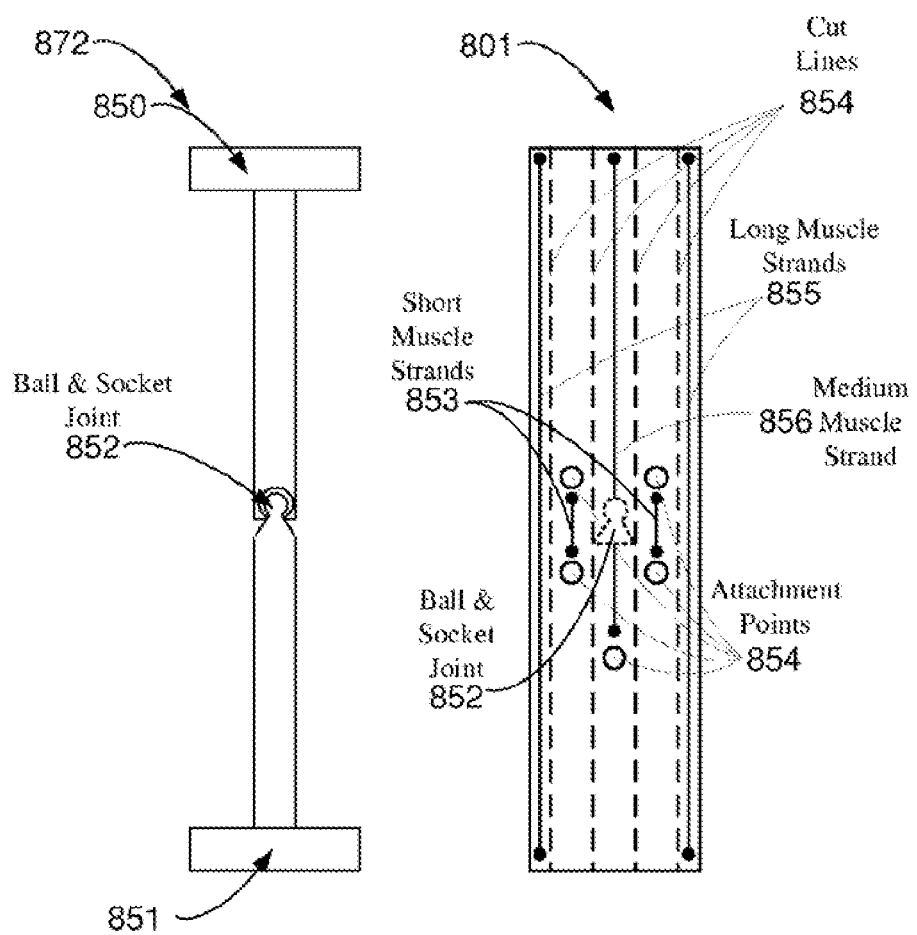
Figure 3Z:
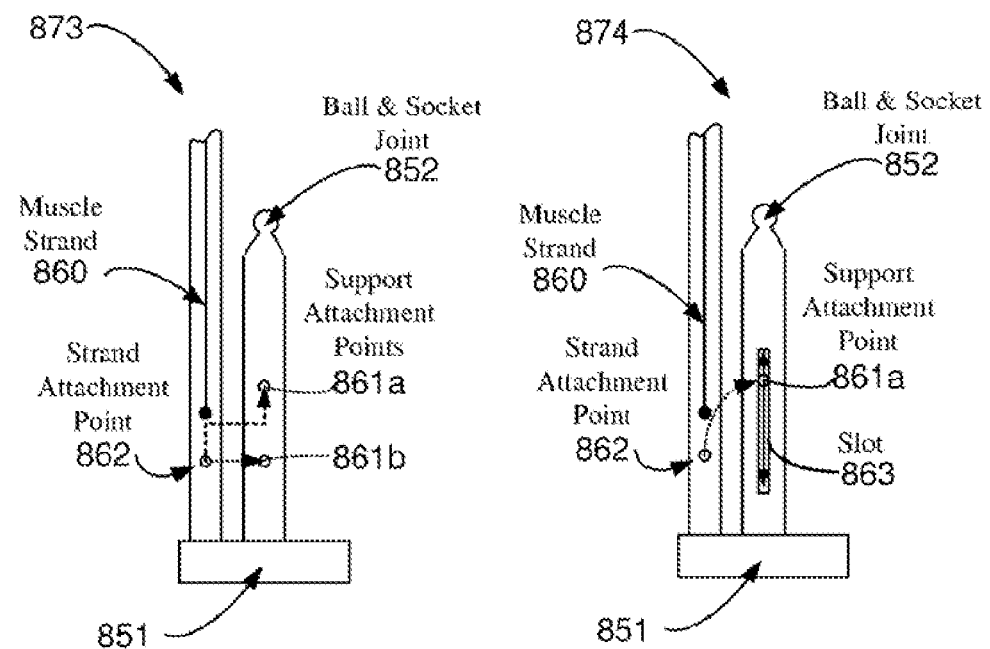

Besides antagonistic muscle pairs, at joint interfaces (e.g., at the knee), the human muscular-skeletal system employs attachments for large and small muscles. The attachments may be connected to antagonistic muscle pairs. These attachments may overlap and produce different forces and moments that aid in movement, balance and stability. In FIGS. 3X-Z, a number of embodiments of the present invention are described that can be said to mimic this aspect of human/animal physiology. Also, the animals use their antagonistic muscle pairs to vary joint stiffness by changing the static lengths of the muscles that span the joint. Varying joint stiffness can help the energetics of locomotion over various types of terrain and using various gaits.

FIG. 3X is view from the side of an actuator device 871, which includes an electroactive polymer roll 801. Device 871 starts with the configuration of device 870. As described with respect to FIG. 3W, the polymer roll 801 is attached to the end caps of support members 840 and 841, which are connected via pinned joint 842. Next, the polymer roll 801 is secured to the support member 841 at attachment point 845. For instance, the polymer may be pinned to support member 841 at attachment point 845.

Two cuts are made in the polymer roll along cut lines 846. The cuts may extend from an outer surface of the polymer roll 801 to an inner surface of the polymer roll i.e. slice through the roll 801 from the outer surface into the hollow center portion. The cuts may have the effect of preventing forces and moments generated in one portion of the polymer roll from propagating to another portion of the polymer roll.

The cuts along lines 846 may also be made on the opposite of the polymer roll 801 (not shown) to divide the polymer roll 801 into four "muscle strands." Three of the muscle strands 848*a*, 848*b*, 848*c* are shown in the figure. Each of the muscle strands may include one or more active areas that may be actuated. The muscle strands may be controlled and may move independently of one another. The cut lines allow each strand to slide past the other.

A length of each muscle strand may be defined as the distance between its attachment points. With this definition, an unactuated length of muscle strands 848*a* and 848*c* is the distance between its attachment points to the ends members 840 and 841 when members 840 and 841 are vertically aligned. When the members 840 and 841 are vertically aligned, an unactuated length of muscle strand 848*b* is shorter then muscle strands 848*a* and 848*c* because it attachment point is located in the middle of member 841 rather than at its end point.

When actuated, muscle 848*a* is allowed to lengthen between its two attachment points at base 840 and 841. When actuated muscle 848*b* is allowed to lengthen between its two attachment points at base 840 and attachment point 845. The attachment point 845 constrains the muscle 848*b* from lengthening between attachment point 845 and base 841 as a result of the actuation of muscle 848*b*.

The cut lines are shown extending the length of the roll for illustrated purposes only. In other embodiments, cut lines may be made that are smaller i.e., that do not extend the length of the roll. Further, cut lines may be made that are along a portion of the length of the roll, around a portion of the circumference or the roll. In general, the cut lines may be made along any 2-D curve on the outer surface of the roll. Further, the cut line may extend through all of the layers of the polymer roll or through only a portion of the layers of the polymer roll.

In another embodiment (see FIG. 3Z), the polymer roll may be first cut then secured at the attachment point rather than attached and then cut. Further, the cuts and the resulting muscle strands do not have to be arranged symmetrically about the circumference of the polymer roll.

In operation, device 871 may be actuated in a manner similar to device 870. Muscle strand 848*a* may be actuated such that it lengthens. The lengthening of muscle strand 848*a* and the initial strain placed on muscle strands 848*b* and 848*c* results in moments that rotate member 840. As previously described, this can be said to be mimic the workings of an antagonistic muscle pair in a human body.

After actuation of muscle strand 848*a*, muscle strand 848*b* may be actuated to more precisely match a desired angle between support members 840 and 841. For example, muscle strand 848*a* may be actuated so that the angle between the support members is smaller than desired. Then, muscle strand 848*b* may be actuated to increase the angle and to more closely match the desired angle. In general, the changes in angle produced by muscle strand 848*a* may be greater than the changes in angle generated by muscle strand 848*b*.

As previously describe, this can be said to mimic large and small muscle working together in the human body where the large muscle control gross movements and the small muscles control fine movements. A larger muscle strand may be used to generate the same amount of movement as a smaller muscle strand. However, an advantage of using a smaller muscle strand is that it may require less energy and may afford more precision than using a larger muscle strand.

In FIG. 3Y, another example of a polymer roll device 872 that uses "muscle strands" is shown. In the figure, support members 850 and 851 are connected via a ball and socket joint 852. With the ball and socket joint 852, the position of member 850 relative to member 851 may be defined by two angles.

An electroactive polymer roll 801 may be generated, stretched and attached to the ends of support members 850 and 851 as was described for devices 870 and 871. Then, a number of cuts may be made in the polymer roll 801 and attachment points added to create muscle strands of varying lengths. The polymer roll may be initially patterned so that active areas of a desired length are between the attachment points.

In FIG. 3Y, four cut lines 854 are made in the polymer roll and 5 attachment points to the support members are used. The cut lines and attachment points are used to create two long muscle strands 855, two short muscle strands 853 and one medium muscle strand 856. In operation, the long, medium and short muscle strands may be actuated independently to generate gross, medium and fine movements of the support members 850 and 851 about the ball and socket joint 852. These movements may be controlled by a logic device connect to the device 872.

In one embodiment of the present invention, the initial strains on each muscle strand may be adjusted relative to one another. As is described with respect to FIG. 3Y, an electroactive polymer roll 801 may be stretched and fixed to end points 850 and 851 and a number of cuts in the polymer roll may be made to generate a number of muscle strands. Then, the muscle strands are attached to the support members 850 and 851 to generate muscle strands of different lengths and with different moments about the ball and socket joint. To attach the muscle strands to the support members, an attachment point may be identified on the muscle strand. The location of attachment point on the muscle strand may not be initially aligned with the attachment point on the support member. Thus, prior to attaching the muscle strand to the support member, the muscle strand may be stretched or shrunk to increase or decrease or the initial strain on the muscle strand.

The process of adjusting the initial strain on a muscle strand is further described with respect to FIG: 3Z. Device 873 includes a support members, 850 (not shown) and 851 attached by a ball and socket joint 852. Support member includes two attachment points, 861*a* and 861*b*. The device 873 is shown in an initial stretched position after the attachment of the polymer roll 801 to the ends of two support members 850 and 851 (see FIG. 3Y) and initial cuts have been made to create the muscle strands.

Muscle strand 860 includes strand attachment point 862 where the active area of the muscle strand is above the attachment point. After the initial stretching of the polymer roll, strand attachment point 862 is aligned support attachment point 861b. Thus, the strain on the muscle strand 860 may be fixed at the value after the initial stretching by connecting strand attachment point 862 to attachment point 861b. Further, the strain on muscle strand 860 may be decreased from its value after the initial stretching by connecting strand attachment point 862 to attachment point 861b. In some embodiments, the pre-strain may be decreased to zero or a compressive strain may be placed on the muscle strand.

In another embodiment, in device 874, a slot 863 may be used to provide a range of attachment points of muscle strand 860 to support member 851. In this embodiment, the initial strain muscle strand 860 may be increased or decreased depending at what location in the slot the support attachment point 861a is fixed. In another embodiment of the present invention, the location of the support attachment point 861a may be varied during the operation of the device 874. Thus, the length of muscle strand 860 and hence its strain at a particular position may be varied to increase the efficiency the device or vary of stiffness of the device 874. In one embodiment, another electroactive polymer actuator may be used to adjust the position of the attachment point 861a.

Although not shown, in other embodiments, the devices 871, 872 and 873 may include a plurality of mechanical linkages as described above. These mechanical linkages may serve as attachment points for the muscle strands shown in device 871, 872 and 873. Further, the mechanical linkages may be used to connect two more muscle strands together in some manner.

In addition, a plurality of roll polymer actuators may be coupled together in a massively parallel system. For instance, a number of roll polymer actuators with angular output may be coupled together to produce an actuator capable of generating a snake-like motion. In another example, the actuators may be placed in parallel to allow for a starfish like motion.

Also, these configurations of angular control can be used for stiffness control. For example, if in FIG. 3L if 801a and 801b are actuated simultaneously then there will be increased compliance in that direction compared to the unactuated state. This angular stiffness control can also be applied to the connections shown in FIG. 3T to provide angular stiffness control in along multiple axis.

Multifunctionality

Electroactive polymers have many functional uses. In addition to actuation, active areas of the present invention may also be used for generation and production of electrical energy, sensing, stiffness control, or damping control.

FIGS. 1A and 1B may be used to show one manner in which the transducer portion 10 converts mechanical energy to electrical energy. For example, if the transducer portion 10 is mechanically stretched by external forces to a thinner, larger area shape such as that shown in FIG. 1B, and a relatively small voltage difference (less than that necessary to actuate the film to the configuration in FIG. 1B) is applied between electrodes 14 and 16, the transducer portion 10 will contract in area between the electrodes to a shape such as in FIG. 1A when the external forces are removed. Stretching the transducer refers to deflecting the transducer from its original resting position—typically to result in a larger net area between the electrodes, e.g. in the plane defined by directions 18 and 20 between the electrodes. The resting position refers to the position of the transducer portion 10 having no external electrical or mechanical input and may comprise any pre-strain in the polymer. Once the transducer portion 10 is stretched, the relatively small voltage difference is provided such that the resulting electrostatic forces are insufficient to balance the elastic restoring forces of the stretch. The transducer portion 10 therefore contracts, and it becomes thicker and has a smaller planar area in the plane defined by directions 18 and 20 (orthogonal to the thickness between electrodes). When polymer 12 becomes thicker, it separates electrodes 14 and 16 and their corresponding unlike charges, thus raising the electrical energy and voltage of the charge. Further, when electrodes 14 and 16 contract to a smaller area, like charges within each electrode compress, also raising the electrical energy and voltage of the charge. Thus, with different charges on electrodes 14 and 16, contraction from a shape such as that shown in FIG. 1B to one such as that shown in FIG. IA raises the electrical energy of the charge. That is, mechanical deflection is being turned into electrical energy and the transducer portion 10 is acting as a 'generator'.

When a relatively small voltage difference is applied between electrodes 14 and 16, deflection of transducer portion 10 will tend to change the voltage difference between the electrodes or drive charge to or from the electrodes, or do both, depending on the electrical state imposed on the electrodes 14 and 16. As polymer 12 changes in size, the changing electrical properties and voltage may be detected, dissipated, and/or used. For example, the change in voltage difference between the electrodes may be used to drive current to or from one of the electrodes which is dissipated through a resistor.

Some or all of the charge and energy can be removed when the transducer portion 10 is fully contracted in the plane defined by directions 18 and 20. Alternatively, some or all of the charge and energy can be removed during contraction. If the electric field pressure in the polymer increases and reaches balance with the mechanical elastic restoring forces and external load during contraction, the contraction will stop before full contraction, and no further elastic mechanical energy will be converted to electrical energy. Removing some of the charge and stored electrical energy reduces the electrical field pressure, thereby allowing contraction to continue. The exact electrical behavior of the transducer portion 10 when operating in generator mode depends on any electrical and mechanical loading as well as the intrinsic properties of polymer 12 and electrodes 14 and 16.

In some cases, the transducer portion 10 may be described electrically as a variable capacitor. The capacitance decreases for the shape change going from that shown in FIG. 1B to that shown in FIG. 1A. Typically, the voltage difference between electrodes 14 and 16 will be raised by contraction. This is normally the case, for example, if additional charge is not added or subtracted from electrodes 14 and 16 during the contraction process. The increase in electrical energy, U, may be illustrated by the formula $U=0.5\ Q^2/C$, where Q is the amount of positive charge on the positive electrode and C is the variable capacitance which relates to the intrinsic dielectric properties of polymer 12 and its geometry. If Q is fixed and C decreases, then the electrical energy U increases. The increase in electrical energy and voltage can be recovered or used in a suitable device or electronic circuit in electrical communication with electrodes 14 and 16. In addition, the transducer portion 10 may be mechanically coupled to a mechanical input that deflects the polymer and provides mechanical energy.

For a transducer having a substantially constant thickness, one mechanism for differentiating the performance of the transducer, or a portion of the transducer associated with a single active area, as being an actuator or a generator is in the change in net area orthogonal to the thickness associated with the polymer deflection. For these transducers or active areas, when the deflection causes the net area of the transducer/active area to decrease and there is charge on the electrodes, the transducer/active area is converting from mechanical to electrical energy and acting as a generator. Conversely, when the deflection causes the net area of the transducer/active area to increase and charge is on the electrodes, the transducer/active area is converting electrical to mechanical energy and acting as an actuator. The change in area in both cases corresponds to a reverse change in film thickness, i.e. the thickness contracts when the planar area expands, and the thickness expands when the planar area contracts. Both the change in area and change in thickness determine the amount of energy that is converted between electrical and mechanical. Since the effects due to a change in area and corresponding change in thickness are complementary, only the change in area will be discussed herein for sake of brevity. In addition, although deflection of an electroactive polymer will primarily be discussed as a net increase in area of the polymer when the polymer is being used in an actuator to produce mechanical energy, it is understood that in some cases (i.e. depending on the loading), the net area may decrease to produce mechanical work. Thus, devices of the present invention may include both actuator and generator modes, depending on how the polymer is arranged and applied.

Electroactive polymers of the present invention may also be configured as a sensor. Generally, electroactive polymer sensors of this invention detect a "parameter" and/or changes in the parameter. The parameter is usually a physical property of an object such as its temperature, density, strain, deformation, velocity, location, contact, acceleration, vibration, volume, pressure, mass, opacity, concentration, chemical state, conductivity, magnetization, dielectric constant, size, etc. In some cases, the parameter being sensed is associated with a physical "event". The physical event that is detected may be the attainment of a particular value or state of a physical or chemical property.

An electroactive polymer sensor is configured such that a portion of the electroactive polymer deflects in response to the change in a parameter being sensed. The electrical energy state and deflection state of the polymer are related. The change in electrical energy or a change in the electrical impedance of an active area resulting from the deflection may then be detected by sensing electronics in electrical communication with the active area electrodes. This change may comprise a capacitance change of the polymer, a resistance change of the polymer, and/or resistance change of the electrodes, or a combination thereof. Electronic circuits in electrical communication with electrodes detect the electrical property change. If a change in capacitance or resistance of the transducer is being measured for example, one applies electrical energy to electrodes included in the transducer and observes a change in the electrical parameters.

In one embodiment, deflection is input into an active area sensor in some manner via one or more coupling mechanisms. In one embodiment, the changing property or parameter being measured by the sensor corresponds to a changing property of the electroactive polymer, e.g. displacement or size changes in the polymer, and no coupling mechanism is used. Sensing electronics in electrical communication with the electrodes detect change output by the active area. In some cases, a logic device in electrical communication with sensing electronics of sensor quantifies the electrical change to provide a digital or other measure of the changing parameter being sensed. For example, the logic device may be a single chip computer or microprocessor that processes information produced by sensing electronics. Electroactive polymer sensors are further described in Ser. No. 10/007,705, which is incorporated herein by reference for all purposes.

An active area may be configured such that sensing is performed simultaneously with actuation of the active area. For a monolithic transducer, one active area may be responsible for actuation and another for sensing. Alternatively, the same active area of a polymer may be responsible for actuation and sensing. In this case, a low amplitude, high frequency AC (sensing) signal may be superimposed on the driving (actuation) signal. For example, a 1000 Hz sensing signal may be superimposed on a 10 Hz actuation signal. The driving signal will depend on the application, or how fast the actuator is moving, but driving signals in the range from less than 0.1 Hz to about 1 million Hz are suitable for many applications. In one embodiment, the sensing signal is at least about 10 times faster than the motion being measured. Sensing electronics may then detect and measure the high frequency response of the polymer to allow sensor performance that does not interfere with polymer actuation. Similarly, if impedance changes are detected and measured while the electroactive polymer transducer is being used as a generator, a small, high-frequency AC signal may be superimposed on the lower-frequency generation voltage signal. Filtering techniques may then separate the measurement and power signals.

Active areas of the present invention may also be configured to provide variable stiffness and damping functions. In one embodiment, open loop techniques are used to control stiffness and/or damping of a device employing an electroactive polymer transducer; thereby providing simple designs that deliver a desired stiffness and/or damping performance without sensor feedback. For example, control electronics in electrical communication with electrodes of the transducer may supply a substantially constant charge to the electrodes. Alternately, the control electronics may supply a substantially constant voltage to the electrodes. Systems employing an electroactive polymer transducer offer several techniques for providing stiffness and/or damping control. An exemplary circuit providing stiffness/damping control is provided below.

While not described in detail, it is important to note that active areas and transducers in all the figures and discussions for the present invention may convert between electrical energy and mechanical energy bi-directionally (with suitable electronics). Thus, any of the rolled polymers, active areas, polymer configurations, transducers, and devices described herein may be a transducer for converting mechanical energy to electrical energy (generation, variable stiffness or damping, or sensing) and for converting electrical energy to mechanical energy (actuation, variable stiffness or damping, or sensing). Typically, a generator or sensor active area of the present invention comprises a polymer arranged in a manner that causes a change in electric field in response to deflection of a portion of the polymer. The change in electric field, along with changes in the polymer dimension in the direction of the field, produces a change in voltage, and hence a change in electrical energy.

Often the transducer is employed within a device that comprises other structural and/or functional elements. For example, external mechanical energy may be input into the transducer in some manner via one or more mechanical transmission coupling mechanisms. For example, the transmission mechanism may be designed or configured to receive biologically-generated mechanical energy and to transfer a portion of the biologically-generated mechanical energy to a portion of a polymer where the transferred portion of the biologically generated mechanical energy results in a deflection in the transducer. The biologically-generated mechanical energy may produce an inertial force or a direct force where a portion of the inertial force or a portion of the direct force is received by the transmission mechanism. In one embodiment, the direct force may be from a foot strike.

Conditioning Electronics

Devices of the present invention may also rely on conditioning electronics that provide or receive electrical energy from electrodes of an active area for one of the electroactive polymer functions mentioned above. Conditioning electronics in electrical communication with one or more active areas may include functions such as stiffness control, energy dissipation, electrical energy generation, polymer actuation, polymer deflection sensing, control logic, etc.

For actuation, electronic drivers may be connected to the electrodes. The voltage provided to electrodes of an active area will depend upon specifics of an application. In one embodiment, an active area of the present invention is driven electrically by modulating an applied voltage about a DC bias voltage. Modulation about a bias voltage allows for improved sensitivity and linearity of the transducer to the applied voltage. For example, a transducer used in an audio application may be driven by a signal of up to 200 to 100 volts peak to peak on top of a bias voltage ranging from about 750 to 2000 volts DC.

Suitable actuation voltages for electroactive polymers, or portions thereof, may vary based on the material properties of the electroactive polymer, such as the dielectric constant, as well as the dimensions of the polymer, such as the thickness of the polymer film For example, actuation electric fields used to actuate polymer 12 in FIG. 2A may range in magnitude from about 0 V/m to about 440 MV/m. Actuation electric fields in this range may produce a pressure in the range of about 0 Pa to about 10 MPa. In order for the transducer to produce greater forces, the thickness of the polymer layer may be increased. Actuation voltages for a particular polymer may be reduced by increasing the dielectric constant, decreasing the polymer thickness, and decreasing the modulus of elasticity, for example.

Figure 4:
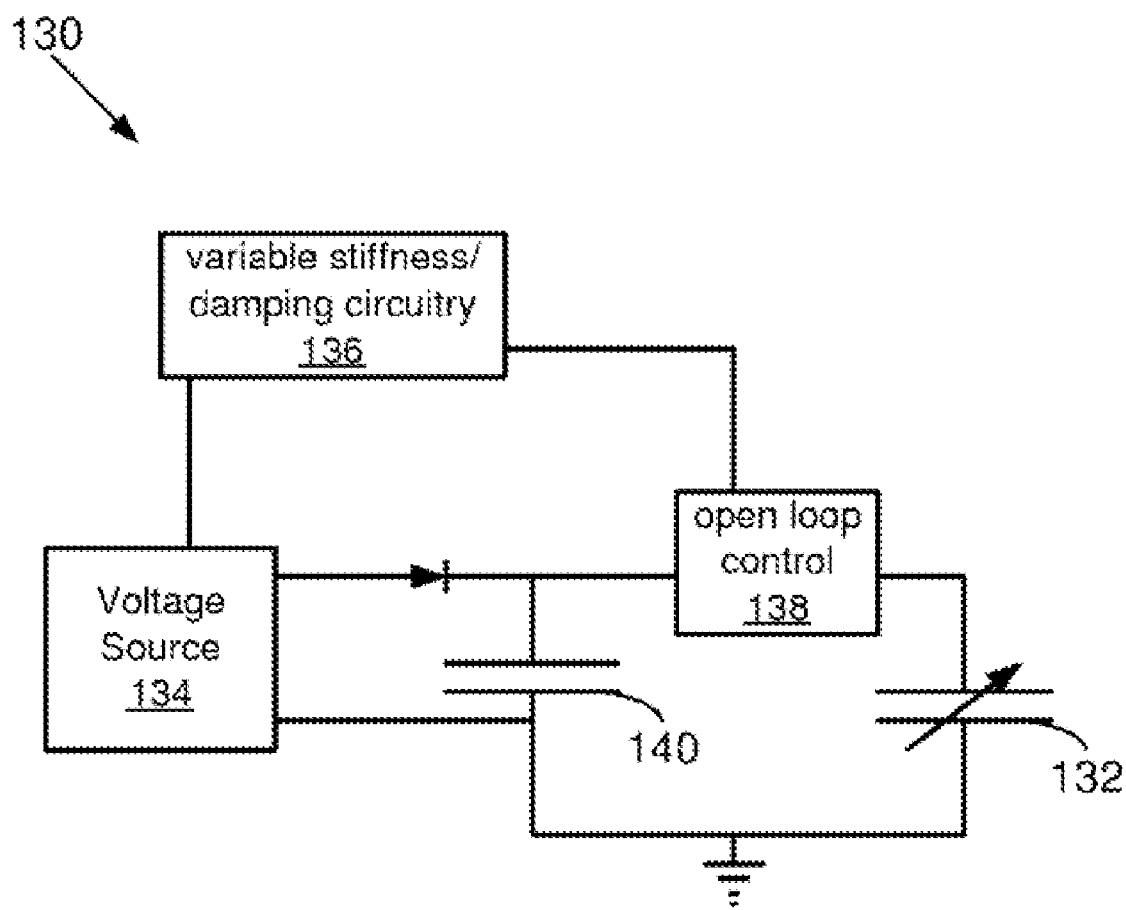
FIG. 4 illustrates an electrical schematic of an open loop variable stiffness/damping system in accordance with one embodiment of the present invention.

FIG. 4 illustrates an electrical schematic of an open loop variable stiffness/damping system in accordance with one embodiment of the present invention. System 130 comprises an electroactive polymer transducer 132, voltage source 134, control electronics comprising variable stiffness/damping circuitry 136 and open loop control 138, and buffer capacitor 140.

Voltage source 134 provides the voltage used in system 130. In this case, voltage source 134 sets the minimum voltage for transducer 132. Adjusting this minimum voltage, together with open loop control 138, adjusts the stiffness provided by transducer 132. Voltage source 134 also supplies charge to system 130. Voltage source 134 may include a commercially available voltage supply, such as a low-voltage battery that supplies a voltage in the range of about 1-15 Volts, and step-up circuitry that raises the voltage of the battery. In this case, voltage step-down performed by step-down circuitry in electrical communication with the electrodes of transducer 132 may be used to adjust an electrical output voltage from transducer 132. Alternately, voltage source 134 may include a variable step-up circuit that can produce a variable high voltage output from the battery. As will be described in further detail below, voltage source 134 may be used to apply a threshold electric field as described below to operate the polymer in a particular stiffness regime.

The desired stiffness or damping for system 130 is controlled by variable stiffness/damping circuitry 136, which sets and changes an electrical state provided by control electronics in system 130 to provide the desired stiffness/damping applied by transducer 132. In this case, stiffness/damping circuitry 36 inputs a desired voltage to voltage source 134 and/or inputs a parameter to open loop control 138. Alternately, if step-up circuitry is used to raise the voltage source 134, circuitry 136 may input a signal to the step-up circuitry to permit voltage control.

As transducer 132 deflects, its changing voltage causes charge to move between transducer 132 and buffer capacitor 140. Thus, externally induced expansion and contraction of transducer 132, e.g., from a vibrating mechanical interface, causes charge to flow back and forth between transducer 132 and buffer capacitor 140 through open loop control 138. The rate and amount of charge moved to or from transducer 132 depends on the properties of buffer capacitor 140, the voltage applied to transducer 132, any additional electrical components in the electrical circuit (such as a resistor used as open loop control 138 to provide damping functionality as current passes therethrough), the mechanical configuration of transducer 132, and the forces applied to or by transducer 132. In one embodiment, buffer capacitor 140 has a voltage substantially equal to that of transducer 132 for zero displacement of transducer 132, the voltage of system 130 is set by voltage source 134, and open loop control 138 is a wire; resulting in substantially free flow of charge between transducer 132 and buffer capacitor 140 for deflection of transducer 132.

Open loop control 138 provides a passive (no external energy supplied) dynamic response for stiffness applied by transducer 132. Namely, the stiffness provided by transducer 132 may be set by the electrical components included in system 130, such as the control electronics and voltage source 134, or by a signal from control circuitry 136 acting upon one of the electrical components. Either way, the response of transducer 132 is passive to the external mechanical deflections imposed on it. In one embodiment, open loop control 138 is a resistor. One can also set the resistance of the resistor to provide an RC time constant relative to a time of interest, e.g., a period of oscillation in the mechanical system that the transducer is implemented in. In one embodiment, the resistor has a high resistance such that the RC time constant of open loop control 138 and transducer 132 connected in series is long compared to a frequency of interest. In this case, the transducer 132 has a substantially constant charge during the time of interest. A resistance that produces an RC time constant for the resistor and the transducer in the range of about 5 to about 30 times the period of a frequency of interest may be suitable for some applications. For applications including cyclic motion, increasing the RC time constant much greater than the mechanical periods of interest allows the amount of charge on electrodes of transducer 132 to remain substantially constant during one cycle. In cases where the transducer is used for damping, a resistance that produces an RC time constant for the resistor and the transducer in the range of about 0.1 to about 4 times the period of a frequency of interest may be suitable. As one of skill in the art will appreciate, resistances used for the resistor may vary based on application, particularly with respect to the frequency of interest and the size (and therefore capacitance C) of the transducer 132.

In one embodiment of a suitable electrical state used to control stiffness and/or damping using open loop techniques, the control electronics apply a substantially constant charge to electrodes of transducer 132, aside from any electrical imperfections or circuit details that minimally affect current flow. The substantially constant charge results in an increased stiffness for the polymer that resists deflection of transducer 132. One electrical configuration suitable for achieving substantially constant charge is one that has a high RC time constant, as described. When the value of the RC time constant of open loop control 138 and transducer 132 is long compared to the frequency of interest, the charge on the electrodes for transducer 132 is substantially constant. Further description of stiffness and/or damping control is further described in commonly owned patent application Ser. No. 10/053,511, now U.S. Pat. No. 6,882,086, which is described herein for all purposes.

For generation, mechanical energy may be applied to the polymer or active area in a manner that allows electrical energy changes to be removed from electrodes in contact with the polymer. Many methods for applying mechanical energy and removing an electrical energy change from the active area are possible. Rolled devices may be designed that utilize one or more of these methods to receive an electrical energy change. For generation and sensing, the generation and utilization of electrical energy may require conditioning electronics of some type. For instance, at the very least, a minimum amount of circuitry is needed to remove electrical energy from the active area. Further, as another example, circuitry of varying degrees of complexity may be used to increase the efficiency or quantity of electrical generation in a particular active area or to convert an output voltage to a more useful value.

Figure 5A:
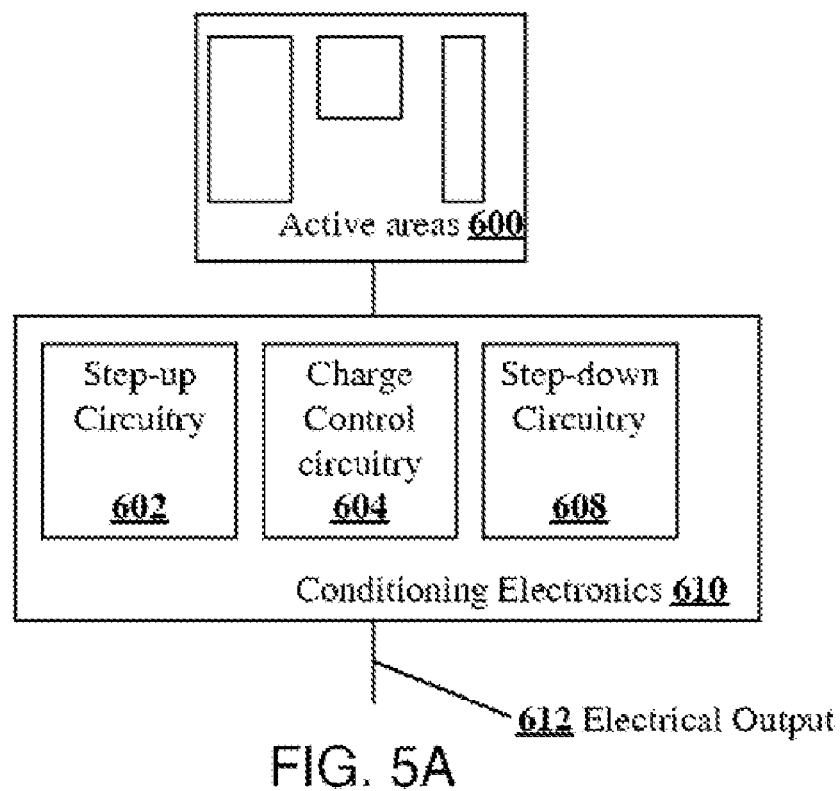
FIG. 5A is block diagram of one or more active areas connected to power conditioning electronics.

FIG. 5A is block diagram of one or more active areas 600 on a rolled transducer that connected to power conditioning electronics 610. Potential functions that may be performed by the power conditioning electronics 610 include but are not limited to 1) voltage step-up performed by step-up circuitry 602, which may be used when applying a voltage to active areas 600, 2) charge control performed by the charge control circuitry 604 which may be used to add or to remove charge from the active areas 600 at certain times, 3) voltage step-down performed by the step-down circuitry 608 which may be used to adjust an electrical output voltage to a transducer. All of these functions may not be required in the conditioning electronics 610. For instance, some transducer devices may not use step-up circuitry 602, other transducer devices may not use step-down circuitry 608, or some transducer devices may not use step-up circuitry and step-down circuitry. Also, some of the circuit functions may be integrated. For instance, one integrated circuit may perform the functions of both the step-up circuitry 602 and the charge control circuitry 608.

Figure 5B:
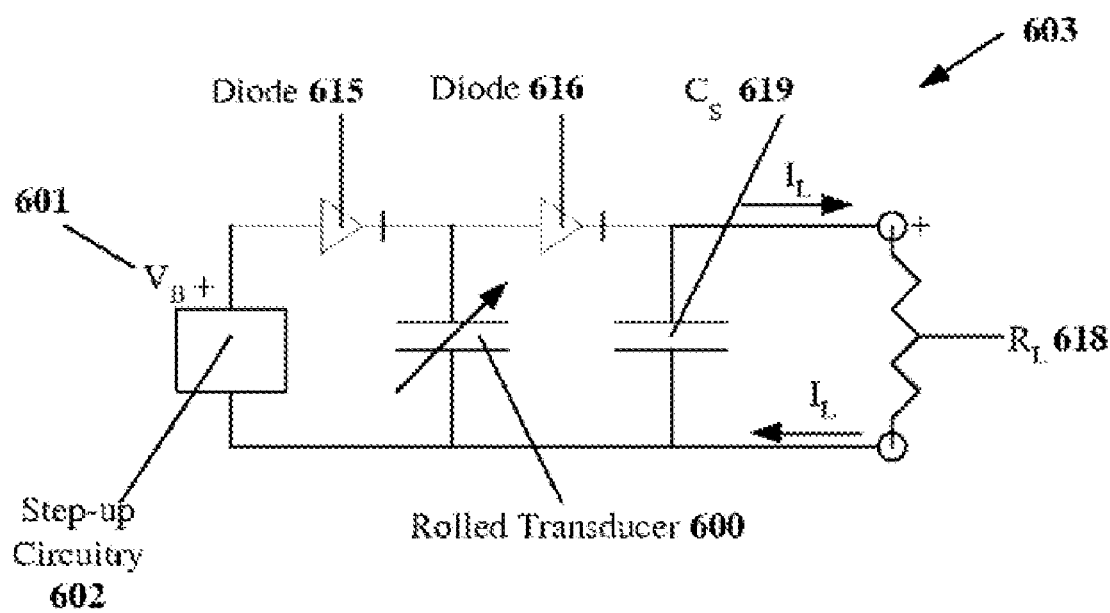
FIG. 5B is a circuit schematic of a device employing a rolled electroactive polymer transducer for one embodiment of the present invention.

FIG. 5B is a circuit schematic of an rolled device 603 employing a transducer 600 for one embodiment of the present invention. As described above, transducers of the present invention may behave electrically as variable capacitors. To understand the operation of the rolled transducer 603, operational parameters of the rolled transducer 603 at two times, $t_1$ and $t_2$ may be compared. Without wishing to be constrained by any particular theory, a number of theoretical relationships regarding the electrical performance the generator 603 arc developed. These relationships are not meant in any manner to limit the manner in which the described devices are operated and are provided for illustrative purposes only.

At a first time, $t_1$, rolled transducer 600 may possess a capacitance, $C_1$, and the voltage across the transducer 600 may be voltage 601, $V_B$. The voltage 601, $V_B$, may be provided by the step-up circuitry 602. At a second time $t_2$, later than time $t_1$, the rolled transducer 600 may posses a capacitance $C_2$ which is lower than the capacitance $C_1$. Generally speaking, the higher capacitance $C_1$ occurs when the polymer transducer 600 is stretched in area, and the lower capacitance $C_2$ occurs when the polymer transducer 600 is contracted or relaxed in area. Without wishing to bound by a particular theory, the change in capacitance of a polymer film with electrodes may be estimated by well known formulas relating the capacitance to the film's area, thickness, and dielectric constant.

The decrease in capacitance of the rolled transducer 600 between $t_1$ and $t_2$ will increase the voltage across the rolled transducer 600. The increased voltage may be used to drive current through diode 616. The diode 615 may be used to prevent charge from flowing back into the step-up circuitry at such time. The two diodes, 615 and 616, function as charge control circuitry 604 for rolled transducer 600 which is part of the power conditioning electronics 610 (see FIG. 5A). More complex charge control circuits may be developed depending on the configuration of the generator 603 and the one or more transducers 600 and are not limited to the design in FIG. 5B.

A rolled transducer may also be used as an electroactive polymer sensor to measure a change in a parameter of an object being sensed. Typically, the parameter change induces deflection in the transducer, which is converted to an electrical change output by electrodes attached to the transducer. Many methods for applying mechanical or electrical energy to deflect the polymer are possible. Typically, the sensing of electrical energy from a transducer uses electronics of some type. For instance, a minimum amount of circuitry is needed to detect a change in the electrical state across the electrodes.

Figure 7:
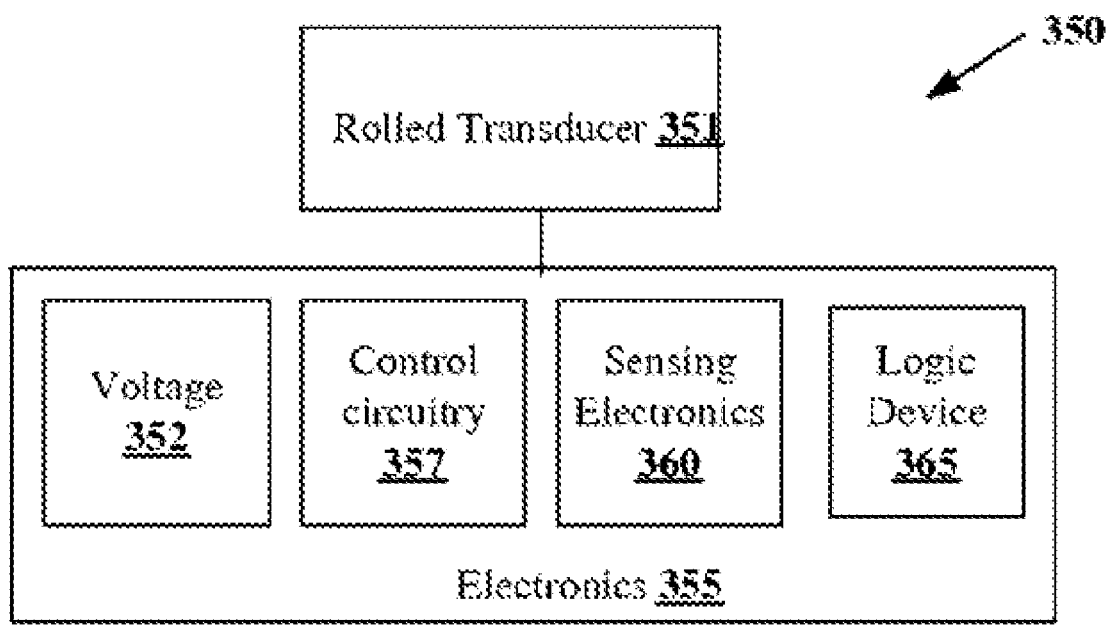
FIG. 7 is a schematic of a sensor employing a rolled electroactive polymer transducer according to one embodiment of the present invention.

FIG. 7 is a schematic of a sensor 350 employing a rolled transducer 351 according to one embodiment of the present invention. As shown in FIG. 7, sensor 350 comprises rolled transducer 351 and various electronics 355 in electrical communication with the electrodes included in the transducer 351. Electronics 355 are designed or configured to add, remove, and/or detect electrical energy from rolled transducer 351. While many of the elements of electronics 355 are described as discrete units, it is understood that some of the circuit functions may be integrated. For instance, one integrated circuit may perform the functions of both the logic device 365 and the charge control circuitry 357.

In one embodiment, the rolled transducer 351 is prepared for sensing by initially applying a voltage between its electrodes. In this case, a voltage, $V_1$, is provided by the voltage 352. Generally, $V_1$ is less than the voltage required to actuate rolled transducer 351. In some embodiments, a low-voltage battery may supply voltage, $V_1$, in the range of about 1-15 Volts. In any particular embodiment, choice of the voltage, $V_1$ may depend on a number of factors such as the polymer dielectric constant, the size of the polymer, the polymer thickness, environmental noise and electromagnetic interference, compatibility with electronic circuits that might use or process the sensor information, etc. The initial charge is placed on rolled transducer 351 using electronics control sub-circuit 357. The electronics control sub-circuit 357 may typically include a logic device such as single chip computer or microcontroller to perform voltage and/or charge control functions on rolled transducer 351. The electronics control sub-circuit 357 is then responsible for altering the voltage provided by voltage 352 to initially apply the relatively low voltage on rolled transducer 351.

Sensing electronics 360 are in electrical communication with the electrodes of rolled transducer 351 and detect the change in electrical energy or characteristics of rolled transducer 351. In addition to detection, sensing electronics 360 may include circuits configured to detect, measure, process, propagate, and/or record the change in electrical energy or characteristics of rolled transducer 351. Electroactive polymer transducers of the present invention may behave electrically in several ways in response to deflection of the electroactive polymer transducer. Correspondingly, numerous simple electrical measurement circuits and systems may be implemented within sensing electronics 360 to detect a change in electrical energy of rolled transducer 351. For example, if rolled transducer 351 operates in capacitance mode, then a simple capacitance bridge may be used to detect changes in rolled transducer 351 capacitance. In another embodiment, a high resistance resistor is disposed in series with rolled transducer 351 and the voltage drop across the high resistance resistor is measured as the rolled transducer 351 deflects. More specifically, changes in rolled transducer 351 voltage induced by deflection of the electroactive polymer are used to drive current across the high resistance resistor. The polarity of the voltage change across resistor then determines the direction of current flow and whether the polymer is expanding or contracting. Resistance sensing techniques may also be used to measure changes in resistance of the polymer included or changes in resistance of the electrodes. Some examples of these techniques are described in commonly owned patent application Ser. No. 10/007,705, now U.S. Pat. No. 6,809,462, which was previously incorporated by reference.

Fabrication

One advantage of rolled electroactive polymers of the present invention is simplified manufacture to obtain multilayer electroactive polymer devices. FIGS. 6A-6D describe the manufacture of a rolled electroactive polymer device in accordance with one embodiment of the present invention. While not described in detail, it is understood that fabrication techniques described below may be manually implemented, automated, or may comprise a combination of manual and automated techniques.

Fabrication according to one embodiment of the present invention employs a frame or fixture to facilitate rolling of an electroactive polymer. FIG. 6B illustrates a rolling fixture 650 useful for facilitating the rolling of one or more electroactive polymers. Fixture 650 includes length 652 and width 654 dimensioned according to the desired unrolled circumferential length and rolled height, respectively, of an electroactive polymer to be rolled. Smaller electroactive polymers may be fashioned using fixture 650 by using a portion of the fixture. For example, a rolled electroactive polymer may have an unrolled circumferential length less than height 652. In many cases, the electroactive polymer to be rolled is initially smaller than the rolling dimensions of fixture 650 and prestrain is used to increase the size of the polymer (see FIG. 6C).

Rolling fixture 650 fixtures an electroactive polymer during rolling, which in this context refers to one or more of: a) dimensioning an electroactive polymer for subsequent rolling, b) establishing and maintaining a desired prestrain level including holding the electroactive polymer and overcoming any elastic restoring forces in the polymer resulting from prestrain stretching, and c) functional reception of the rolling mechanism or process. Rolling fixture 650 may include any features or structures that provide or facilitate one of these functions. For example, to minimize bubbles and other defects between polymer layers during rolling, surface 656 is preferably substantially smooth with no surface defects that may introduce bumps or other inconsistencies in the surface of the polymer during rolling.

For some acrylic electroactive polymers, such as the such as VHB 4910 acrylic elastomer mentioned above for example, the acrylic has a high adhesion and may adhere to surface 656, thereby complicating the rolling process. Surface 656 allows the polymer to be rolled without complications. In one embodiment to overcome adhesive complications, surface 656 comprises a Teflon coating. In another embodiment in which fixture 650 is made from a rigid acrylic or when the electroactive polymer does not have adhesive properties, a tape or other adhesive control layer may be applied to the surface 656 to achieve a desired adhesiveness between the polymer and fixture rolling surface. The adhesive control layer eases peeling off of an adhesive polymer during rolling. In a specific embodiment, a crystal clear tape such as Scotch brand Crystal Clear Tape as provided by 3M Company of St. Paul, Minn. is used as an adhesive control layer.

When prestrain is applied to the polymer before rolling, receiving surface 656 preferably provides sufficient adhesion such that the prestrain is maintained by adhesion between the polymer and surface 656. However, as mentioned above, surface 656 is not so adhesive as to restrict peeling off of the polymer during the rolling process. This creates an adhesion range for the interface between surface 656 and the polymer that depends on the adhesion properties between the electroactive polymer and rolling surface 656. Thus, selection of a rolling surface 656 or an additional adhesive control layer may be used to control the interface between surface 656 and the polymer.

Fabrication according to the present invention may also rely on one or more additional fabrication fixtures or devices. Often, prestrain is applied to an electroactive polymer. This involves stretching polymer material, such as a thin film, from an area initially smaller than rolling dimensions to an area close to the rolling dimensions; and implies that the polymer must be held that this larger size during rolling. FIG. 6C illustrates a stretching fixture 660 useful for stretching an electroactive polymer and maintaining prestrain in accordance with one embodiment of the present invention. Stretching fixture 660 includes a substantially flat rigid frame 662 that defines a central opening or hole 664. A polymer 668 is stretched in both directions 667 and 669 and adhered to frame 662 perimetrically around hole 664. The adhesion between polymer 668 and frame 662 will depend on electroactive polymer material and frame 662 material. For example, electroactive polymer 668 may be an acrylic polymer with adhesive properties and frame 662 may be a rigid acrylic plate that provides significant adhesion to an acrylic electroactive polymer with adhesive properties. In other cases, securing and adhesive mechanisms such as removable clamps and two way tape may be applied perimetrically, or in portions, about hole 664 to hold the prestrain polymer 668 to frame 660 in a desired state of prestrain.

Figure 6A:
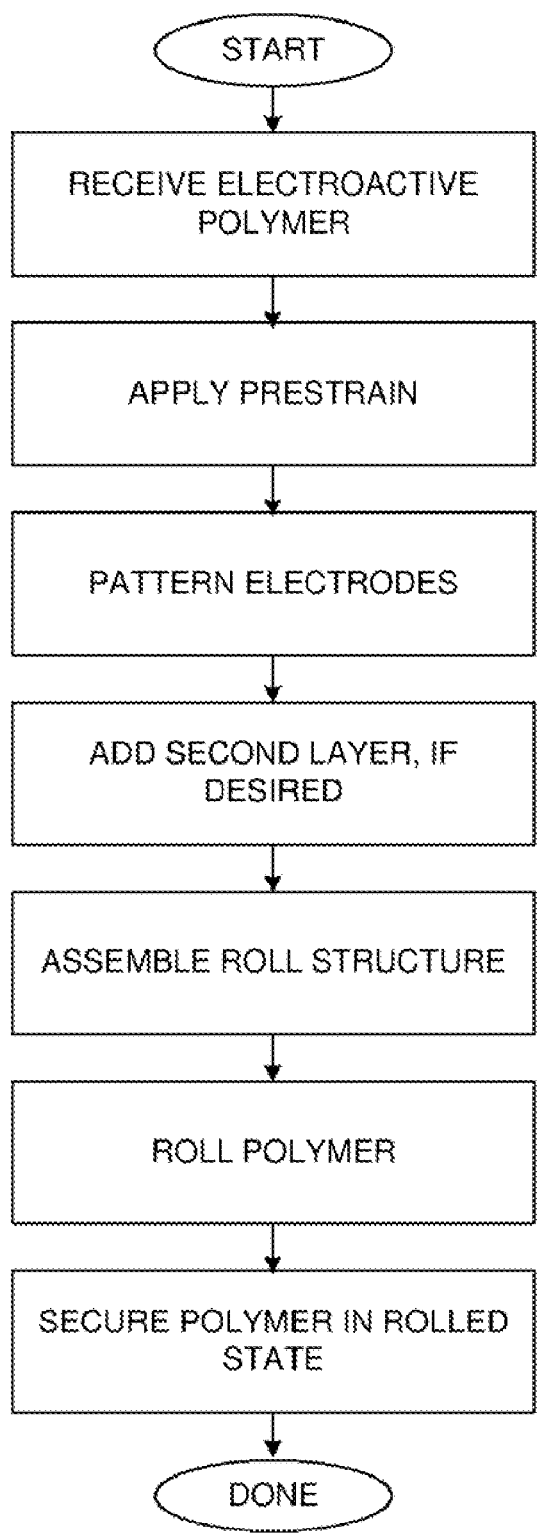
FIGS. 6A-6D describe the manufacture of a rolled electroactive polymer device in accordance with one embodiment of the present invention.
Figure 6B:
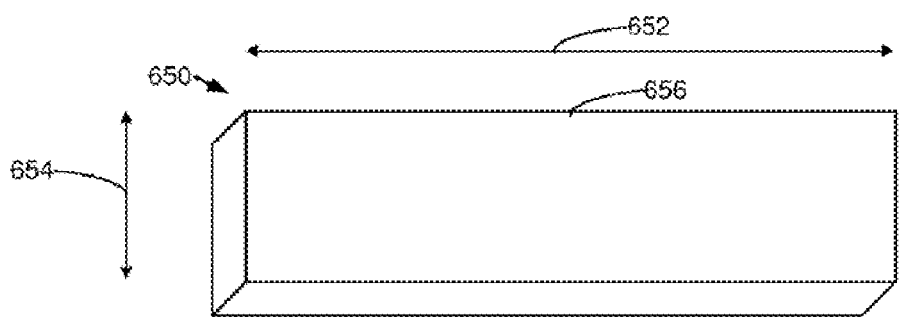

FIG. 6A illustrates a process flow 640 for fabricating electroactive polymer device comprising a rolled electroactive polymer in accordance with one embodiment of the present invention. Methods in accordance with the present invention may include up to several additional steps not described or illustrated herein order not to obscure the present invention.

Process flow 640 begins by receiving an electroactive polymer (641). The polymer may be a commercially available product such as a commercially available acrylic elastomer film. Alternatively, the polymer may be a film produced by one of casting, dipping, spin coating or spraying. Spin coating typically involves applying a polymer mixture on a rigid substrate and spinning to a desired thickness. The polymer mixture may include the polymer, a curing agent and a volatile dispersant or solvent. The amount of dispersant, the volatility of the dispersant, and the spin speed may be altered to produce a desired polymer. By way of example, polyurethane films may be spin coated in a solution of polyurethane and tetrahydrofuran (THF) or cyclohexanone. In the case of silicon substrates, the polymer may be spin coated on an aluminized plastic or a silicon carbide. The aluminum and silicon carbide form a sacrificial layer that is subsequently removed by a suitable etchant. Films in the range of one micrometer thick may be produced by spin coating in this manner. Spin coating of polymer films, such as silicone, may be done on a smooth non-sticking plastic substrate, such as polymethyl methacrylate or teflon. The polymer film may then be released by mechanically peeling or with the assistance of alcohol or other suitable release agent.

In one embodiment, prestrain is applied to the polymer, before rolling, by stretching the polymer in one or more directions (642). As described above, the prestrain may be anisotropic or isotropic. In one embodiment, prestrain is applied by stretching the polymer from about 300% to about 500% in direction 669 and 50% to about 200% in direction 667 as shown in FIG. 6C. In a specific embodiment, prestrain is applied by stretching the polymer 400% in direction 669 and 100% in direction 667. Maintaining prestrain includes temporarily fixing the polymer in some manner. This may include use of a stretching fixture, such as fixture 660.

Figure 6E:
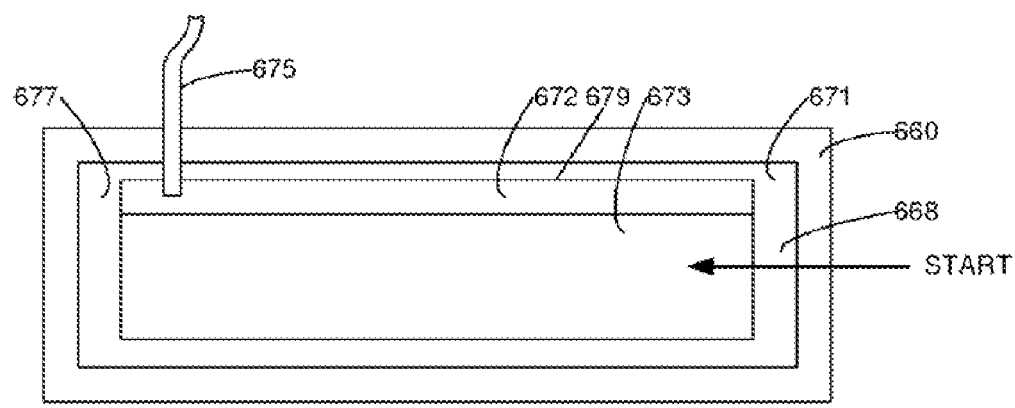
FIG. 6E illustrates a substantially rectangular electrode patterned on the facing side of an electroactive polymer held by stretching frame in accordance with one embodiment of the present invention.
Figure 6C:
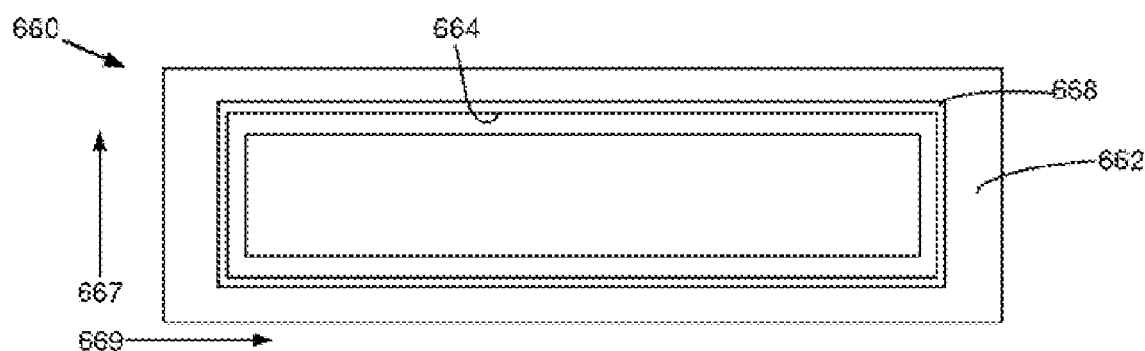

Electrodes are then patterned onto opposing surfaces of the electroactive polymer (643). Specific techniques used to pattern the electrodes will depend on the electrode type. For carbon grease electrodes, the carbon grease may be manually brushed onto the polymer within a brush. A stencil or template may be placed over the polymer to help define an electrode area during the brushing process. Carbon fibril electrodes may also be sprayed onto the polymer within a region defined by a stencil. In this case, a 0.1% dispersion of BN-type fibrils in ethyl acetate may be suitable. Time may also be provided for sprayed electrodes to dry. From about one hour to about eight hours may be suitable in some cases, depending on the composition and amount of electrode applied. In one embodiment, a stencil defines an electrode area region of about 30 cm to about 35 cm by about 2 cm to about 5 cm. FIG. 6E illustrates a substantially rectangular electrode 673 patterned on the facing side of an electroactive polymer held by stretching frame 660 in accordance with one embodiment of the present invention.

Both starting and finishing ends of polymer 668 include a portion 671 and 677, respectively, that to do not include electrode material. Portion 677 is not electroded to allow an outermost layer for the finished rolled device that does not include electrodes and acts as a barrier layer for mechanical protection and electrical isolation. When polymer 668 is rolled about a metal spring, portion 671 is not electroded to provide electrical isolation between inner layer electrodes at the metal spring.

Leads may also be disposed in electrical communication with the electrodes. When contact electrodes are used on both sides of polymer 668, a lead is attached to each contact electrode on both sides of polymer 668. In a specific embodiment, the lead comprises one or more copper or gold wires placed between aluminum foil and double sided tape. As shown in FIG. 6E, aluminum foil 672 is disposed along the top edge 679 of electrode 673 on the facing side of polymer 668. Aluminum foil 672 improves charge communication (charge distribution or collection) between electrode 673 and lead 675. Aluminum foil 672 is disposed along the edge of electrode 673, such that when the polymer is rolled, the aluminum foil 672 is proximate to either the top or bottom cylindrical end of the rolled device. A lead and aluminum foil are also disposed along the bottom edge of an electrode patterned on the opposite side of polymer 668. For an acrylic electroactive polymer with adhesive properties, the aluminum foil may include a portion that overlaps the top edge of the electrode and onto the adhesive polymer outside the electrode. This second portion then adheres to the adhesive polymer via the adhesive properties of the polymer. Lead 675 is disposed on aluminum foil 672 and secured to aluminum foil 672 using two sided tape placed over top of both lead 675 and aluminum foil 672. In one embodiment, lead 675 is a wire. The two sided tape secures lead 675 in position, and also prevents any sharp edges on lead 675 from damaging adjacent polymer layers after rolling. Off-the-shelf aluminum foil and two sided tape such as 3M two sided tape may be suitable for use as aluminum foil 672 and two sided tape 675, respectively.

In one embodiment, a multiple layer rolled construction is used (644). In this case, a second layer of electroactive polymer 680 is disposed on top of the electrode polymer 668 (see FIG. 6F). As mentioned before, the layers in the multiple layer stack need not be the same material. Other types of polymer (electroactive polymer or non-electroactive polymer) may be included in the stack, for example, to vary the stiffness of the stack.

For some acrylic electroactive polymers, adhesive properties of the acrylic polymer hold the layers together. In one embodiment, electrodes are not patterned for the second polymer 680. After rolling, electrode 673 on the top surface of polymer 668 acts as an electrode for both the top side of polymer 668 and the bottom side of polymer 680. After rolling, the electrode 681 on the bottom side of polymer 668 contacts the top side of polymer 680 and acts as an electrode for the top side of polymer 680. Thus, after rolling, polymer 680 includes electrodes that contact both planar surfaces. Another electroded polymer layer may be disposed on top of polymer 680, along with another polymer layer having no electrodes. All four may then be rolled. This even-numbered layer construction in which one polymer is electroded and the other is not may be repeated to produce 6 or 8 layer rolls (or more), as desired.

Rolling a flat sheet introduces a strain gradient across the thickness of the polymer—the strain is greater (in the tensile direction) towards the outer surface of the polymer. If a polymer roll is tightly wound, or thick or numerous layers of polymer are incorporated into the roll, than the strain difference may make the dimensions and performance of the inner layers different than the outer layers. Thus, a multilayer stack that is composed of individual layers will have different amounts of prestrain in the horizontal direction, which corresponds to the circumferential direction when rolled. Typically, outer layers in the multilayer stack will have a larger prestrain than inner layers. Differential prestrain between layers may result in differential performance between layers.

Figure 6D:
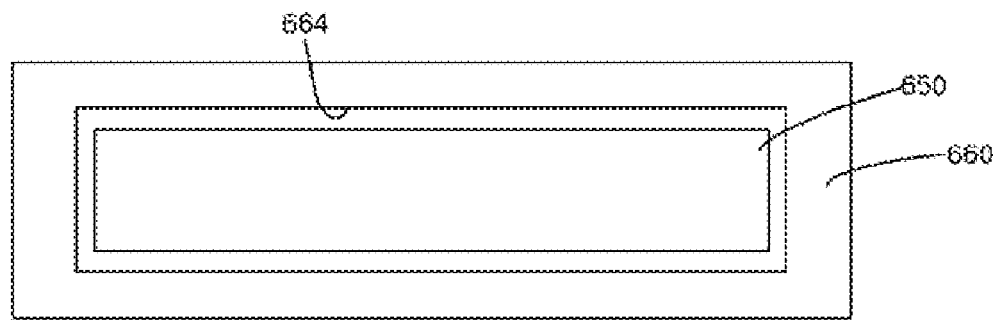
Figure 6F:
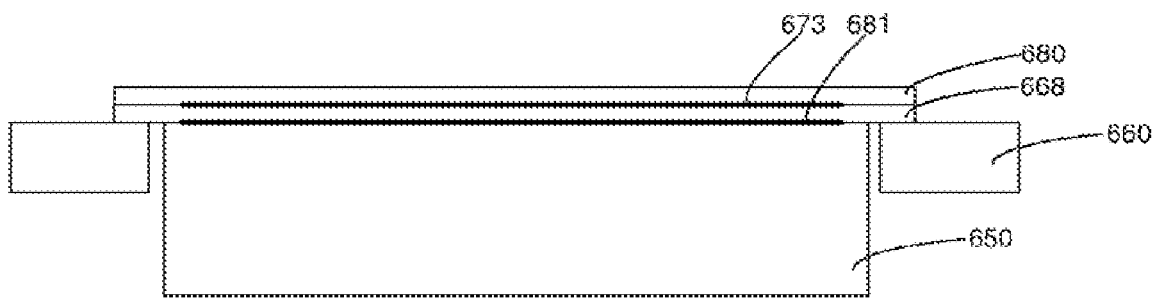
FIG. 6F illustrates a multiple layer rolled construction that includes a second layer of electroactive polymer disposed on top of the electrode polymer of FIG. 6E.
Figure 6G:
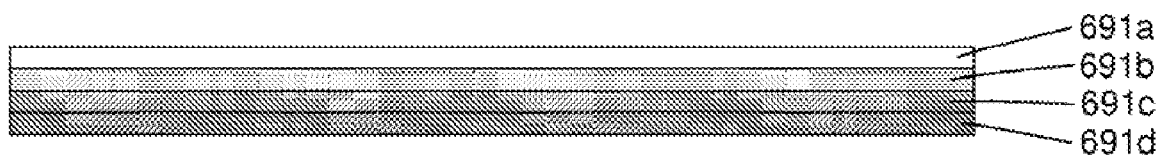
FIGS. 6G and 6H illustrate differing prestrain in a multilayer stack comprising four layers.
Figure 6H:
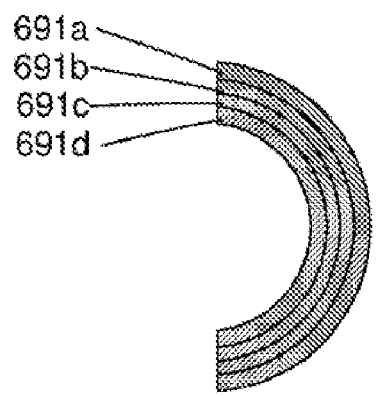

To achieve more consistent prestrain and performance throughout the roll, differing levels of prestrain may be applied to the multilayer stack before rolling. The differing levels of prestrain compensate for the strain gradient imposed on outer layers of a multilayer stack imposed by rolling. FIGS. 6G and 6H illustrate differing prestrain in a multilayer stack 690 comprising four layers 691. In FIG. 6G—before rolling, the lighter shading refers to a greater prestrain. In FIG. 6H—after rolling, the substantially constant shading refers to a substantially constant prestrain among the rolled layers 691.

In FIG. 6G, each layer 691a-d is disposed onto multilayer stack 690 with a different amount of prestrain, depending on its position within the stack. The strain gradient between layers 691 in FIG. 6G effectively cancels out the strain gradient introduced by curving the polymer layers when rolled. This situation is illustrated by the curved segment 694 illustrated in FIG. 6H. Since each layer 691 in the multilayer stack is typically prestrained separately by stretching it on a frame before applying it to the stack, the prestrain of each layer may be made different by stretching it more or less in one or more directions when it is put on to the frame.

It may also be possible to introduce a strain gradient by soaking a multilayer stack in a liquid that is absorbed into the stack. The liquid contacts only one side of the stack and is slowly absorbed by the polymer in the liquid. The amount of absorption at any point in time, and consequently the amount of strain depends on the distance from the liquid bath. An example of a complimentary polymer and liquid pair is the 3M VHB acrylic described above and polyol ether. In this case, the liquid relaxes the polymer, thereby effectively reducing prestrain in both orthogonal directions. The effect of the liquid may also be controlled to some extent by barrier layers and/or temperature control. For example, the liquid may be absorbed at relatively elevated temperatures to speed absorption. When the multilayer stack is returned to room temperature, the absorption will be relatively fixed by the cooler temperature, e.g. little subsequent diffusion of the liquid will take place. In another embodiment, barrier layers that prevent or inhibit diffusion may be used to achieve different levels of prestrain in layers 691. For example, with a simple two layer laminate, a polymer barrier may be disposed between the two electroactive polymer layers and used so that liquid is absorbed only into one electroactive polymer layer. The barrier polymer may be incorporated as a natural part of an electrode.

Returning to process flow 640, the polymer is typically rolled about some type of structure (645). In the case of a compressive spring, the polymer is rolled around the spring while compressed. In one embodiment, spring compression during rolling is accomplished by a bolt that passes through the center of the spring and threads into inner threads of end pieces on both ends of the spring. When fabrication and process flow 640 is complete, the bolt is removed and the spring and polymer will deflect to an equilibrium position determined by the spring and polymer stiffnesses. Alternatively, the bolt and compression may be maintained after fabrication but before usage, e.g., during storage, to minimize any creep in the polymer. In one embodiment, process flow 640 includes treating the spring surface with PTFE release agent to reduce friction between the spring and the polymer film to be rolled onto the spring.

The polymer layer(s) are then rolled (646). In one embodiment, this includes placing the polymer, or polymer stack, onto a rolling fixture such as fixture 650 shown in FIG. 6B. FIG. 6D illustrates the stretching fixture 660 of FIG. 6C disposed over the rolling fixture 650 of FIG. 6B. As shown, the inner opening of hole 664 is larger than the outer periphery of fixture 650. During rolling, an adhesive or glue may be added to end pieces—or some other structure involved in the rolling—to help secure polymer layers to each other, and to help secure polymer layers to a rigid object involved in the final construction.

Before rolling, the polymer or polymer stack is cut according to the outside dimensions of fixture 650. In one embodiment where prestrain is used and the polymer is stretched from its resting state, cutting the polymer may induce defects at the newly formed edges corresponding to cut. Coupled with stretching forces associated with prestrain, these defects may propagate through the stretched polymer. To minimize edge defect formation and propagation, an edge support layer may be disposed on one or both sides of polymer 680 along the edges to be cut. The edge support layer is fixed to the outer periphery of the polymer and provides mechanical support in these regions. The edge support layer may comprise a layer of clear tape (such as 3M crystal clear tape), kapton, or polyimide, from about 2 mm to about 5 mm in width, for example.

For an acrylic electroactive polymer with adhesive properties, polymer material outside of patterned electrodes may adhere to the surface of the rolling fixture 650 and help maintain prestrain in the polymer established by stretching fixture 660. When the polymer is rolled about a compression spring, the compressed spring is placed on either end of the polymer on rolling fixture 650 and rolled down the length of the polymer.

The polymer is then secured in its rolled configuration (647). A piece of double sided tape may also be attached to the portions of the polymer rolled initially, or finally, or both. In either case, the double sided tape contributes to holding the rolled polymer and prevents unrolling. Glue or another suitable adhesive may also be used to secure and maintain the rolled configuration of electroactive polymer. If end pieces are used at either end of the rolled electroactive polymer, an adhesive is disposed such that it contacts an end portion of the polymer (when rolled) and the rigid end piece and holds the end piece to the polymer. An external covering may also be added to the rolled electroactive polymer. Multiple layers of a thin insulating polymer rolled or wrapped around the electroactive polymer may provide suitable mechanical electrical protection for the electroactive polymer. For example, multiple layers of VHB 9460 may be wrapped around electroactive polymer. In another embodiment, after the rolling, a rigid ring, metal strip, or plastic strip is tightly wrapped around the portion of the rolled polymer on the end piece. Small holes are drilled (if they are not already established) through the rigid wrap, the polymer stack, and at least a portion of an end piece. Adhesive is applied into the hole, followed by a nail or screw (for a nail, adhesive is not necessary).

Rolled fabrication techniques of the present invention may also be used to manufacture multilayer electroactive polymer devices. FIGS. 8A-8C illustrate the fabrication of a multilayer electroactive polymer device 820 using rolling techniques in accordance with one embodiment of the present invention. FIG. 8B illustrates the manufactured device 820, which comprises a rigid frame 822 and an electroactive polymer layer stack 824 wound about frame 822 multiple times. Frame 822 is substantially rectangular in its planar profile and includes four connected rigid elements 823a-d that define a hole 825 within their planar center.

FIG. 8A illustrates polymer 924 disposed on a stretch frame 926 before rolling. Frame 922 is placed at one end of stretch frame 926 and rolled along the polymer 924 end over end. In one embodiment to facilitate end over end rolling, the corners of frame 922 are rounded. After rolling is complete and polymer stack 924 is secured in its rolled configuration, device 920 has a multilayer stack on both the top and bottom sides of hole 925. One of the polymer stacks may be removed, if desired. An adhesive or glue may be used to secure polymer 924 between each layer or to secure each layer to frame 922. Frame 922 maintains the prestrain on polymer 924 originally established using stretch frame 926. As shown in FIG. 8B, polymer stack 924 does not span the entire surface area of hole 925. It device 920 were to be used in a diaphragm mode, polymer stack 924 and frame 922 may be designed such that polymer stack 924 spans the entire area of hole 925.

Figure 8D:
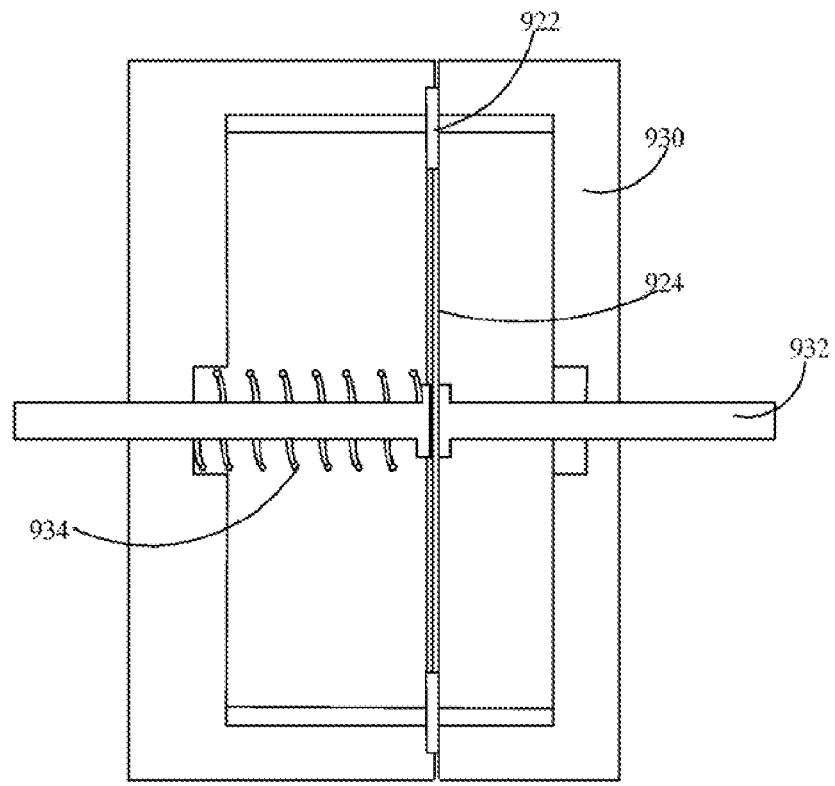
FIGS. 8D and 8E illustrate side perspective views of the pushrod application from FIG. 8C before and after actuation, respectively.
Figure 8E:
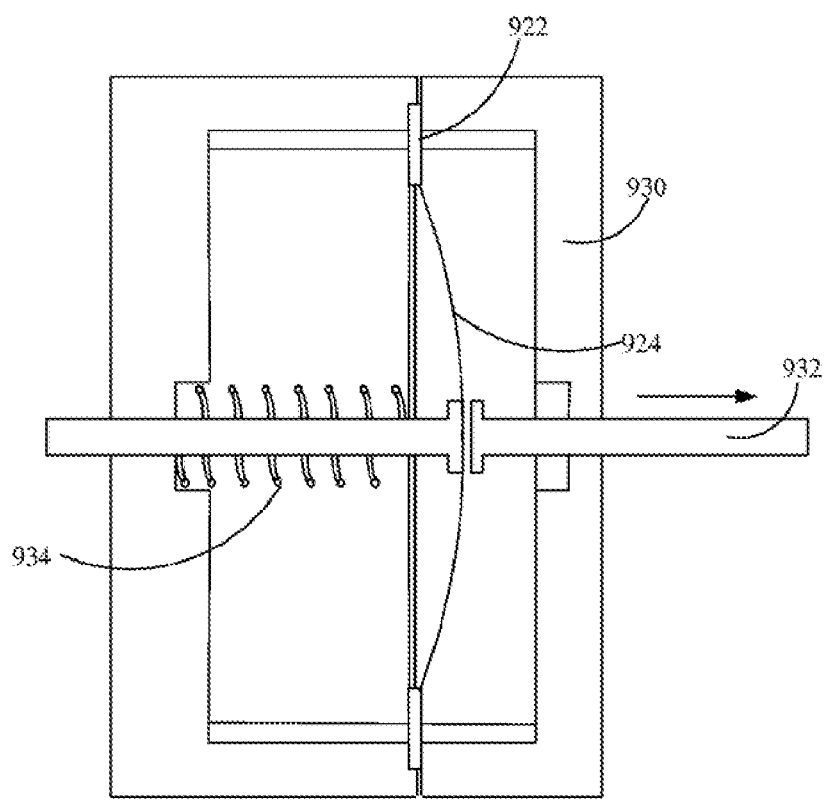

Device 920 may be used for linear actuation. FIG. 8C illustrates device 920 implemented in a pushrod application (after the bottom multilayer stack has been removed). A housing 930 holds frame 922 and allows slideable linear movement of a pushrod 932. Pushrod 932 is attached to polymer 924 on its top and bottom surfaces and polymer 924 deflects normal to hole 925. A spring 934 biases the bottom side of polymer stack 924 and forces it into a curved shape at equilibrium, as shown. In another embodiment, a biasing gel or other biasing material is applied to the bottom surface of polymer stack 924. Biasing Actuation of polymer stack 924 causes pushrod 932 to move to the right. Spring 934 resists deflection away from the equilibrium shown; and when actuation voltages are removed from the polymer, spring 934 pulls pushrod 932 and returns it to the equilibrium position. FIGS. 8D and 8E illustrate side perspective views of the pushrod application from FIG. 8C before and after actuation, respectively.

Applications

Rolled electroactive polymer devices of the present invention have numerous applications. As the present invention includes electroactive polymer devices that may be implemented to perform actuation, stiffness control, damping control, sensing, mechanical output, and/or electrical energy generation, and implemented with a wide variety of designs, the present invention finds use in a broad range of applications. These applications include linear and complex actuators, motors, generators, sensors, robotics, toys, pumps, and fluid flow control. Provided below are several exemplary applications for some of the transducers and devices described above. The exemplary applications described herein are not intended to limit the scope of the present invention. As one skilled in the art will appreciate, transducers of the present invention may find use in countless applications requiring conversion between electrical and mechanical energy.

Rolled electroactive polymer devices of the present invention are well-suited as general linear actuators; and applicable to any applications where linear actuators are useful.

One common application of rolled electroactive polymer devices of the present invention is for robots. One end of a device may be coupled to a robotic link to provide weight bearing, force, stroke, sensing, compliance and motion control capabilities. In one embodiment, a rolled electroactive polymer is used in conjunction with a robotic leg. Conventionally, locomotion for a legged robot is achieved using a leg structure that supports the robot weight that allows for actuation and strain sensor functionality. A relatively sophisticated central control system is required to coordinate the actuation and sensor functions. An electroactive polymer device however allows the design to combine actuation, sensing, and elastic (spring dynamics) and viscoelastic (compliance/damping functionality) properties in one leg structure.

Significant savings in weight and component count are an obvious benefit to robot applications; however, there are others. An electromagnetic actuator or motor is heavy and becomes energy inefficient at small sizes and low speeds. In contrast, a rolled electroactive polymer is lighter, allows higher energy per weight, and better impedance matching to the environment. For sensor functionality, no separate sensor is required with an electroactive polymer device. For stiffness or damping control, no separate spring or damper is required with a suitably electrically controlled multifunctional rolled electroactive polymer device. Thus, the rolled electroactive polymer reduces the component count (vs. a conventional robotic leg with conventional technology) at each joint or leg structure, greatly reducing weight and complexity. In a specific embodiment, rolled electroactive polymers are used in a robot comprising six legs. For example, each leg may have one degree of freedom and disposed at a backward angle. Here, the rolled electroactive polymer device acts as a linear actuator that changes length of the leg structure with polymer deflection. When a rolled electroactive polymer device is actuated, a leg length increases and pushes the robot body forward. Actuating each of the six legs in turn may then be used for legged locomotion of the robot.

Two and three degree of freedom rolled actuators may also be used to provide serpentine robots. In this case, multiple active areas may be disposed along the axial direction as well as the circumferential direction. For example, the serpentine robot may include a rolled electroactive polymer with 60 radially aligned active areas in a 15.times.4 array. The latter number (4) refers to the number of circumferentially disposed active areas (FIG. 3C) while the former number refers to the number of circumferentially disposed active area sets (15). Obviously, other numeric combinations are possible.

The multiple degree of freedom devices may also be used in sensor mode to provide multiple degree of freedom sensing. In one embodiment, rolled electroactive polymer devices of the present invention are implemented in a virtual reality glove or computer input device that includes multiple active areas to detect linear strain of portions of the glove in the immediate area of each transducer. Each active area may be coupled to the glove using glue or integrated into the glove material. Such a device is useful for virtual reality applications, microsurgical applications, and remote surgical applications for example.

The present invention is also well-suited for use with a robotic gripper. Many grasping strategies rely on accurate positioning and compliant contact. Since an electroactive polymer is backdrivable at the compliance of the polymer, grippers that employ multiple degree of freedom electroactive polymer based actuators provide a means for compliant contact—in addition to accurate positioning. For example, a multiple degree of freedom gripper may be designed using rolled electroactive polymer devices as described with respect to FIG. 3C. A gripper the may then comprise several of these fingers.

CONCLUSION

While this invention has been described in terms of several preferred embodiments, there are alterations, permutations, and equivalents that fall within the scope of this invention which have been omitted for brevity's sake. For example, although the present invention has been described in terms of several specific electrode materials, the present invention is not limited to these materials and in some cases may include air as an electrode. In addition, although the present invention has been described in terms of circular rolled geometries, the present invention is not limited to these geometries and may include rolled devices with square, rectangular, or oval cross sections and profiles. It is therefore intended that the scope of the invention should be determined with reference to the appended claims.

We claim:

1. A method for fabricating an electroactive polymer transducer, the method comprising:
    disposing an electrode having a non-uniform shape on an electroactive polymer having an elastic modulus below 100 Mpa;
    creating an electroactive polymer roll by rolling the electroactive polymer such that the electroactive polymer roll has a plurality of layers of the electroactive polymer; and
    securing the electroactive polymer roll to maintain a rolled configuration when converting between electrical and mechanical energy.

2. The method of claim 1, further comprising securing the electroactive polymer roll by applying and adhesive or glue to the electroactive polymer roll to maintain its rolled configuration.

3. The method of claim 1, wherein securing the electroactive polymer roll comprises attaching an end cap to at least one end of the electroactive polymer roll.

4. The method of claim 1, wherein the non-uniform shape of the electrode comprises troughs and crests having a depth and height respectively that is substantially smaller than a thickness of the electroactive polymer.

5. The method of claim 1, wherein creating the electroactive polymer roll comprises rolling the electroactive polymer about at least one of a support member, a mechanical linkage, an end cap, a base or combinations thereof.

6. The method of claim 1, wherein attaching the end cap secures the electroactive polymer roll in its rolled configuration such that actuation of the electroactive polymer transducer results in linear actuation of the transducer.

7. The method of claim 1, wherein the electroactive polymer has a non-uniform first surface, and wherein disposing the electrode having the non-uniform shape on the electroactive polymer comprises conformably disposing the electrode having the non-uniform shape on the non-uniform first surface.

8. A method for fabricating an electroactive polymer transducer, the method comprising:
disposing an electrode having a non-uniform shape on an electroactive polymer having an elastic modulus below 100 Mpa;
creating an electroactive polymer roll by rolling the electroactive polymer such that the electroactive polymer roll has a plurality of layers of the electroactive polymer and where the electroactive polymer roll maintains a rolled configuration while converting between electrical and mechanical energy.

9. The method of claim 8, wherein securing the electroactive polymer roll comprises attaching an end cap to at least one end of the electroactive polymer roll.

10. The method of claim 8, where creating the electroactive polymer roll further comprises applying and adhesive or glue to at least one of the layers of the electroactive polymer to maintain the rolled configuration.

11. The method of claim 8, wherein the non-uniform shape of the electrode comprises troughs and crests having a depth and height respectively that is substantially smaller than a thickness of the electroactive polymer.

12. The method of claim 8, wherein creating the electroactive polymer roll comprises rolling the electroactive polymer about at least one of a support member, a mechanical linkage, an end cap, a base or combinations thereof.

13. The method of claim 8, wherein attaching the end cap secures the electroactive polymer roll in its rolled configuration such that actuation of the electroactive polymer results in linear actuation of the transducer.

14. The method of claim 8, wherein the electroactive polymer has a non-uniform first surface, and wherein disposing the electrode having the non-uniform shape on the electroactive polymer comprises conformably disposing the electrode having the non-uniform shape on the non-uniform first surface.

* * * * *